US012661143B2

(12) United States Patent
Lagoe et al.

(10) Patent No.: US 12,661,143 B2
(45) Date of Patent: Jun. 23, 2026

(54) INTERVENTIONAL SYSTEMS AND ASSOCIATED DEVICES AND METHODS

(71) Applicant: Intervene, Inc., South San Francisco, CA (US)

(72) Inventors: Daniel T. Lagoe, Pacifica, CA (US); Herbert M. Mendoza, South San Francisco, CA (US); Michi E. Garrison, Half Moon Bay, CA (US); Kent D. Dell, Lincoln, CA (US); Jeffrey M. Elkins, Woodside, CA (US)

(73) Assignee: Intervene, Inc., South San Francisco, CA (US)

(*) Notice: Subject to any disclaimer, the term of this patent is extended or adjusted under 35 U.S.C. 154(b) by 489 days.

(21) Appl. No.: 18/120,361

(22) Filed: Mar. 10, 2023

(65) Prior Publication Data

US 2024/0074784 A1     Mar. 7, 2024

Related U.S. Application Data

(60) Provisional application No. 63/269,169, filed on Mar. 10, 2022.

(51) Int. Cl.
 *A61B 17/3207*     (2006.01)
 *A61B 17/32*     (2006.01)

(52) U.S. Cl.
 CPC ............... *A61B 17/320758* (2013.01); *A61B 17/320725* (2013.01); *A61B 2017/32006* (2013.01)

(58) Field of Classification Search
 CPC .... A61B 17/320758; A61B 17/320725; A61B 17/320783; A61B 2017/32006;

(Continued)

(56) References Cited

U.S. PATENT DOCUMENTS

| | | | | |
|---|---|---|---|---|
| 3,082,805 A | * | 3/1963 | Royce | ................... G01N 1/286 |
| | | | | 600/568 |
| 3,320,957 A | * | 5/1967 | Sokolik | ............ A61B 17/32002 |
| | | | | 606/180 |

(Continued)

FOREIGN PATENT DOCUMENTS

| | | |
|---|---|---|
| WO | 2022192897 A1 | 9/2022 |
| WO | 2023172760 A1 | 9/2023 |

OTHER PUBLICATIONS

International Search Report and Written Opinion mailed Aug. 14, 2023, International Application No. PCT/US2023/015029, 16 pages.

*Primary Examiner* — Tan-Uyen T Ho
*Assistant Examiner* — Osama Nemer
(74) *Attorney, Agent, or Firm* — Dorsey & Whitney LLP

(57) ABSTRACT

Devices and systems for removing obstructive material from a blood vessel lumen. For example, the system can comprise a first elongated member, a second elongated member, and a cutting element configured to cut obstructive material at the treatment site. Rotation of the second elongated member relative to the first elongated member, or vice versa, can cause the cutting element to expand away from a longitudinal axis of the second elongated member. The system can further include an expandable positioning element configured to be intravascularly delivered to the treatment site, where the positioning element can be configured to expand into apposition with the vessel wall to position the cutting element closer to the obstructive material than before expansion of the positioning element.

19 Claims, 44 Drawing Sheets

(58) Field of Classification Search
CPC .......... A61B 2017/22051; A61B 2017/22068; A61B 2017/22071; A61B 2017/320716; A61F 2/013; A61F 2002/016
See application file for complete search history.

(56) References Cited

U.S. PATENT DOCUMENTS

| | | | | |
|---|---|---|---|---|
| 3,732,858 A * | 5/1973 | Banko ............. | A61B 17/32002 | 606/107 |
| 4,844,064 A * | 7/1989 | Thimsen ............. | A61F 9/00763 | 30/240 |
| 4,867,157 A * | 9/1989 | McGurk-Burleson ...................... | A61B 17/32002 | 30/240 |
| 4,986,807 A * | 1/1991 | Farr ............... | A61B 17/320783 | 606/159 |
| 5,030,201 A * | 7/1991 | Palestrant ...... | A61B 17/320725 | 600/568 |
| 5,176,693 A * | 1/1993 | Pannek, Jr. .... | A61B 17/320725 | 606/159 |
| 5,226,909 A * | 7/1993 | Evans ............ | A61B 17/320758 | 606/159 |
| 5,242,460 A * | 9/1993 | Klein ............. | A61B 17/320783 | 606/159 |
| 5,403,334 A * | 4/1995 | Evans ............ | A61B 17/320783 | 606/159 |
| 5,527,325 A * | 6/1996 | Conley ............ | A61M 25/0012 | 604/525 |
| 5,554,163 A * | 9/1996 | Shturman ...... | A61B 17/320783 | 606/159 |
| 5,643,296 A * | 7/1997 | Hundertmark ..... | A61B 17/3207 | 606/159 |
| 6,156,046 A * | 12/2000 | Passafaro ............. | A61B 17/221 | 606/159 |
| 6,206,898 B1 * | 3/2001 | Honeycutt ..... | A61B 17/320758 | 606/159 |
| 7,037,316 B2 * | 5/2006 | McGuckin, Jr. ............................ | A61B 17/22032 | 606/113 |
| 9,700,332 B2 * | 7/2017 | Marchand ............... | A61F 2/014 | |
| 9,770,259 B2 * | 9/2017 | Zeroni .......... | A61B 17/320758 | |
| 11,304,723 B1 * | 4/2022 | To ................. | A61B 17/320725 | |
| 12,290,278 B2 * | 5/2025 | Garrison ................ | A61F 2/013 | |
| 2002/0007190 A1 * | 1/2002 | Wulfman ....... | A61B 17/320725 | 606/171 |
| 2002/0010487 A1 * | 1/2002 | Evans ............ | A61B 17/320758 | 606/159 |
| 2004/0219028 A1 * | 11/2004 | Demarais ............... | A61M 29/02 | 417/410.4 |
| 2009/0018567 A1 * | 1/2009 | Escudero ....... | A61B 17/320758 | 606/159 |
| 2009/0138031 A1 * | 5/2009 | Tsukernik ...... | A61B 17/320758 | 606/159 |
| 2015/0335348 A1 * | 11/2015 | Cohen ............ | A61B 17/320725 | 606/159 |
| 2016/0310163 A1 * | 10/2016 | Pigott ............ | A61B 17/320725 | |
| 2016/0354107 A1 | 12/2016 | Nakano et al. | | |
| 2020/0146709 A1 | 5/2020 | Vetter et al. | | |
| 2020/0289102 A1 * | 9/2020 | Wilson ........... | A61B 17/320016 | |
| 2021/0307767 A1 * | 10/2021 | Gifford, III .......... | A61B 17/221 | |
| 2021/0315597 A1 | 10/2021 | Buck et al. | | |
| 2022/0378463 A1 * | 12/2022 | Pigott ................ | A61B 17/3209 | |
| 2023/0063577 A1 * | 3/2023 | Pons ............. | A61B 17/320783 | |

* cited by examiner

112

302        1502        1500

112

1502

302

1502        1600

INTERVENTIONAL SYSTEMS AND ASSOCIATED DEVICES AND METHODS

CROSS-REFERENCE TO RELATED APPLICATIONS

This application claims the benefit of priority to U.S. Provisional Application No. 63/269,169, filed Mar. 10, 2022, which is incorporated herein by reference in its entirety.

TECHNICAL FIELD

The present technology relates generally to interventional systems and associated devices and methods.

BACKGROUND

Deep vein thrombosis (DVT) is a condition comprising a blood clot in a deep vein, usually a leg vein though they can also occur in arm veins. Symptoms include pain, swelling, tenderness, and/or discoloration in the affected limb. If untreated, it can lead to worsening of symptoms and complications such as post-thrombotic syndrome with symptoms of chronic pain, swelling, and skin discoloration, or pulmonary embolism (PE), a very serious and life-threatening condition. Pharmacologic treatments include blood-thinning medications or thrombolytic drugs. More recently, percutaneous catheters have been developed for the more rapid removal of clot to remove the blockage and prevent PE. These include catheters which can deliver thrombolytic agents to the site of the clot, in some cases in combination with aspiration and/or the disruption of the clot into smaller pieces. Other catheters mechanically capture and remove clot without thrombolytic agents, thereby reducing the bleeding risk incurred by these drugs. An early example of this is the Fogarty Balloon Thrombectomy catheter. More recent examples include the ClotTriever® (Inari Medical, Irvine, CA) and the ReVene® Thrombectomy Catheter (Vetex Medical, Galway, Ireland).

Unfortunately, many of these therapies have limited success for partial or full blockages caused by chronic thrombus (i.e., a thrombus over one or two months old). As the clot remains in the limb over a period of months, the initial thrombus transforms into a fibrin and/or collagen structure which is tougher and more firmly adhered to the wall. Chronic thrombus may take the form of fibrous trabeculae or membranes stretching into and across the vein lumen (also known as venous synechiae). Further, the thrombus becomes more firmly attached to the wall. Catheter-based thrombolysis or thrombectomy devices have a lower success rate in removing these blockages. Venous synechiae may also prevent optimal treatment of venous obstruction by balloon angioplasty or stenting, as the fibrous structures prevent permanent stretching of the vessel wall. There is a need for an improved endovascular thrombectomy device which is able to successfully remove chronic thrombus.

SUMMARY

The subject technology is illustrated, for example, according to various aspects described below, including with reference to FIGS. 1-52. Various examples of aspects of the subject technology are described as numbered clauses (1, 2, 3, etc.) for convenience. These are provided as examples and do not limit the subject technology.

1. A device for modifying and/or removing obstructive material from a lumen of a blood vessel, the device comprising:
   an elongated member having a proximal portion and a distal portion configured to be intravascularly positioned at a treatment site in a blood vessel adjacent obstructive material;
   a cutting portion disposed at the distal portion of the elongated member, the cutting portion including a cutting element, wherein the cutting portion has a collapsed, low-profile state for delivery to the treatment site and a deployed state for cutting obstructive material at the treatment site, and wherein the cutting element extends radially away from the longitudinal axis of the elongated member in the deployed state; and
   a capturing portion disposed at the distal portion of the elongated member, wherein the capturing portion is configured to collect obstructive material that has been dislodged by the cutting portion.

2. The device of Clause 1, wherein the capturing portion is positioned distal of the cutting portion along the elongated member.

3. The device of Clause 1 or Clause 2, wherein the capturing portion is self-expandable.

4. The device of any one of Clauses 1 to 3, wherein the elongated member comprises a first elongated member and a second elongated member, and wherein the cutting portion is disposed at a distal portion of the first elongated member and the capturing portion is disposed at a distal portion of the second elongated member.

5. The device of Clause 4, wherein the first and second elongated members are configured to rotate and/or translate relative to one another.

6. The device of Clause 4 or Clause 5, wherein the second elongated member is configured to be slidably disposed within a lumen of the first elongated member.

7. The device of Clause 4 or Clause 5, wherein the first elongated member is configured to be slidably disposed within a lumen of the second elongated member.

8. The device of any one of Clauses 1 to 7, wherein the cutting portion comprises a blade disposed along a portion of the cutting element.

9. The device of Clause 8, wherein the blade is disposed along only a proximally facing surface of the cutting element.

10. The device of any one of Clauses 1 to 9, wherein a cutting edge of the cutting element is substantially linear.

11. The device of any one of Clauses 1 to 9, wherein the cutting element wraps around a longitudinal axis of the shaft.

12. The device of any one of Clauses 1 to 9, wherein the cutting element is a first cutting element and the device further comprises a second cutting element that is configured to extend radially away from the longitudinal axis of the elongated shaft in the deployed state.

13. The device of Clause 12, wherein an angle between the first and second cutting elements in the deployed state is less than 180 degrees.

14. The device of Clause 12, wherein an angle between the first and second cutting elements in the deployed state is from about 135 degrees to about 180 degrees.

15. The device of any one of Clauses 1 to 14, wherein the capturing portion and the cutting portion are independently deployable.

16. The device of any one of Clauses 1 to 15, wherein the capturing portion comprises a closed distal end portion and an open proximal end portion.

17. The device of any one of Clauses 1 to 16, wherein the capturing portion comprises a mesh.

18. The device of any one of Clauses 1 to 17, wherein the capturing portion has a first region comprising a braid and a second region comprises a stent.

19. The device of any one of Clauses 1 to 18, wherein, in a deployed state, the cutting element has a proximally facing portion and a distally facing portion, and wherein a sharpened edge of the cutting element is disposed along only the proximally facing portion.

20. The device of any one of Clauses 1 to 18, wherein, in a deployed state, the cutting element has a proximally facing portion and a distally facing portion, and wherein a sharpened edge of the cutting element is disposed along only the distally facing portion.

21. A system for modifying and/or removing obstructive material from a lumen of a blood vessel, the system comprising:

a first elongated member having a proximal portion and a distal portion configured to be intravascularly positioned at a treatment site in a blood vessel adjacent obstructive material;

a second elongated member having a proximal portion and a distal portion configured to be intravascularly positioned at the treatment site;

a cutting portion disposed at the distal portion of the first elongated member, the cutting portion including a cutting element, wherein the cutting portion has a collapsed, low-profile state for delivery to the treatment site and a deployed state for cutting obstructive material at the treatment site, and wherein the cutting element extends radially away from the longitudinal axis of the first elongated member in the deployed state; and a capturing portion disposed at the distal portion of the second elongated member, wherein the capturing portion is configured to collect obstructive material that has been dislodged by the cutting portion.

22. The system of Clause 21, wherein the second elongated member is slidably disposed within a lumen of the first elongated member.

23. The system of Clause 21, wherein the first elongated member is slidably disposed within a lumen of the second elongated member.

24 The system of any one of Clauses 21 to 23, wherein a distal region of the cutting portion is axially fixed to the distal portion of the second elongated member and a proximal region of the cutting portion is configured to move axially along the second elongated member.

25. The system of any one of Clauses 21 to 24, wherein, in a deployed state, the cutting element has a proximally facing portion and a distally facing portion, and wherein a sharpened edge of the cutting element is disposed along only the proximally facing portion.

26. The system of any one of Clauses 21 to 24, wherein, in a deployed state, the cutting element has a proximally facing portion and a distally facing portion, and wherein a sharpened edge of the cutting element is disposed along only the distally facing portion.

27. The system of any one of Clauses 21 to 26, further comprising an introducer sheath, and wherein the first and second elongated members are configured to be slidably disposed in a lumen of the introducer sheath.

28. A device for modifying and/or removing obstructive material from a lumen of a blood vessel, the system comprising:

a first elongated member having a proximal portion and a distal portion configured to be intravascularly positioned at a treatment site in a blood vessel adjacent obstructive material, wherein the first elongated member defines a lumen extending therethrough;

a second elongated member having a proximal portion and a distal portion configured to be intravascularly positioned at the treatment site, wherein the second elongated member is configured to be rotatably disposed within the lumen of the first elongated member;

a cutting element configured to cut obstructive material at the treatment site, the cutting element having a proximal end region at the distal portion of the first elongated member and a distal end region at the distal portion of the second elongated member, wherein rotation of the second elongated member relative to the first elongated member, or vice versa, causes the cutting element to expand away from a longitudinal axis of the second elongated member.

29 The device of Clause 28, wherein the cutting element wraps at least partially around the longitudinal axis of the second elongated member as it extends between the first elongated member and the second elongated member.

30. The device of Clause 28 or Clause 29, wherein the cutting element is a ribbon.

31. The device of any one of Clauses 28 to 30, wherein the cutting element has longitudinally extending edges, and wherein one or both longitudinally extending edges are sharpened.

32 The device of any one of Clauses 28 to 30, wherein the cutting element has a proximally facing longitudinal edge and a distally facing longitudinal edge, and wherein only one of the proximally facing or distally facing longitudinal edge is sharpened.

33 The device of any one of Clauses 28 to 32, wherein the cutting element is a first cutting element and the device comprises a second cutting element.

34 The device of Clause 33, wherein the second cutting element is positioned radially inwardly of the first cutting element.

35. The device of Clause 33, wherein the second cutting element is positioned radially outwardly of the first cutting element.

36. The device of any one of Clauses 33 to 35, wherein the second cutting element is substantially linear.

37. The device of any one of Clauses 33 to 35, wherein the second cutting element wraps at least partially around the longitudinal axis of the second elongated member.

38. The device of any one of Clauses 33 to 37, further comprising a third elongated member positioned between the first and second elongated members, and wherein the second cutting element is at a distal portion of the third elongated member.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIG. 27A shows the cutting portion in a collapsed state. FIG. 27B shows the cutting portion in an expanded state.

FIG. 28A shows the cutting portion in a collapsed state. FIG. 28B shows the cutting portion in an expanded state.

DETAILED DESCRIPTION

Figure 1:
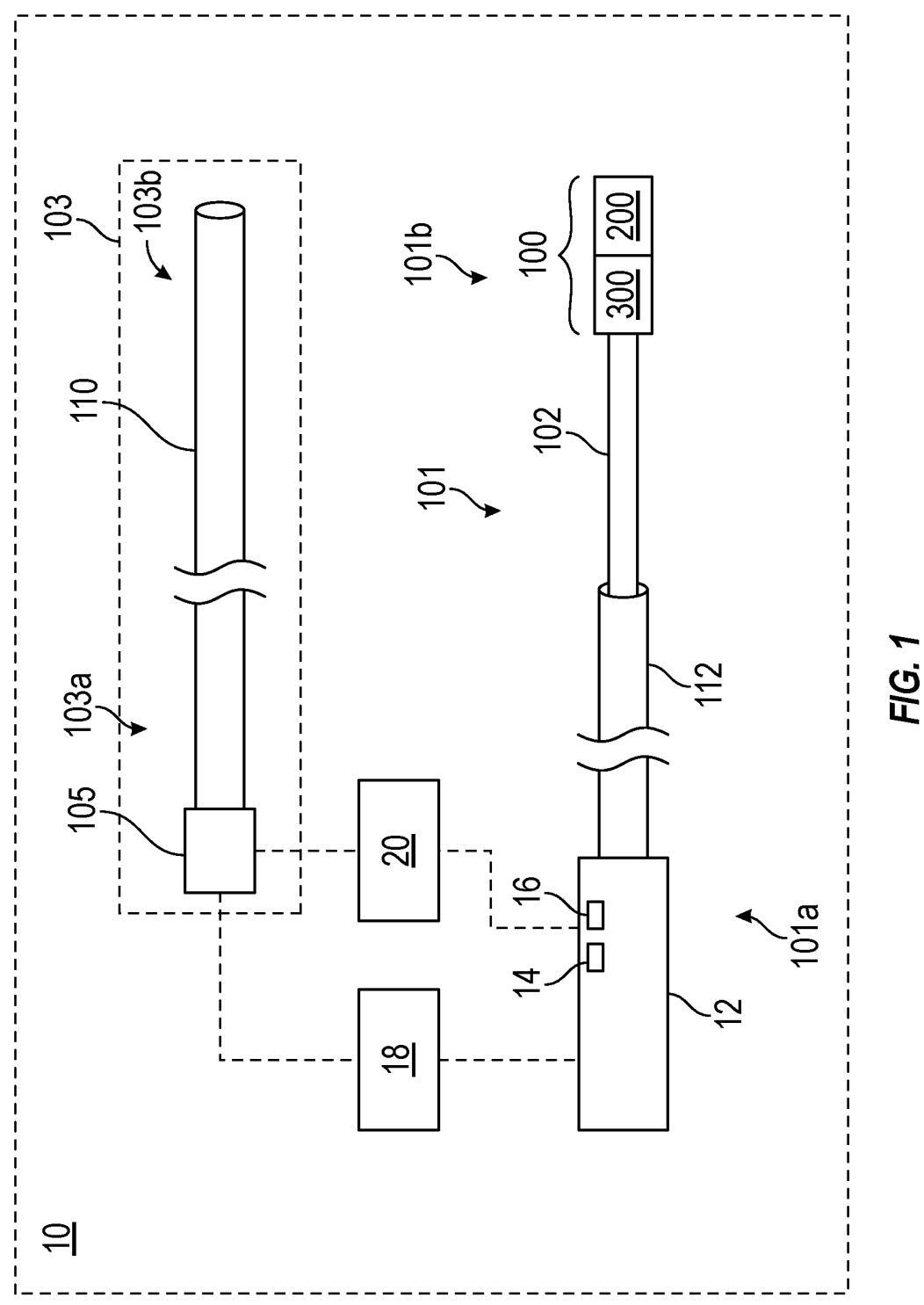
FIG. 1 schematically depicts a treatment system configured in accordance with several embodiments of the present technology.

FIG. 1 schematically depicts a treatment system 10 (also referred to herein as "the system 10") configured in accordance with the present technology. The treatment system 10 is configured to access a body lumen (such as a vein or artery) and modify, capture, and/or remove obstructive material from the body lumen. As used herein, "obstruction" or "obstructive material" can comprise, for example, clot material, atherosclerotic plaque, and/or other flow-obstructing structures, including those derivative of clot material, such as fibrotic clot material, venous synechiae, fibrinous structures, collagenous structures, fibrous trabecular, and/or others. As shown in FIG. 1, the system 10 may comprise a treatment device 101 (or "device 101") having a proximal portion 101a configured to be positioned extracorporeally during the procedure, a distal portion 101b configured to be positioned at a treatment site within a blood vessel, and one or more elongated members 102 extending between the proximal portion 101a and the distal portion 101b. The treatment device 101 can also include a handle 12 and a sleeve 112 extending distally from the handle 12. The elongated member 102 can be configured to be slidably disposed within a lumen of the sleeve 112. In several embodiments, the treatment device 101 does not include one of the sleeve 112 or the elongated member 102. In these and other embodiments, the treatment device 101 includes two or more elongated members. In some of such embodiments, the treatment device 101 does not include a sleeve 112 and the elongated member 102 includes at least first and second elongated members 111, 108 (described below with reference to FIG. 2).

The treatment device 101 may include at least one lumen configured to accept a guidewire (not shown) or other guide rail so that the device 101 may be positioned over the guidewire to a treatment site. The lumen may extend along the elongated member 102 (or any component thereof, including one or both of the first and second elongated members 111, 108 discussed with reference to FIG. 2) and terminate distally at a distal opening. The lumen may also be configured to receive a visualization device therethrough.

The treatment device 101 further includes a treatment assembly 100 (or "assembly 100") carried by a distal portion of the elongated member 102. The treatment assembly 100 can comprise a capture portion 200 and a cutting portion 300, which may be integral with one another or separate components. The cutting portion 300 can comprise one or more cutting elements configured to cut through obstructive material in the vessel lumen as the treatment assembly 100 is moved axially along the lumen, thereby separating and/or releasing obstructive material from the vessel wall and/or from other obstructive material. The capture portion 200 can comprise one or more expandable mesh structures configured to engage, trap, or otherwise become enmeshed with obstructive material at the treatment site, before, during, or after engagement by the cutting portion 300. The capture portion 200 can comprise any of the capture portions 200 described herein, and the cutting portion 300 can comprise any of the cutting portions 300 described herein. In some embodiments, the treatment system 10 can include only the cutting portion and be used with a separate, off-the-shelf capture device. Additional details regarding the capture portion 200 and the cutting portion 300 are described below.

Figure 2:
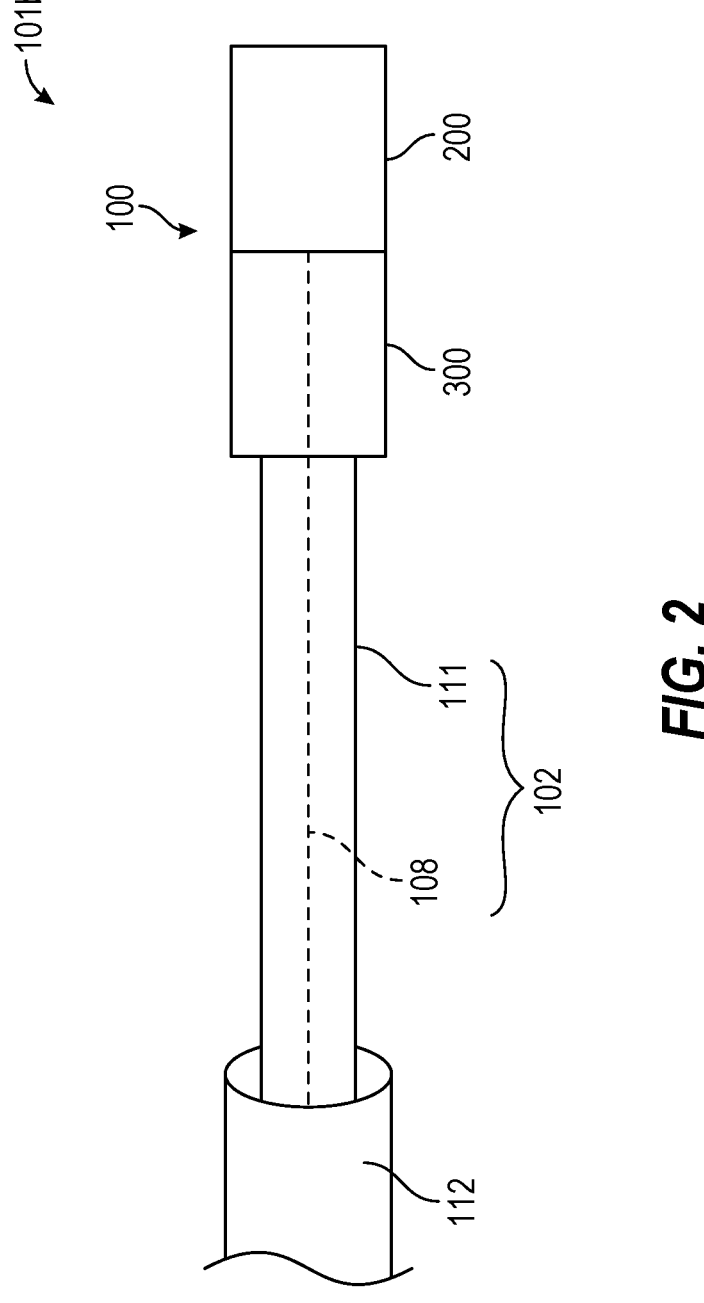
FIG. 2 schematically depicts a distal portion of a treatment system configured in accordance with several embodiments of the present technology.

The treatment assembly 100 is transformable between a low-profile state for delivery to the vessel lumen and a deployed (e.g., expanded) state, as detailed herein. As used herein with reference to the treatment assembly 100, "expanded" and "deployed" refer to a configuration of the treatment assembly 100 when one or both of the capture portion 200 and the cutting portion 300 are in a partially or fully expanded state. According to several embodiments described herein, the capture portion 200 and the cutting portion 300 are integrated into a single expandable device. In some of such embodiments, the treatment assembly 100 is self-expanding and coupled to a distal end portion of a single elongated member 102. In other embodiments in which the capture portion 200 and the cutting portion 300 are integrated into a single expandable device, the treatment assembly 100 (regardless of whether the treatment assembly 100 is self-expanding or requires activation) is coupled to at least two elongated members 108, 111, as shown in FIG. 2. The sleeve 112 may be positioned over the treatment assembly 100 to radially constrain and/or protect the treatment assembly 100 while being introduced to the vessel lumen. In such embodiments, the sleeve 112 is withdrawn proximally to expose the treatment assembly 100 to allow one or more portions of the treatment assembly 100 to expand.

According to several aspects of the technology, the capture portion 200 and the cutting portion 300 are independently deployable. In such embodiments, both the capture portion 200 and the cutting portion 300 can be self-expanding and be coupled to the same elongated member 102 or may be coupled to separate elongated members.

Figures 3A, 3B:
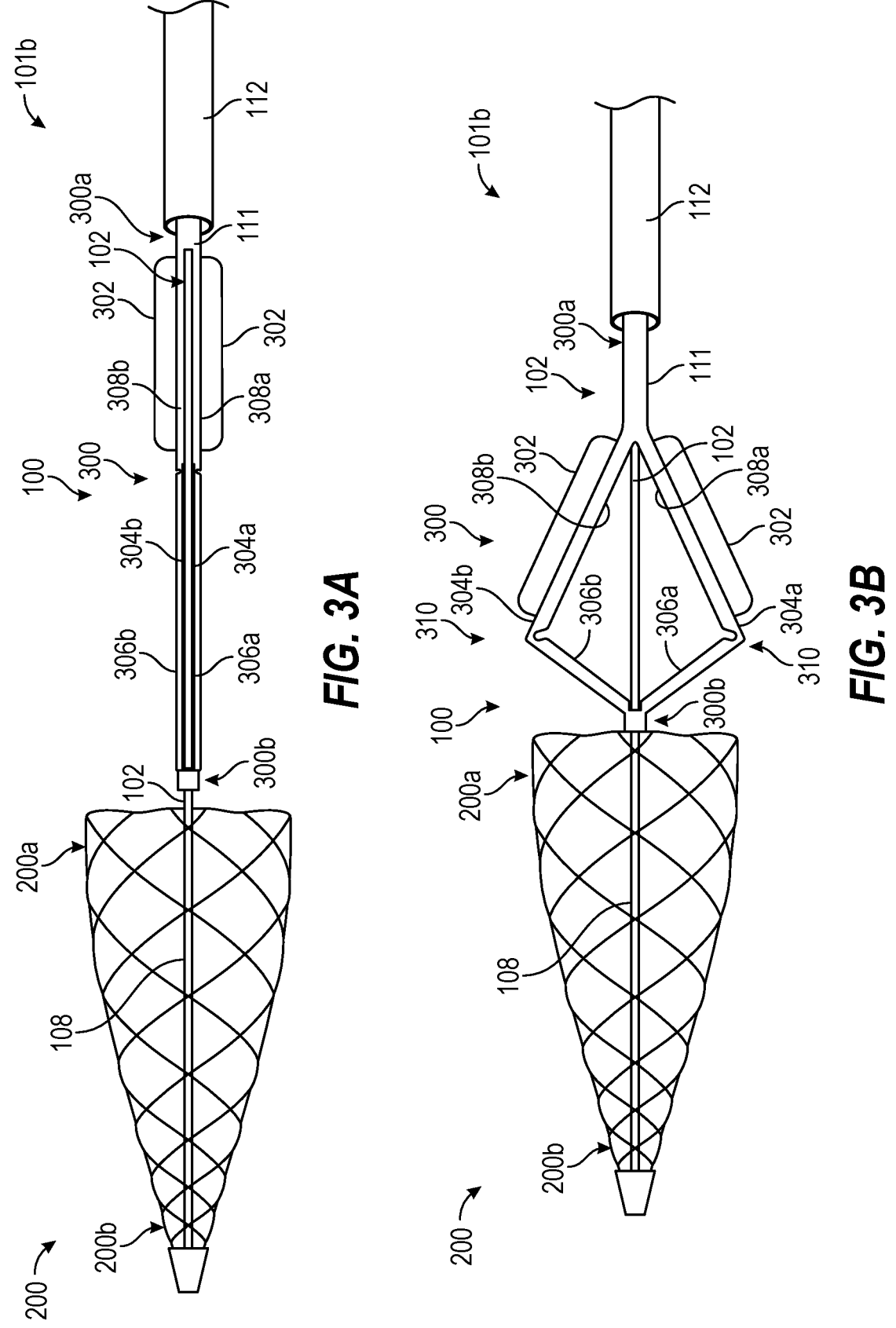
FIGS. 3A and 3B are top views of a treatment assembly configured in accordance with several embodiments of the present technology, shown in a collapsed state and an expanded state, respectively.

In some embodiments the capture portion 200 and the cutting portion 300 comprise separately formed components, both carried by the distal region of the elongated member 102. One of many examples of such embodiments is shown in FIGS. 3A and 3B. In these embodiments, the capture portion 200 and the cutting portion 300 can be configured to collapse and expand independently of one another or via the same actuation mechanism. For example, the capture portion 200 can be a resilient structure configured to self-expand upon withdrawal of a sleeve 112, while expansion of the cutting portion 300 may require an additional actuation step by the operator (as detailed herein). Likewise, the cutting portion 300 can be a resilient structure configured to self-expand upon withdrawal of the sleeve 112, while expansion of the capture portion 200 may require an additional actuation step by the operator (as detailed herein). According to some examples, both the capture portion 200 and cutting portion 300 are resilient, self-expanding structures.

Referring still to FIG. 1, the handle 12 at the proximal portion 101a of the treatment device 101 can be permanently or detachably coupled to one or more of the elongated members (such as the sleeve 112, the elongated member 102, the inner member 108, the outer member 111, etc.). The handle 12 can include one or more actuators for controlling movement of one or more portions of the treatment assembly 100. For example, the handle 12 can include a first actuator 14 that is mechanically (e.g., via a push rod, push tube, and/or pull-wire) and/or electrically (e.g., via one or more wires) coupled to the capture portion 200 and a second actuator 16 that is mechanically (e.g., via a push rod, push tube, and/or pull-wire) and/or electrically (e.g., via one or more wires) coupled to the cutting portion 300. Activation of the first actuator 14, for example, can control one or more movements of the capture portion 200. In some embodiments, the first actuator 14 controls the axial movement, rotational movement, and/or radial expansion/contraction of some or all of the capture portion 200. In some embodiments, the second actuator 16 controls the axial movement, rotational movement, and/or radial expansion/contraction of some or all of the cutting portion 300. According to some aspects of the technology, the first and/or second actuators 14, 16 and/or a third actuator (not shown) controls the axial movement, rotational movement, and/or radial expansion/contraction of some or all of the capture portion 200 and some or all of the cutting portion 300. For example, the handle 12 can include an actuator that is configured to move the cutting portion 300 axially with respect to the capture portion 200 (or vice versa).

In some embodiments, the first and/or second actuator 14, 16, or an additional actuator (not shown) at the handle 12 is coupled to the sleeve 112 and configured to control axial and/or rotational movement of the sleeve 112. Such an actuator, for example, can be configured to axially advance or withdraw the sleeve 112 to selectively expose or cover all or a portion of the treatment assembly 100. In some embodiments, the first and/or second actuator 14, 16, or an additional actuator (not shown) at the handle 12 is coupled to the elongated member 102 and configured to control axial and/or rotational movement of the elongated member 102. In some embodiments, the first and/or second actuator 14, 16, or an additional actuator (not shown) at the handle 12 is coupled to the inner member 108 and configured to control axial and/or rotational movement of the inner member 108. In some embodiments, the first and/or second actuator 14, 16, or an additional actuator (not shown) at the handle 12 is coupled to the outer member 111 and configured to control axial and/or rotational movement of the outer member 111. The handle 12 can include more or fewer than two actuators (e.g., one actuator, three actuators, four actuators, five actuators, six actuators, etc.).

According to several aspects of the technology, the treatment system 10 optionally includes an introducer 103 for facilitating delivery of the treatment device 101 into the vessel lumen. The introducer 103 can comprise a proximal portion 103a, a distal portion 103b, a hub 105 at the proximal portion 103a, and an elongated sheath 110 extending distally from the hub 105 to the distal portion 103b of the introducer 103. In some embodiments, the hub 105 is configured to be coupled to a suction source 18 and/or a fluid source 20 (e.g., via one or more ports). The hub 105 and sheath 110 can be configured to receive a portion of the treatment device 101 therethrough. For example, the treatment assembly 100, the elongated member 102, and/or the sleeve 112 can be configured to be inserted through the hub 105 and slidably positioned within a lumen of the sheath 110. In some embodiments, the hub 105 comprises a hemostatic valve. According to several embodiments, the introducer 103 includes a funnel at the distal end portion of the sheath 110. Examples of such embodiments are depicted at FIGS. 12A-12C, and 52. The funnel can be configured to expand into apposition with the vessel wall proximate the distal end portion of the sheath 110, thereby preventing released obstructive material from traveling proximally of the introducer 103. In some embodiments, the system 10 does not include an introducer 103.

The treatment system 10 can optionally include a suction or aspiration source 18 (e.g., a syringe, a pump, etc.) configured to be fluidly coupled to a proximal portion of one or more of the introducer 103, the sleeve 112, and/or the elongated member 102 (and/or one or more subcomponents thereof) to apply negative pressure therethrough. In some embodiments, the treatment system 10 includes a fluid source 20 (e.g., a fluid reservoir, a syringe, pump, etc.) configured to be fluidly coupled to a proximal portion of one or more of the introducer 103, the sleeve 112, and/or the elongated member 102 (and/or one or more subcomponents thereof) to supply fluid to the treatment site. The fluid, for example, can be saline, contrast agents, a drug such as a thrombolytic agent, etc.

Actuators on the handle 12 or separate actuators connected directly to the suction source 18 and/or the fluid source 20 may control the application of aspiration and/or flushing through the system 10 to the treatment site. In some embodiments, a single actuator controls both aspiration and flushing. In some embodiments, the suction level from suction source 18 and fluid flow level from fluid source 20 are coupled so as to be on or about the same level, such that there is no fluid buildup at the treatment site. The single actuator can raise or lower this same level.

In some embodiments, the treatment system 10 may include a positioning element configured to position the treatment assembly and/or cutting portion within the blood vessel (or other body lumen) in close proximity to the obstructive material to improve the efficiency of the cutting. The positioning element can additionally or alternatively be utilized to offset the cutting portion from the vessel wall to protect the vessel wall. The positioning element can be part of a separate device over, next to, or through which the treatment device 101 and/or treatment assembly 100 is delivered, or can be incorporated onto the treatment device 101 itself (e.g., disposed on the sleeve 112, the elongated member 102, the first elongated member 111, the second elongated member 108, etc.). The positioning element can be porous (e.g., an expandable cage, strut(s), etc.) or substantially impermeable to blood flow (e.g., a balloon, a covered stent, etc.). Additional details regarding the positioning element are discussed herein.

In some methods of use, the system 10 can be introduced into the venous system from a proximal site (e.g., the common femoral vein, femoral vein, or internal jugular vein) and advanced in a retrograde direction (against normal blood flow) to a treatment site in a vein of the patient's leg. The system 10 can also be introduced into the venous system from a distal site (e.g., a popliteal or more distal vein) and advanced in an antegrade direction (same direction as blood flow) towards the target treatment site. In some embodiments, the system 10 is introduced into an artery for treatment in a patient's artery.

FIGS. 3A and 3B are top views of a distal portion 101*b* of a treatment device 101 with a treatment assembly 100 in various states of deployment, in accordance with embodiments of the present technology. As shown in FIGS. 3A and 3B, the treatment assembly 100 can comprise a capture portion 200 and a cutting portion 300. The capture portion 200 and the cutting portion 300 can be independently deployable. For example, the capture portion 200 is shown in a deployed (e.g., expanded) state in FIGS. 3A and 3B, and the cutting portion 300 is shown in a collapsed state in FIG. 3A and a deployed state in FIG. 3B.

Figure 4:
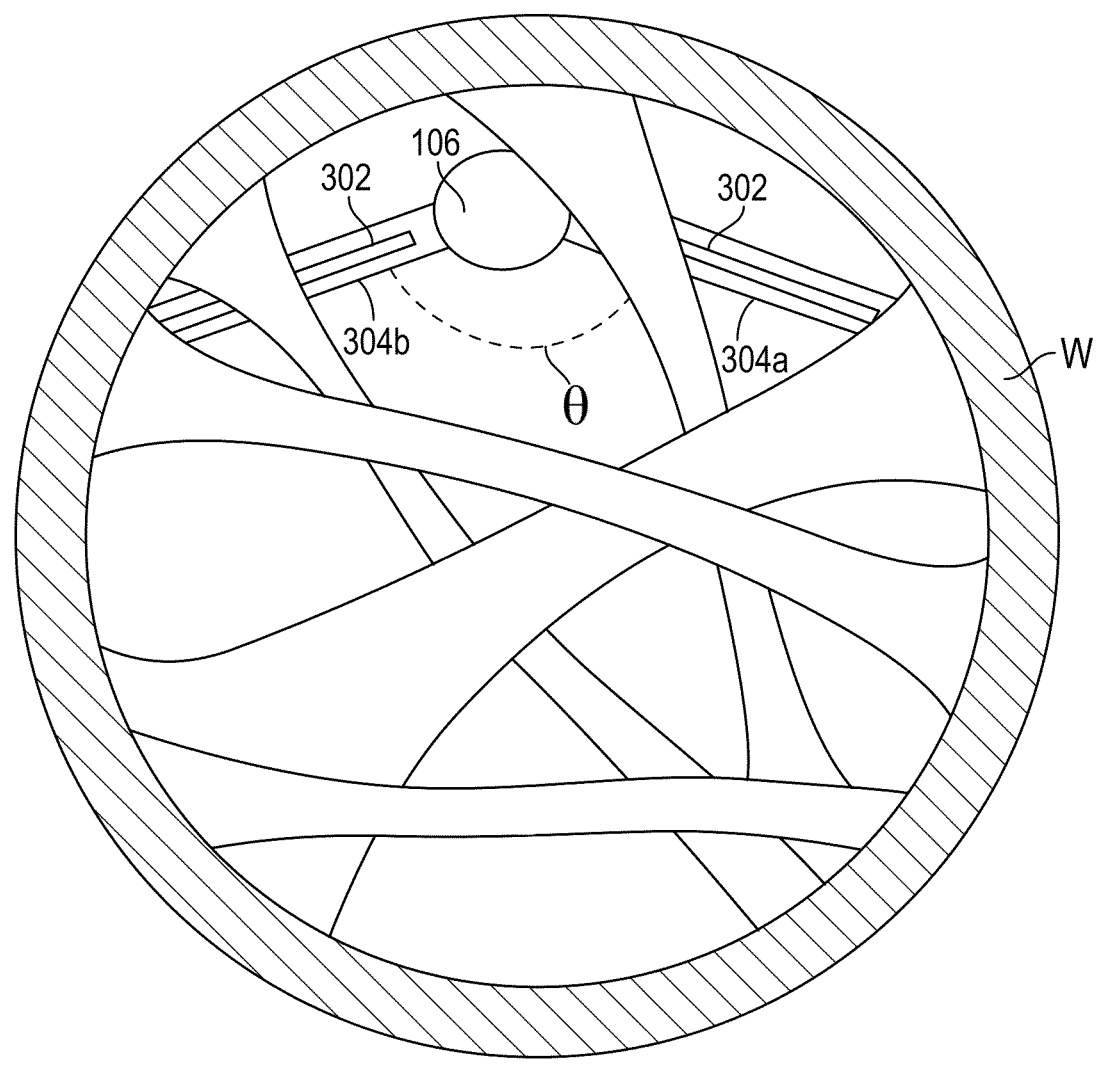
FIG. 4 schematically depicts an end view of a cutting portion of a treatment assembly configured in accordance with several embodiments of the present technology, shown positioned in a blood vessel lumen in an expanded state.

The cutting portion 300 can comprise one or more cutting elements 302 configured to cut through obstructive material in the vessel lumen as the treatment assembly 100 is moved axially along the lumen, thereby separating and/or releasing obstructive material from the vessel wall and/or other obstructive material. FIG. 4 schematically depicts the device positioned within a blood vessel. The arms 304 of the cutting portion 300 may be canted towards each other (rather than extending 180 degree apart) when expanded so that the arms 304 and attached blades 302 are at an angle θ that better approximates the curvature of the vessel wall W. This geometry facilitates cutting obstructive material (such as chronic thrombus material) away from the curved vessel wall. In some embodiments, the angle between the two arms is less than 180 degrees. In some embodiments, the angle is between 135 and 180 degrees.

The capture portion 200 can comprise one or more expandable mesh structures configured to engage, trap, or otherwise become enmeshed with obstructive material at the treatment site. In some embodiments, for example as shown in FIGS. 3A and 3B, the cutting portion 300 can be positioned proximally of some or all of the capture portion 200 along the longitudinal axis of the assembly 100 and/or device 101 such that the portion(s) of the obstruction separated from the vessel wall by the axial movement of the cutting portion 300 are subsequently trapped in and/or become enmeshed with the capture portion 200 for subsequent removal from the patient's body. For example, in some embodiments, all or a portion of the cutting portion 300 is positioned distally of the obstructive material and move proximally, and in some embodiments all or a portion of the cutting portion 300 is positioned proximally of the obstructive material and moves distally towards the capture portion 200.

As depicted in FIGS. 3A and 3B, in some embodiments the capture portion 200 and the cutting portion 300 comprise separately-formed components, both carried by the distal region of the elongated member 102. In such embodiments, the capture portion 200 and the cutting portion 300 can be configured to collapse and expand independently of one another or via the same actuation mechanism. For example, the capture portion 200 can be a resilient structure configured to self-expand upon withdrawal of a sleeve 112, while expansion of the cutting portion 300 may require an additional actuation step by the operator (as detailed herein). Likewise, the cutting portion 300 can be a resilient structure configured to self-expand upon withdrawal of the sleeve 112, while expansion of the capture portion 200 may require an additional actuation step by the operator (as detailed herein). According to some examples, both the capture portion 200 and cutting portion 300 are resilient, self-expanding structures.

In some embodiments of the present technology, for example as shown in FIGS. 3A and 3B, the elongated member 102 can comprise an outer member 111 and an inner member 108 positioned through a lumen of the outer member 111. A proximal end of each of the outer member 111 and the inner member 108 can be disposed at the handle so that the inner and outer members 108, 111 can be manipulated by an operator. In some embodiments, a distal end portion 200*b* of the capture portion 200 is coupled to the distal region of the inner member 108. In the embodiment shown in FIGS. 3A and 3B, for example, only the distal end portion 200*b* of the capture portion 200 is coupled to the distal region of the inner member 108 and the proximal end portion 200*a* is free to expand radially away from the inner member 108 when the sleeve 112 is withdrawn. As a result, when the capture portion 200 is in the expanded state, the proximal end portion 200*a* defines a proximal opening 206 through which obstructive material separated by the cutting portion 300 can pass to trap the obstructive material within an inner cavity defined by the capture portion 200. In some embodiments, only the proximal end portion 200*a* of the capture portion 200 is coupled to the inner member 108 and the distal end portion 200*b* is free and defines a distal opening in the expanded state. In some embodiments, both the proximal end portion 200*a* and the distal end portion 200*b* are coupled to the inner member 108.

Referring still to FIGS. 3A and 3B, a distal end portion 300*b* of the cutting portion 300 can be coupled to the inner member 108, and a proximal end portion 300*a* of the cutting portion 300 can be coupled to a distal end portion of the outer member 111. The distal end portion 300*b* of the cutting portion 300 can be coupled to the inner member 108 at a location that is distal to, generally aligned with, or proximal to the proximal terminus of the capture portion 200. In some embodiments, the distal end portion 300*b* is slidable along the inner member 108. In such embodiments, the inner member 108 may optionally include a distal and/or proximal stop to limit distal and/or proximal axial movement, respectively, of the cutting portion 300 along the inner member 108. In any case, movement of the outer member 111 relative to the inner member 108 can cause the cutting portion 300 to radially expand and collapse. For example, axial movement of the outer member 111 relative to the inner member 108 in a distal direction can cause the cutting portion 300 to radially expand, while axial movement of the outer member 111 relative to the inner member 108 in a proximal direction can cause the cutting portion 300 to radially collapse.

According to several embodiments of the present technology, the cutting portion 300 may comprise a tube with one or more regions removed along the distal portion to form expandable arms 304 (labeled individually as 304*a* and 304*b*). In some embodiments, the outer member 111 and the tube forming the cutting portion 300 are different portions of the same continuous tube. As previously described, distal movement of the outer member 111 with respect to the inner member 108 causes the arms 304 to buckle and/or bend outwardly away from the longitudinal axis of the elongated member 102, as shown in FIG. 3B.

The arms 304 can include one or more segments 306*a*, 306*b*, 308*a*, and 308*b* (referred to collectively as "segments 309") and one or more joints 310. The joints 310 can be positioned along the arms 304 between segments 309 and/or between a respective arm 304 and the rest of the tube from which the arms 304 are cut (e.g., the proximal and distal end portions of the arms 304). The joints 310 can be portions of the arms 304 that are configured to preferentially flex or bend relative to the segments 309 and/or the proximal and distal end portions of the tube. In some embodiments, one or more of the joints 310 can be formed by opposing recesses at a desired location along the arm 304 (e.g., a living hinge), and in other embodiments one or more of the joints 310 can be one or more small pins, elastic polymeric elements, mechanical hinges and/or other devices that enable one segment to pivot or bend relative to another.

In the embodiment shown in FIGS. 3A and 3B, each of the arms 304 includes a distal joint at its distal end portion, a proximal joint at its proximal end portion, and an intermediate joint positioned along the length of the respective arm 304 between the distal and proximal joints. In response to longitudinal stresses caused by relative axial movement of the inner and outer members 108, 110, the arms 304 deform into a predetermined shape biased by the configuration and/or relative positions of the joints 310. For example, in the illustrated embodiment, each of the arms 304, when deployed, includes a generally linear distal segment 306a, 306b and a generally linear proximal segment 308a, 308b. In some embodiments, each of the arms 304, when deployed, includes a generally curved distal segment 306a, 306b and/or a generally curved proximal segment 308a, 308b.

The cutting portion 300 can include one or more cutting elements, such as blades 302, fixedly coupled to one or more segments of the arms. In the embodiment shown in FIGS. 3A and 3B, each of the blades 302 has a sharpened edge that faces proximally when the cutting portion 300 is in the deployed and/or expanded state. The blades 302 may comprise a first material while the arms 304 and/or cutting portion 300 may comprise a second material different than the first material. For example, the blades 302 may comprise stainless steel while the arms 304 and/or cutting portion 300 may comprise a resilient and/or superelastic metal alloy, such as Nitinol, a cobalt-chromium alloy, and others. In some embodiments, the blades 302 comprise the same material as the arms 304. According to several embodiments, the cutting elements are not separately-formed structures and instead are formed of sharpened edges of structure elements of the cutting portion 300.

Figure 5:
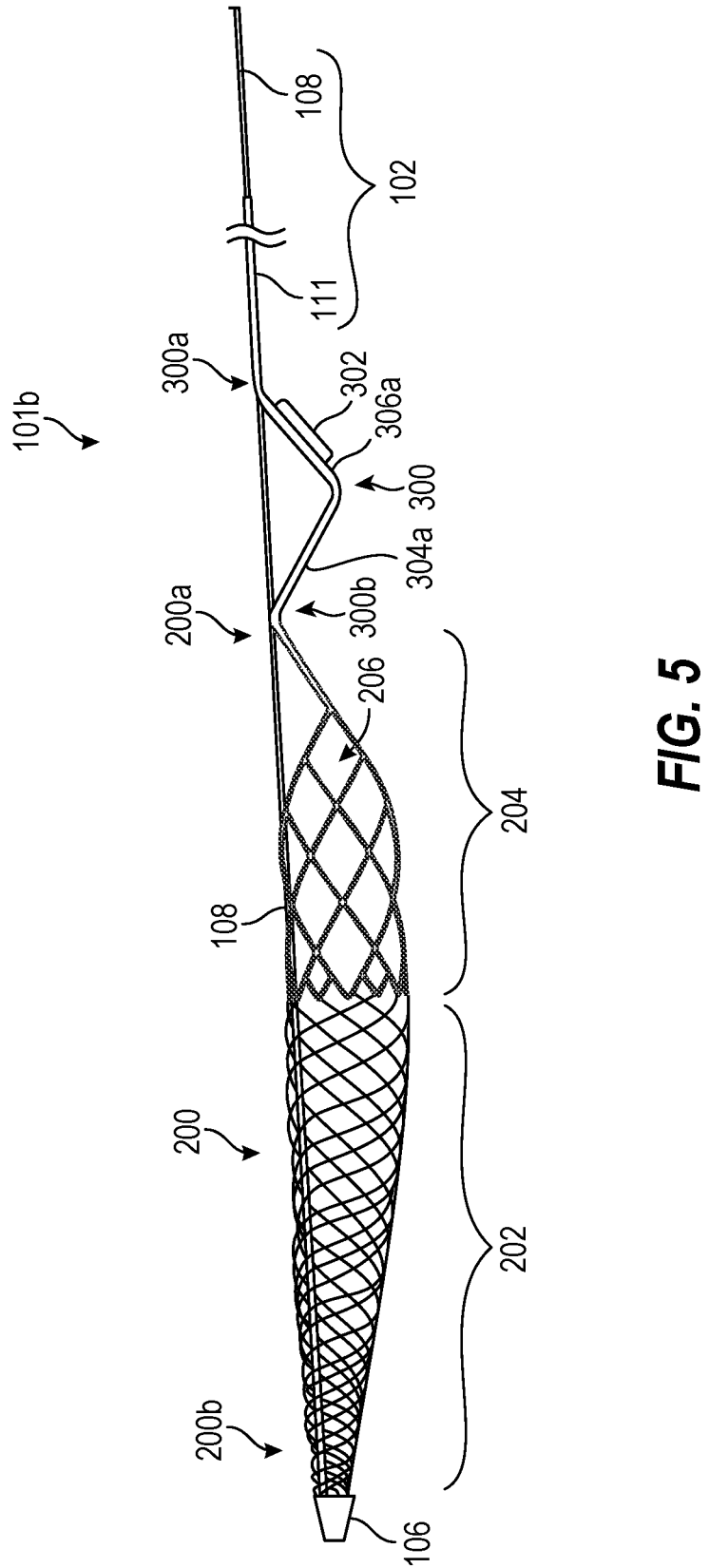
FIG. 5 is a side view of a treatment assembly configured in accordance with several embodiments of the present technology, shown in an expanded state.

FIG. 5 is a side view of a distal portion 101b of a treatment device 101 configured in accordance with several embodiments of the present technology, with the treatment assembly 100 shown in an expanded state. The assembly 100 can comprise an elongated member 102 and a cutting portion 300 that are generally similar to the elongated member 102 and cutting portion 300 discussed above with reference to FIGS. 3A and 3B. The capture portion 200 shown in FIG. 5 can be generally similar to the capture portion 200 shown in FIGS. 3A and 3B, except the capture portion 200 shown in FIG. 5 includes a flexible braided distal region 202 and a more rigid proximal region 204 formed of a laser-cut tube or sheet of material. The tube forming the proximal region 204 can be continuous with or separate from a distal region of the cutting portion 300. The proximal region 204 can have a greater chronic outward force and/or radial resistive force as compared to the distal region 202, which can be beneficial for maintaining the patency of the proximal opening 206 once the capture portion 200 of the assembly 100 and/or device 101 is deployed. In some embodiments, the cutting portion 300 may be fixed to or integral to the capture portion 200. For example, the proximal, open end region 204 of the capture portion 200 may be constructed from a cut nitinol tube. The main structure of the cutting portion 300 may also be constructed from a cut nitinol tube, as described above. The nitinol tube of region 204 and of cutting portion 300 may be the same nitinol tube with two sections of cut pattern. Alternately, nitinol tube of region 204 and of cutting portion 300 may be two separate tubes which are mechanically coupled, glued, soldered or welded, to fixedly couple the capture portion 200 with the cutting portion 300.

Figures 6, 7:
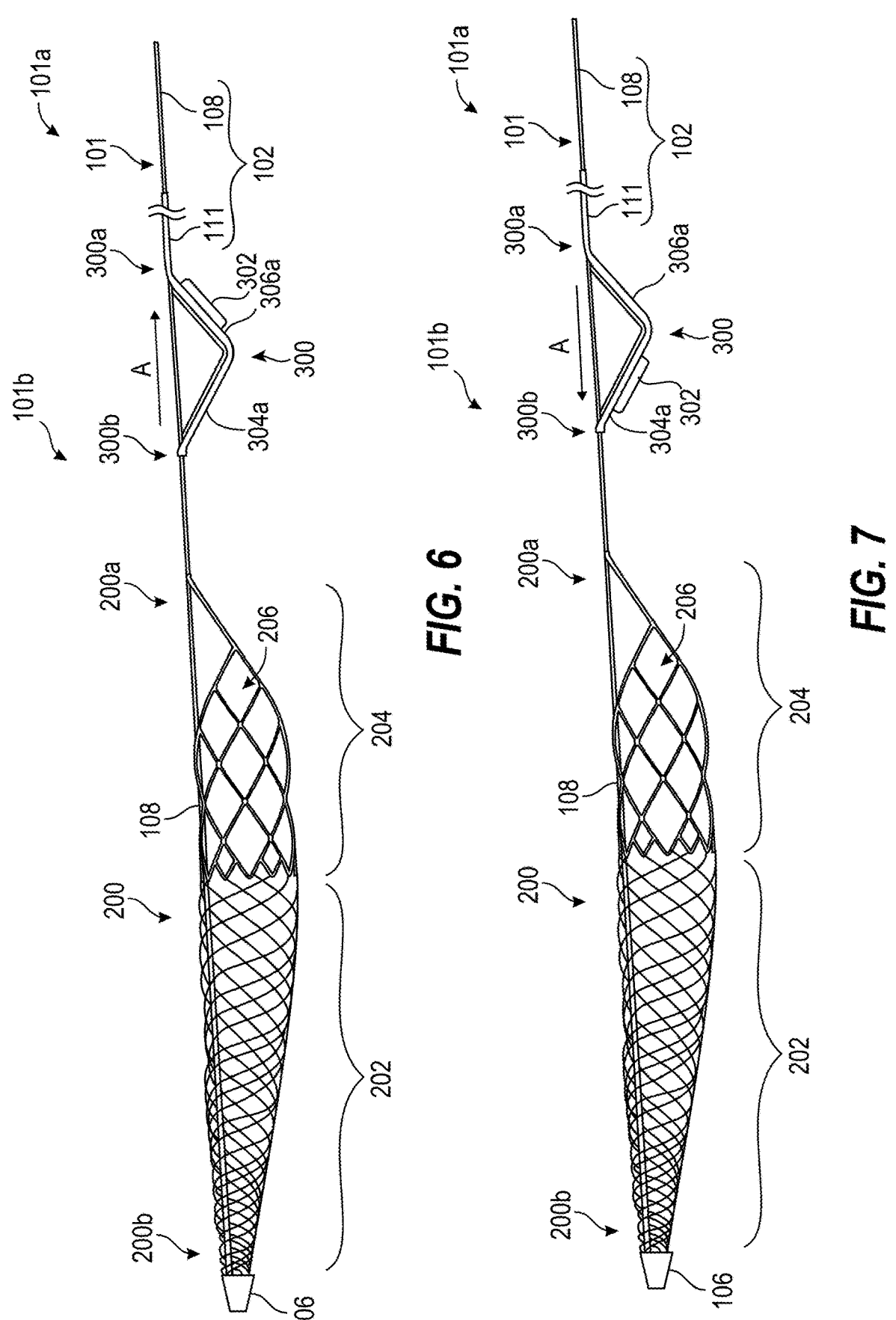
FIGS. 6 and 7 are side views of a treatment assembly configured in accordance with several embodiments of the present technology.

FIGS. 6 and 7 shows a distal portion of a device 101 configured in accordance with several embodiments of the present technology. As shown in FIGS. 6 and 7, in some embodiments the cutting portion 300 and the capture portion 200 are separate components that are spaced apart and slidably coupled. In this embodiment, the blades of the cutting portion 300 of assembly 100 and/or device 101 can face proximally or face distally, depending on how the capture portion 200 and cutting portion 300 are configured to be used with respect to each other. In one variation, shown in FIG. 6, the cutting elements 302 (e.g., blades, etc.) are oriented to face proximally, for example attached to proximal arms 306a and 306b of cutting portion 300. According to some methods of use, the treatment assembly 100 is initially positioned in the blood vessel lumen such that both the capture portion 200 and cutting portion 300 are distal to the obstructive material. The two portions 200, 300 can be expanded, for example, by retraction of a sheath, or by any of the expansion mechanisms described herein. The cutting portion 300 can be pulled proximally to cut through the obstructive material, and subsequently the capture portion 200 can be pulled proximally to gather the cut obstructive material. In some embodiments, the cutting portion 300 and capture portion 200 can alternately and/or simultaneously be pulled back to cut and capture the obstructive material.

In another variation, as shown in FIG. 7, the blades 302 on the cutting portion face distally. For example, the blades 302 can be attached to the distal arms 304a and 304b of the cutting portion 300. According to some methods of use, the treatment assembly 100 is initially positioned in the blood vessel lumen such that the capture portion 200 is distal to the obstructive material and the cutting portion 300 is proximal to the obstructive material. In use, the cutting portion 300 can be moved axially towards the capture portion 200 to separate obstructive material from the wall and push the obstructive material into the capture portion 200.

Figures 8, 9A:
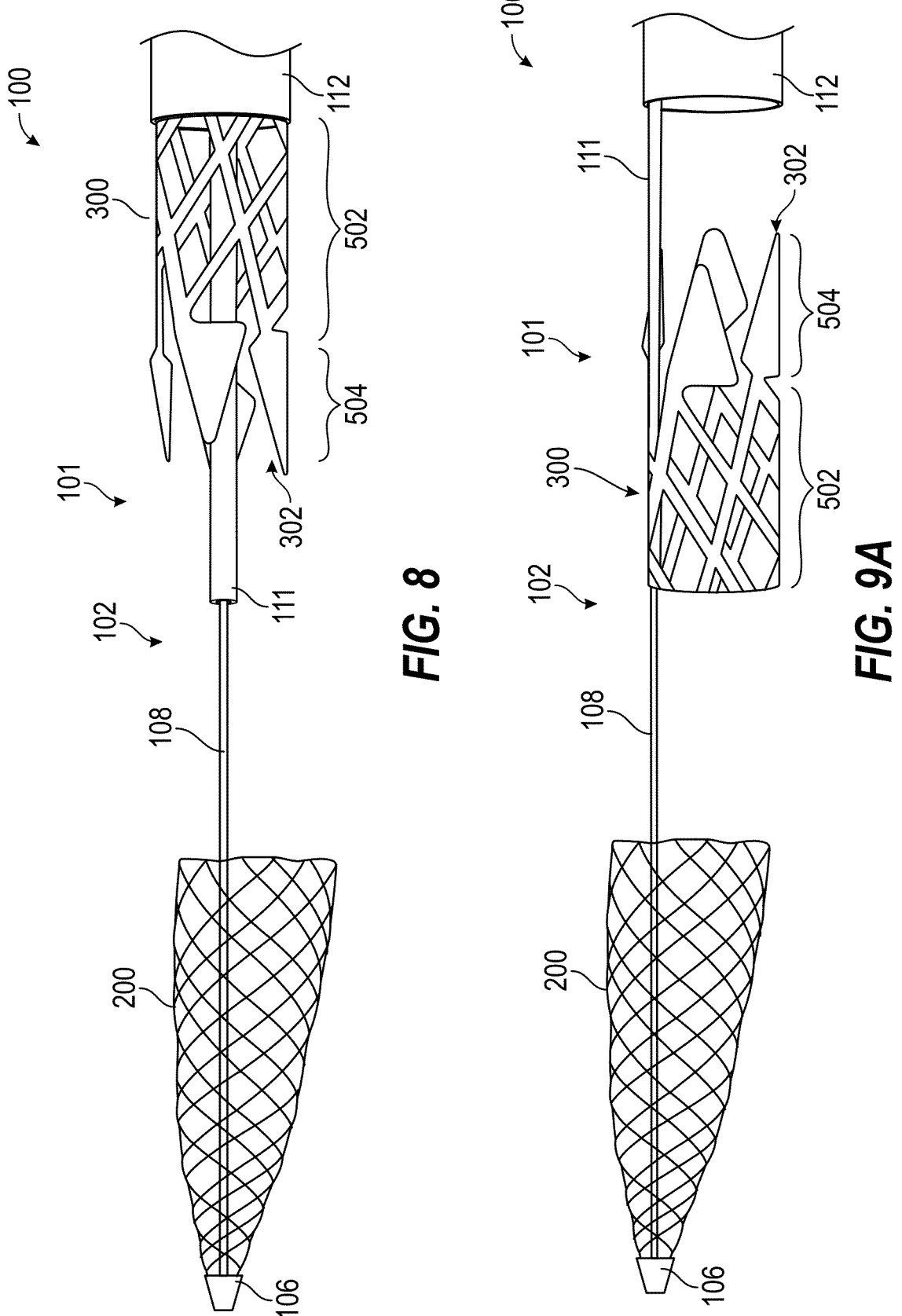
FIGS. 8 and 9A are side views of a treatment assembly configured in accordance with several embodiments of the present technology, shown in an expanded state.

In some embodiments, the cutting portion 300 of the assembly 100 may be an expandable tubular structure with integrated cutting elements. FIG. 8, for example, shows an assembly 100 with a cutting portion 300 comprising a substantially tubular, stent-like portion 502 and a plurality of arms 504 extending away from the stent-like portion 502 in a distal direction. The cutting portion 300 can further include a plurality of cutting elements 302, each disposed at an end portion of a corresponding arm 504. For example, in some embodiments, the cutting portion 300 is constructed from a cut nitinol tube with integrated cutting elements 302 (such as blades) arranged in a circular array. The arms 504 and cutting elements 302 may be spaced apart about a circumference of the cutting portion 300 such that the cutting portion 300 is configured to create a cut that extends circumferentially around the blood vessel wall. Such a feature may be advantageous in some situations due to the amount of obstructive material in the vessel and/or the difficulty with separating the obstructive material from the vessel wall. The cutting edge of the cutting elements 302 may be sharpened and configured to mechanically cut and/or otherwise modify the obstructive material. Additionally or alternatively, the cutting edge of the cutting elements may be configured to chemically cut and/or otherwise modify the obstructive material.

In some embodiments, one, some, or all of the arms 504 are tapered. In some embodiments the arms 504 are not tapered and/or have a generally constant width and/or arc length along their lengths. In a collapsed state (not shown), the distal end portions can be circumferentially spaced apart while the intermediate portions of the projections circumferentially overlap with the circumferentially adjacent projections. In an expanded state (FIG. 8), the end portions of the arms 504 can be circumferentially spaced apart by a greater arc length than when the device was in the collapsed state, and the intermediate portions circumferentially overlap to a lesser extent than in the collapsed state or do not overlap at all.

As shown in FIG. 8, the arms 504 and/or cutting elements 302 can be directed distally towards the capture portion 200. In several of such embodiments, the cutting portion 300 can be configured to move axially relative to the capture portion 200. For example, the cutting portion 300 can be slidably coupled to an outer elongated member 111 while the capture portion 200 can be coupled to an inner elongated member 108. Other configurations that allow independent movement of the capture portion 200 and the cutting portion 300 are possible. In use, the cutting portion 300 can be deployed and/or otherwise positioned proximally of the obstructive material with all or a portion of the capture portion 200 positioned distally of the obstructive material. The cutting portion 300 can be pushed distally to cut the obstructive material and separate the obstructive material from the vessel wall and/or from other obstructive material.

Figure 9B:
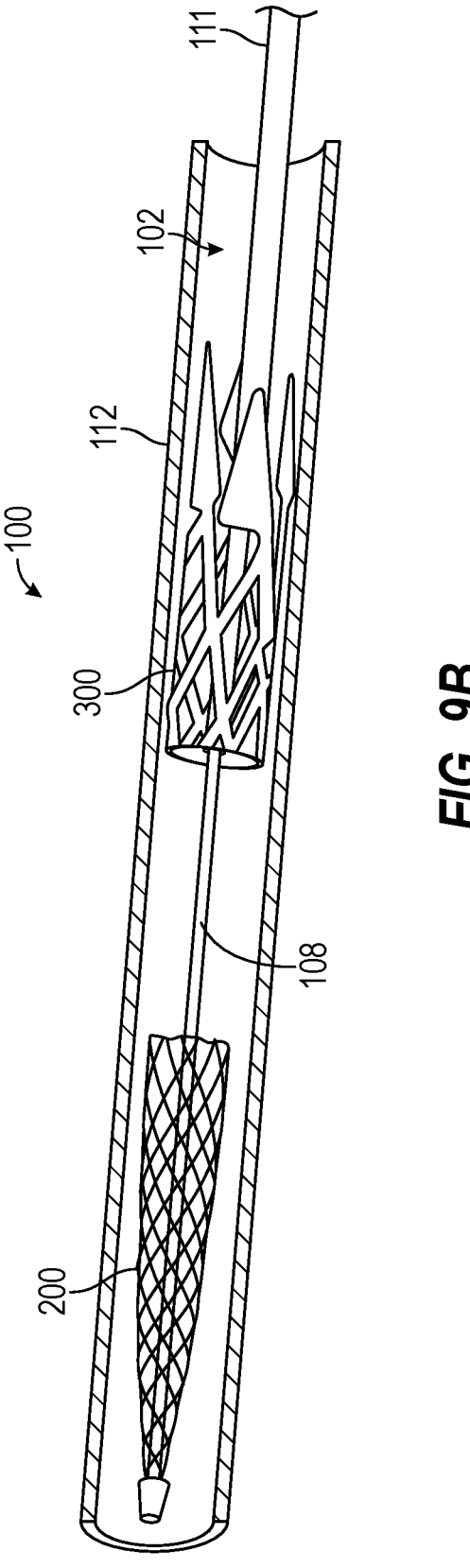
FIG. 9B is a side view of a treatment assembly configured in accordance with several embodiments of the present technology, shown in a collapsed state.

FIG. 9A shows a treatment assembly 100 that is generally similar to the treatment assembly 100 of FIG. 8, except in FIG. 9A the plurality of arms 504 extend away from the stent-like portion 502 in a proximal direction. In use, the capture portion 200 and cutting portion 300 can be deployed and/or otherwise positioned distally of the obstructive material and pulled proximally to cut the obstructive material. FIG. 9B depicts the treatment assembly 100 in a collapsed state within a sleeve 112 (shown in cross-section).

In some embodiments where the capture portion 200 and cutting portion 300 are separately-formed components, the capture portion 200 and the cutting portion 300 can be fixed to one another such that axial and/or rotational movement of one of the portions 200, 300 causes axial movement of all or a portion of the other portion 200, 300. For example, a distal end portion 300b of the cutting portion 300 can be fixedly coupled to a proximal end region 200a of the capture portion 200. If both the cutting portion 300 and the capture portion 200 are fairly rigid structures with high column strength (such as a laser-cut tube or sheet of material), axial movement of the cutting portion 300 will cause axial movement of the entire capture portion 200 and vice versa. If one of the capture portion 200 or the cutting portion 300 is a more flexible structure with low column strength (such as a braid) while the other is a more rigid structure, axial movement of the more rigid structure may cause an end region of the more flexible structure to collapse axially, while axial movement of the flexible structure may not cause any axial movement of the more rigid structure.

According to several embodiments, the capture portion 200 and the cutting portion 300 can be rotated and/or moved axially independently of one another. For example, the elongated member 102 can comprise a first elongated member coupled to the capture portion 200 and a second elongated member coupled to the cutting portion 300. The first and second elongated members can be configured to move axially relative to one another and/or rotate relative to one another (for example, where one elongated member is received within a lumen of the elongated member), thereby causing axial movement and/or rotation of the corresponding attached capture and cutting portions 200, 300. In some embodiments, the capture portion 200 and the cutting portion 300 can be mounted to the same elongated member, but one of the capture portion 200 or the cutting portion 300 is fixed axially and/or rotationally to the elongated member while the other is free to slide along and/or rotate about the elongated member. In some embodiments the capture portion 200 and cutting portion 300 are both fixed axially and/or rotationally to the elongated member.

In any of the embodiments in which the capture portion 200 and the cutting portion 300 are separately-formed components, the capture portion 200 and the cutting portion 300 may be configured to radially expand and collapse independently of one another or via the same actuation mechanism, as discussed herein.

Figures 10, 11:
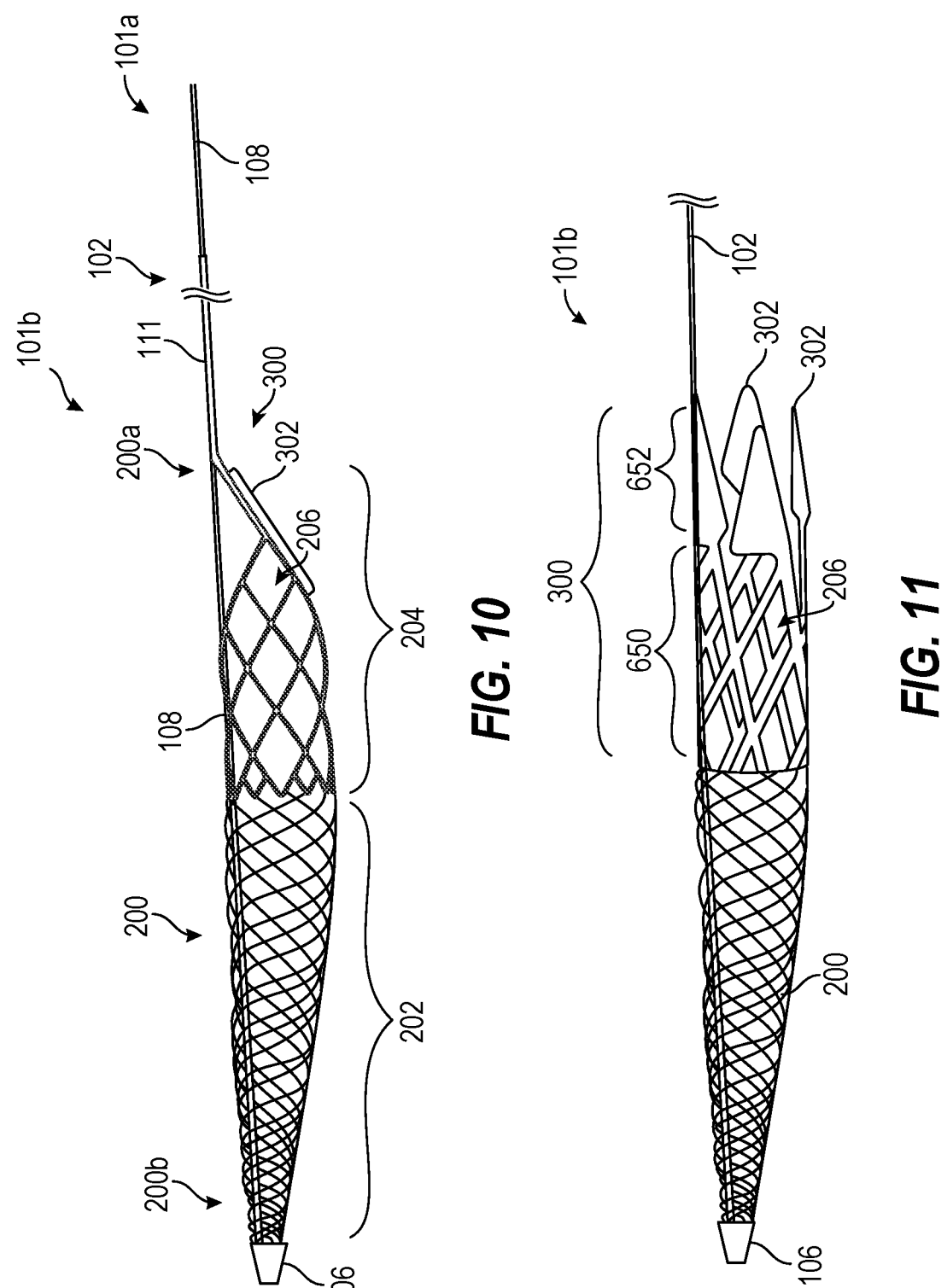
FIG. 10 is a side view of a treatment assembly configured in accordance with several embodiments of the present technology.
FIG. 11 is a side view of a treatment assembly configured in accordance with several embodiments of the present technology, shown in an expanded state.

In some embodiments of the present technology, the cutting portion 300 is integrated within the structure of the capture portion 200 or vice versa. For example, as shown in FIG. 10, the capture portion 200 can have one or more cutting elements 302 facing proximally along a proximal surface of the capture portion and configured to cut obstructive material when the device is pulled back. The cutting elements may be angled with respect to the longitudinal axis of the elongated member 102 to optimize the ability of the blades to slide through the tough material as the device is pulled proximally. The cutting elements can be one or more separately-formed blades coupled to the proximal surface of the capture portion 200. For example, the cutting elements can be separately-formed blades 302 that are mechanically attached to the capture portion 200 (for example via the latching configuration described with respect to FIGS. 19A and 19B). In such embodiments, the struts defining the proximal opening 206 of the capture portion 200 can have slots or other features to mechanically lock the blades 302 in place relative to the struts. Additionally or alternatively, the cutting elements can be formed of the same material and/or structure as the capture portion 200. For example, the cutting elements can be formed of a sharpened, proximally facing surface of the capture portion 200.

In some embodiments, for example as shown in FIG. 11, the cutting elements and/or projections carrying the cutting elements are constructed from the same metal tube that comprises the proximal portion 204 of capture portion 200 and include protruding tapered elements that furl together when collapsed, similar to FIGS. 8-9B. While the assembly 100 in FIG. 11 shows a capture portion 200 comprising a braid, in some embodiments the capture portion 200 may comprise a laser-cut stent.

Regarding FIGS. 8, 9A, 9B, 11, 27A, 27B, 28A, and 28B, one, some, or all of the projections (such as arms 504, arms 652 extending away from stent-like portion 650, projections 1502, etc.) can include a cutting element 302. The cutting element can be coupled to the projection (such as a blade) or the cutting element can be formed from the projection, for example by sharpening one edge/surface of the projection(s). In some embodiments, the cutting elements are positioned at the distal end portions of the projections. In these and other embodiments, the cutting elements may be positioned along all or a portion of one or both side surfaces of a given projection.

When the treatment assembly 100 is in a collapsed state, the projections can be compressed together, and when the treatment assembly 100 is in an expanded state the projections can expand outward to contact and/or conform to the vessel wall. When the treatment assembly is pulled into and through the obstructive material, the cutting elements cut the obstructive material away from the vessel wall. The cutting elements may be configured to be angled such that pulling the device causes the cutting surface to slice across the obstructive material to improve the cutting action. The distal and/or side edges of one, some, or all of the projections and/or blades can be generally linear, generally curved, serrated, and other suitable configurations.

Figures 12A, 12B:
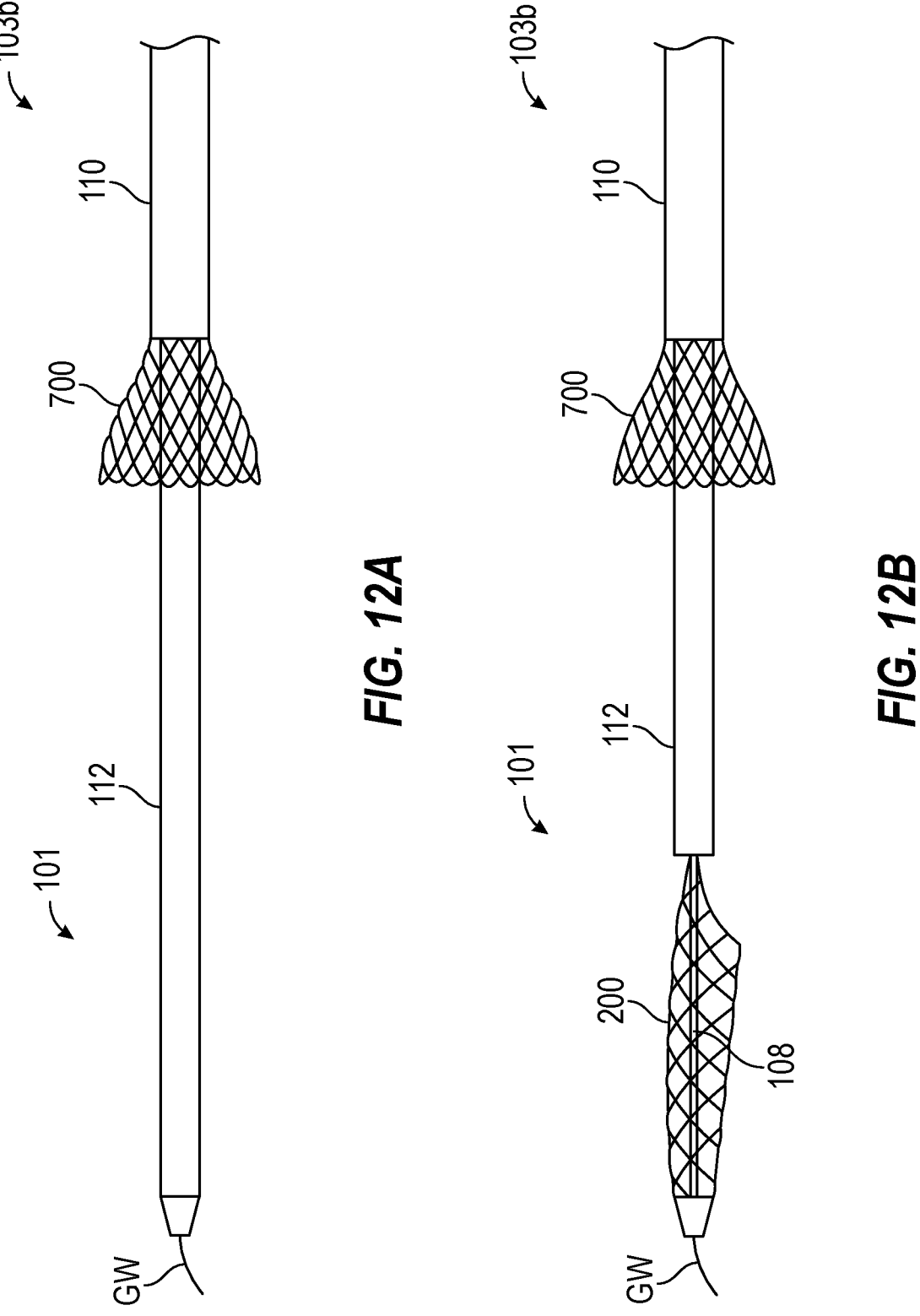
FIGS. 12A-12C are side views of a treatment system having a treatment device and an introducer sheath with a proximal funnel configured in accordance with several embodiments of the present technology.
Figures 12C, 13:
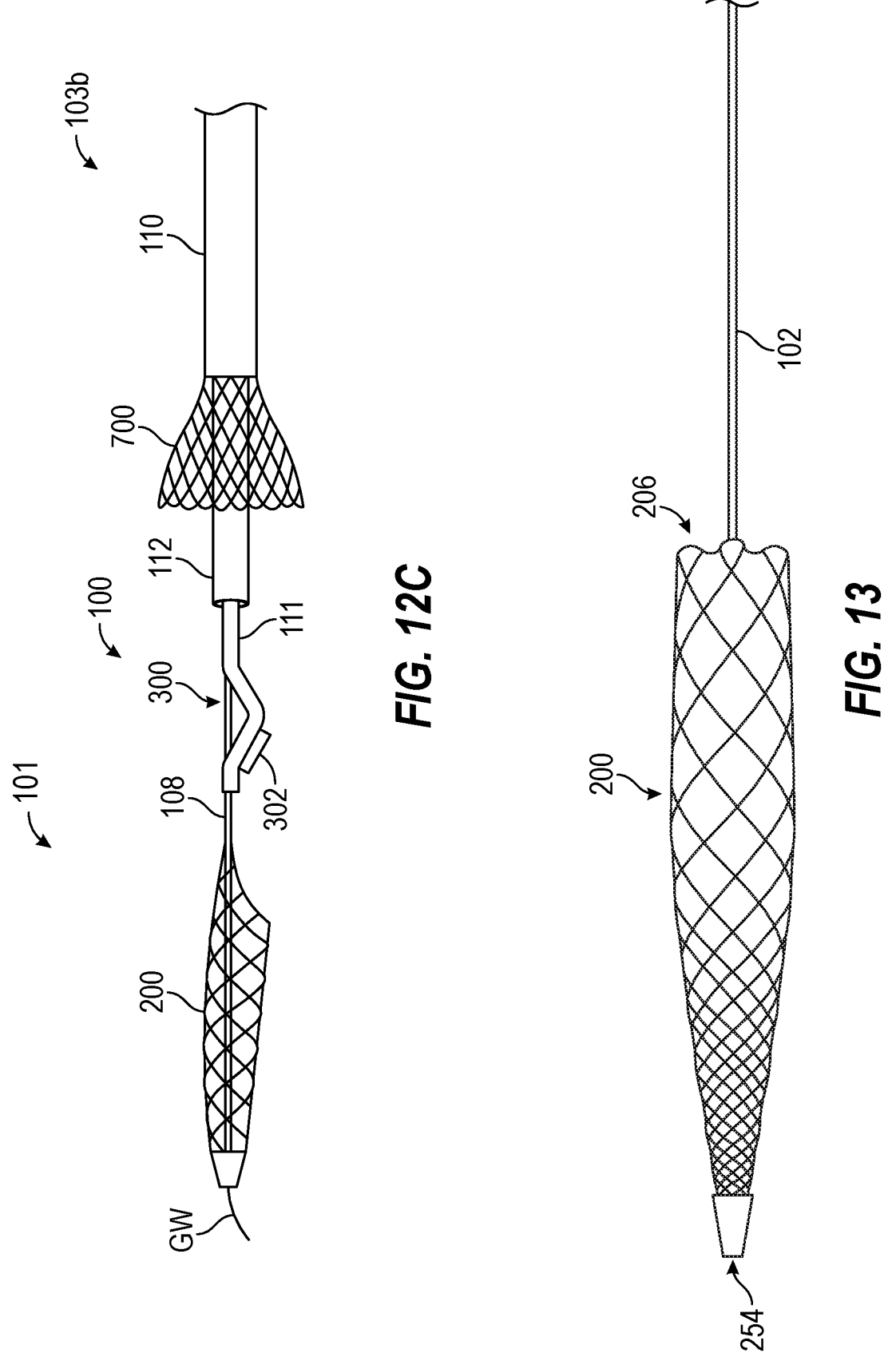
FIGS. 13-16 are side views of capture portions configured in accordance with several embodiments of the present technology.

As previously mentioned, the devices and systems of the present technology can optionally include an introducer 103. The introducer comprises a hub 105 and an elongated sheath 110 with a self-expanding funnel configured to extend distally from the distal opening of the sheath 110. Such a feature can be beneficial for corralling the captured obstructive material into the sheath 110 as the treatment assembly 100 is withdrawn into the sheath 110. An example system 10 including a funnel 700 is shown in FIGS. 12A and 12B. As shown in FIG. 12A, the treatment device 101 with treatment assembly 100 can be delivered in a collapsed state through a sheath 110 with the funnel 700 in an expanded state. Once positioned, the sleeve 112 can be retracted to cause the treatment assembly to expand. FIG. 12B shows the sleeve 112 partially retracted to show the capture portion 200 of the treatment assembly 100 expanded. FIG. 12C shows the sleeve 112 fully retracted to show the cutting portion 300 of the treatment assembly 100 expanded. Additionally or alternatively, aspiration may be applied to the hub 105 of introducer 103 with or without a funnel to further reduce the risk of embolization. The funnel 700 can be used with any of the systems detailed herein.

A. Example Capture Portions

Several capture portion configurations are shown and described with respect to FIGS. 13-16. The cutting portions 300 are not shown in FIGS. 13-16 for ease of viewing the capture portions 200. It will be appreciated that the present disclosure is not limited to the capture portions 200 depicted in the drawings.

FIG. 13 shows a capture portion comprising a braided or woven capture portion 200 having a closed distal end portion and an opening 206 at its proximal end portion. The braid has a tapered shape with a cross-sectional dimension that decreases in a distal direction. The distal end of the braid may be cinched together with a tip component 254, that constrains the ends of the braid wires together. The tip component 254 may have a tapered or rounded distal edge to reduce the trauma to vessel wall as the assembly 100 and/or device 101 is delivered to the treatment site, and to facilitate crossing the device through the treatment site. The tip component 254 may also affix the actuation member 102 to the distal end of the capture device.

Figures 14, 15, 16:
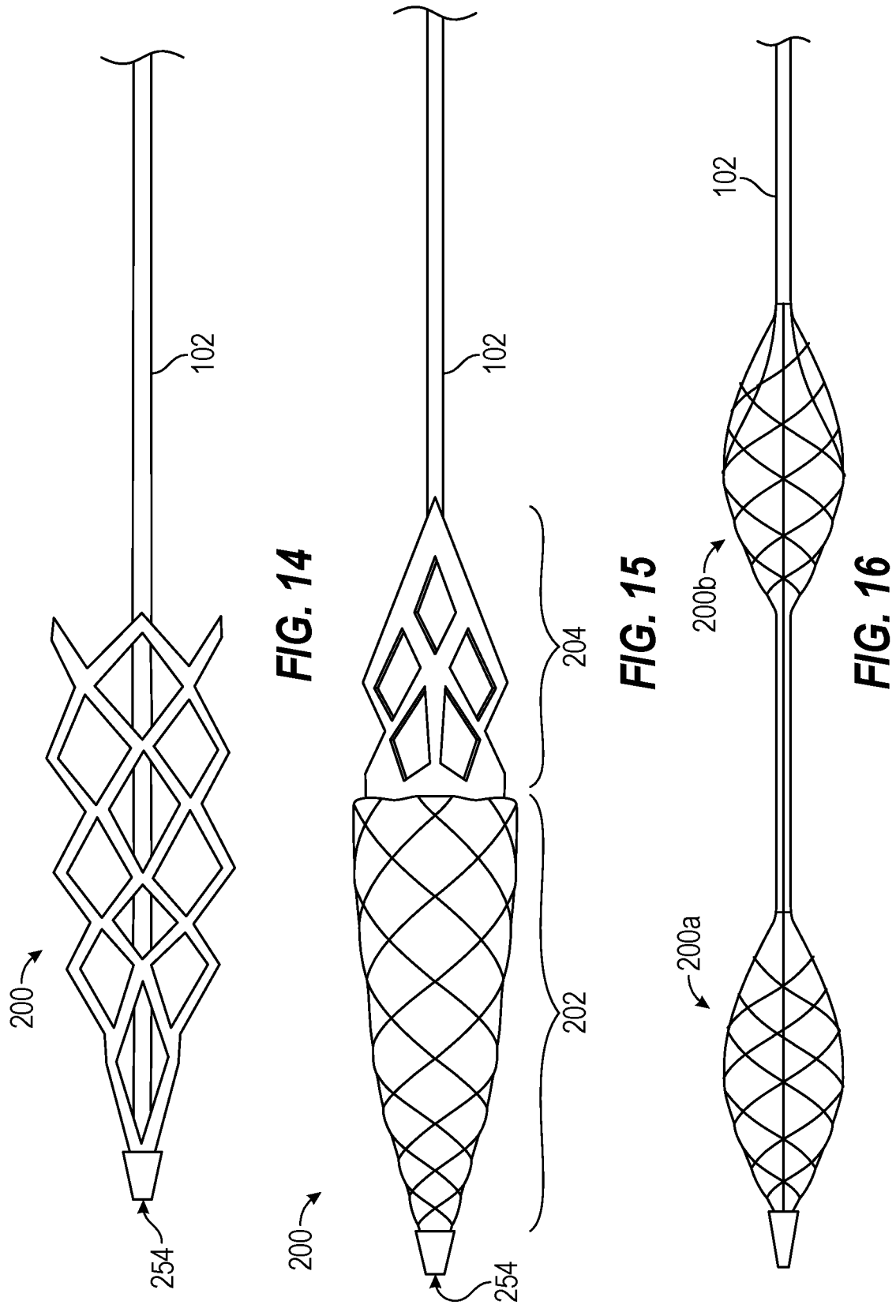

FIG. 14 shows a capture portion 200 comprising a cut mesh structure having a closed distal end portion and an opening at its proximal end portion. The expanded mesh structure has a tapered shape with a cross-sectional dimension that decreases in a distal direction. The closed distal portion may be cinched closed with a tip component 254 that constrains the ends of the cut tube patten together. As above, the tip component 254 may have a tapered or rounded distal end and also may be used to affix the elongated member 102 to the closed end of capture portion 200. In some embodiments, the mesh structure may have a cut pattern that naturally creates a tapered profile when expanded, without tip component 254. A tip component 254 may still be present in this embodiment to present a tapered or rounded distal end and/or to affix the elongated member 102 to the closed end of capture portion 200.

FIG. 15 shows a capture portion 200 comprising a flexible, tapered distal region 202 coupled to a more rigid proximal region 204. The distal region 202 can comprise a braid, and the proximal region 204 can comprise a laser-cut tube or sheet of material. The proximal region 204 can have a greater chronic outward force and/or radial resistive force as compared to the distal region 202, which can be beneficial for maintaining the patency of the proximal opening 206 once the capture portion 200 is deployed in the vessel lumen.

In any of the embodiments disclosed herein, the capture portion 200 can include an open cell framework or body. According to several embodiments, the entrance 206 to the capture portion 200 is slanted to facilitate capture of the obstructive material into the capture portion 200. In some embodiments, the proximal end portion 200a of the capture portion 200 can be generally tubular (including cylindrical), and the distal portion 200b of the capture portion 200 tapers distally down to the elongated member 102 (or component thereof). Likewise, a distal portion 200b of the capture portion 200 is generally tubular (e.g., cylindrical), and the proximal end portion 200a of the capture portion 200 tapers proximally down to the elongated member 102 (or component thereof).

In some embodiments, the capture portion 200 can have an open proximal end and a closed distal end. In some embodiments, the capture portion 200 has an open proximal end and an open distal end. In some embodiments, the capture portion has a closed proximal end and an open distal end. In some embodiments, with reference to 200a of FIG. 16, the capture portion has a closed proximal end and a closed distal end.

In some embodiments, the capture portion 200 comprises a single expandable mesh structure. In some embodiments, for example as depicted in FIG. 16, the capture portion 200 comprises a plurality of expandable structures 200a, 200b. The different structures can have the same or different shapes, can expand to the same or different maximum cross-sectional dimensions, and/or can comprise the same or different type of mesh structure (e.g., a braid, a laser-cut tube, a laser-cut sheet, a weave, etc.).

In some embodiments, the capture portion 200 comprises a mesh structure formed of an elastic or spring material (e.g. stainless steel or cobalt chromium alloy), superelastic material (e.g., Nitinol,.) or other resilient or self-expanding material configured to self-expand when released from the restraining sleeve 112. For example, in some embodiments the mesh is a self-expanding stent and/or stent retriever. According to several embodiments, the mesh structure is a laser-cut tube or sheet of material. The material, for example, can comprise a resilient, elastic, and/or superelastic metal alloy or polymer. In some embodiments, the mesh structure comprises a plurality of braided wires (e.g., filaments, threads, sutures, fibers or the like) that have been interwoven to form a structure having openings. The mesh and/or braid can be composed of metals, polymers, composites, and/or biologic materials. Polymer materials can include Dacron, polyester, polypropylene, nylon, Teflon, polytetrafluoroethylene (PTFE), tetrafluoroethylene, polyethylene terephthalate, polylactic acid (PLA) silicone, polyurethane, polyethylene, polycarbonate, styrene, polyimide, PEBAX, Hytrel, polyvinyl chloride, high-density polyethylene, low-density polyethylene, polyether ether ketone (PEEK), rubber, latex, and/or other suitable polymers known in the art. Other materials known in the art of elastic implants can also be used. Metal materials can include, but are not limited to, nickel-titanium alloys (e.g. Nitinol), platinum, cobalt-chromium alloys, stainless steel, tungsten or titanium, or alloys of any of these metals. In certain embodiments, metal filaments may be highly polished and/or surface treated to further improve their hemocompatibility. The capture portion 200 can be constructed solely from metallic materials without the inclusion of any polymer materials, solely from polymer materials without the inclusion of any metallic materials, or a combination of polymer and metallic materials.

In some embodiments, some or all of the wires of the capture portion 200 are drawn-filled tube ("DFT") wires having a radiopaque core (e.g., platinum, tantalum, gold, tungsten, etc.) surrounded by an elastic or superelastic material (e.g., Nitinol, a cobalt-chromium alloy, etc.). The radiopaque core may comprise about 5% to about 50% (e.g., 10%, 15%, 20%, 25%, 30%, 35%, 40%, 45%) of the total-cross-sectional area of the individual wires. Moreover, some or all of the wires may have a wire diameter of about 0.003 inches to about 0.015 inches (e.g., 0.008 inches, 0.009 inches, 0.01 inches, etc.). In some embodiments, all of the wires have the same diameter, and in other embodiments some of the wires have different diameters.

B. Example Cutting Portions

Figure 17A:
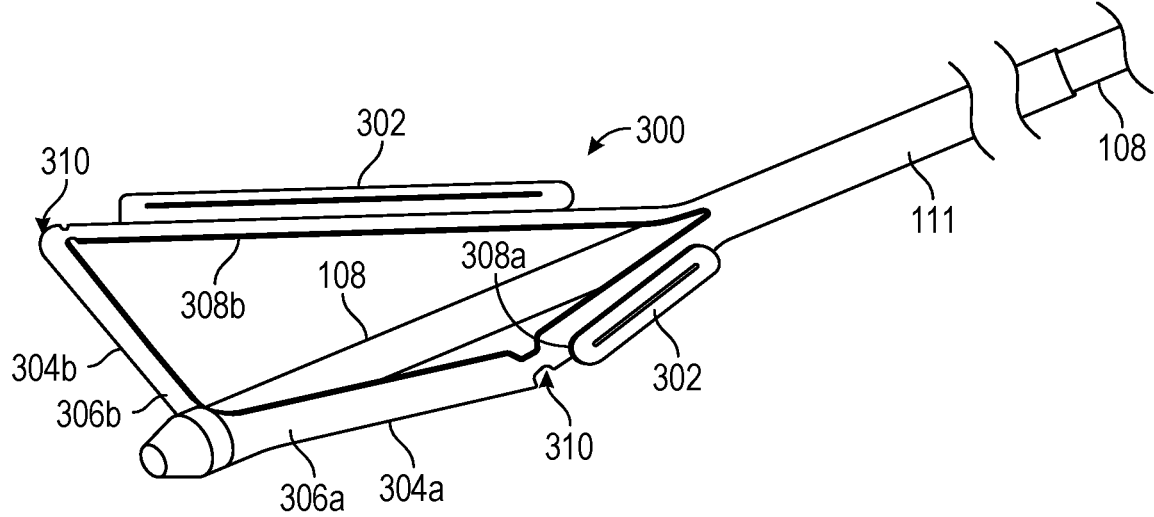
FIG. 17A is an isometric view of a treatment assembly with a cutting portion configured in accordance with the present technology, shown in an expanded state.

According to several embodiments of the present technology, the cutting portion 300 may comprise separate cutting elements, such as blades, attached to an expandable structure forming the cutting portion 300. As described previously, the cutting portion may face proximally or distally as shown in FIGS. 6 and 7 respectively, and also in FIGS. 8 and 9A, respectively. The cutting portion may also be and may be fixed to capture portion as shown in FIGS. 10 and 11. The expandable structure can be configured to angle the cutting elements such that, when the device is pulled towards and then through the obstructive material, the cutting elements cut the obstructive material away from the vessel wall. Continued withdrawal of the device and/or the flow of blood and/or pulling the capture portion through the treatment site then pulls the obstructive material into the capture portion 200. An example of a such an expandable structure is shown in FIG. 17A. Similar to the cutting portion 300 described with respect to FIGS. 3A and 3B, the cutting portion 300 in FIG. 17A can be formed of a tube having two or more longitudinally extending slots that create at least two arms 304 configured to bend radially outwardly when the tube is shortened. The longitudinal slots can be formed such that the arms 304 have joints 310 that bend to form segments 309 in the arms 304 when the arms 304 are expanded.

Figure 17B:
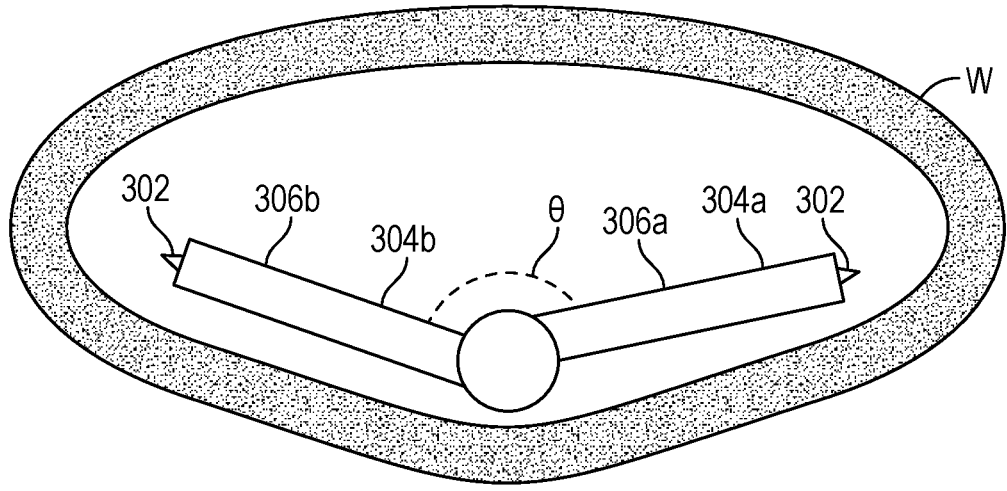
FIG. 17B is an end view of the treatment assembly with a cutting portion shown in FIG. 17A shown positioned within a blood vessel lumen in an expanded state.

As shown in FIG. 17B, the arms 304 of the cutting portion 300 may be canted towards each other (rather than extending 180 degree apart) when expanded so that the arms 304 and attached blades 302 are at an angle θ that better approximates the curvature of the vessel wall W. This geometry facilitates cutting obstructive material (such as chronic thrombus material) away from the curved vessel wall. In some embodiments, the angle between the two arms is less than 180 degrees. In some embodiments, the angle is between 135 and 180 degrees.

Figure 18A:
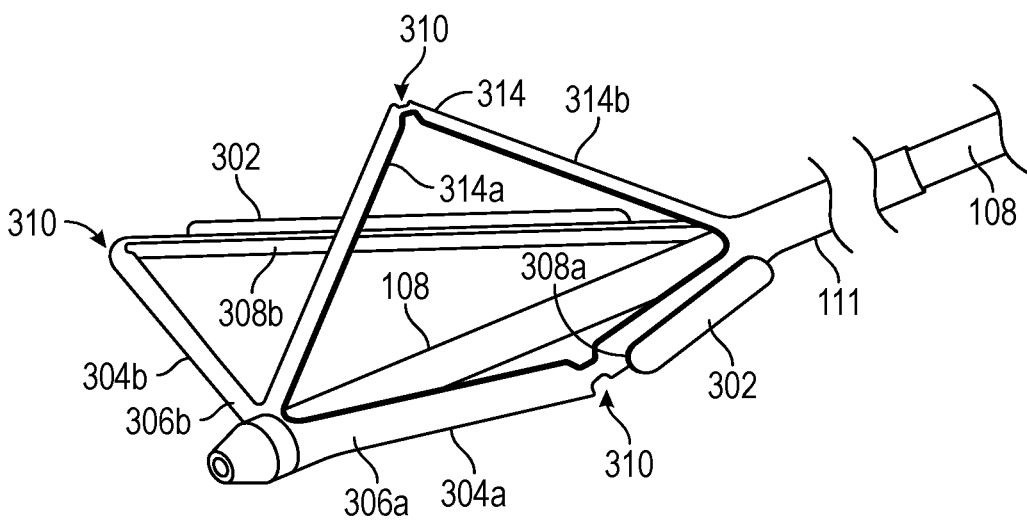
FIG. 18A is an isometric view of a treatment assembly with a cutting portion configured in accordance with the present technology, shown in an expanded state.
Figure 18B:
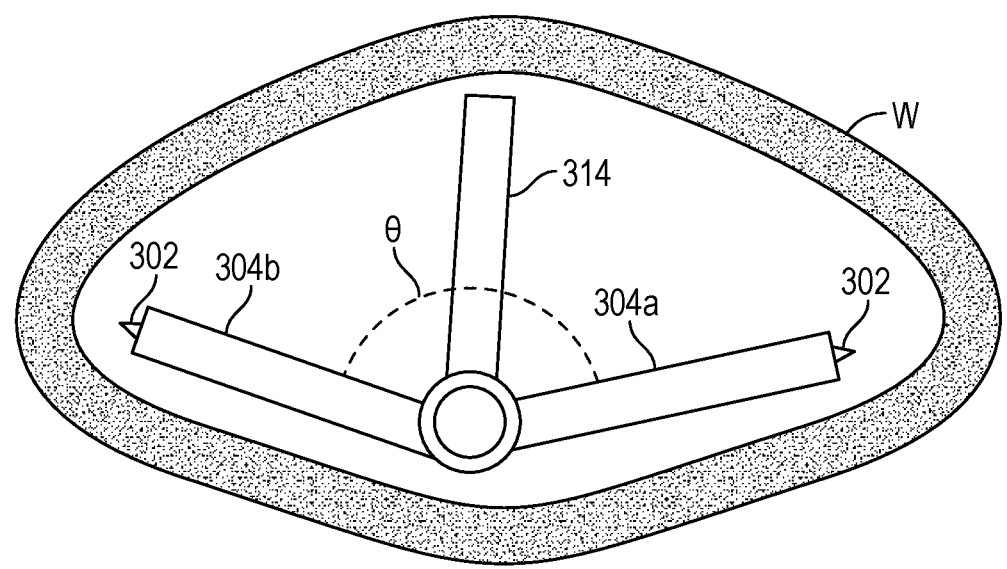
FIG. 18B is an end view of the treatment assembly with a cutting portion shown in FIG. 18A shown positioned within a blood vessel lumen in an expanded state.

As shown in FIG. 18A, in some embodiments the cutting portion 300 can include a positioning arm 314 (e.g., with segments 314a, 314b) disposed circumferentially between the two arms 304 having cutting elements. As depicted in FIG. 18B, when the cutting portion 300 is in an expanded state, the positioning arm 314 pushes against a portion of the vessel wall W opposite the elongated member 102 and improves the position of the cutting elements for cutting and/or separating the obstructive material from the vessel wall W.

Figure 19A:
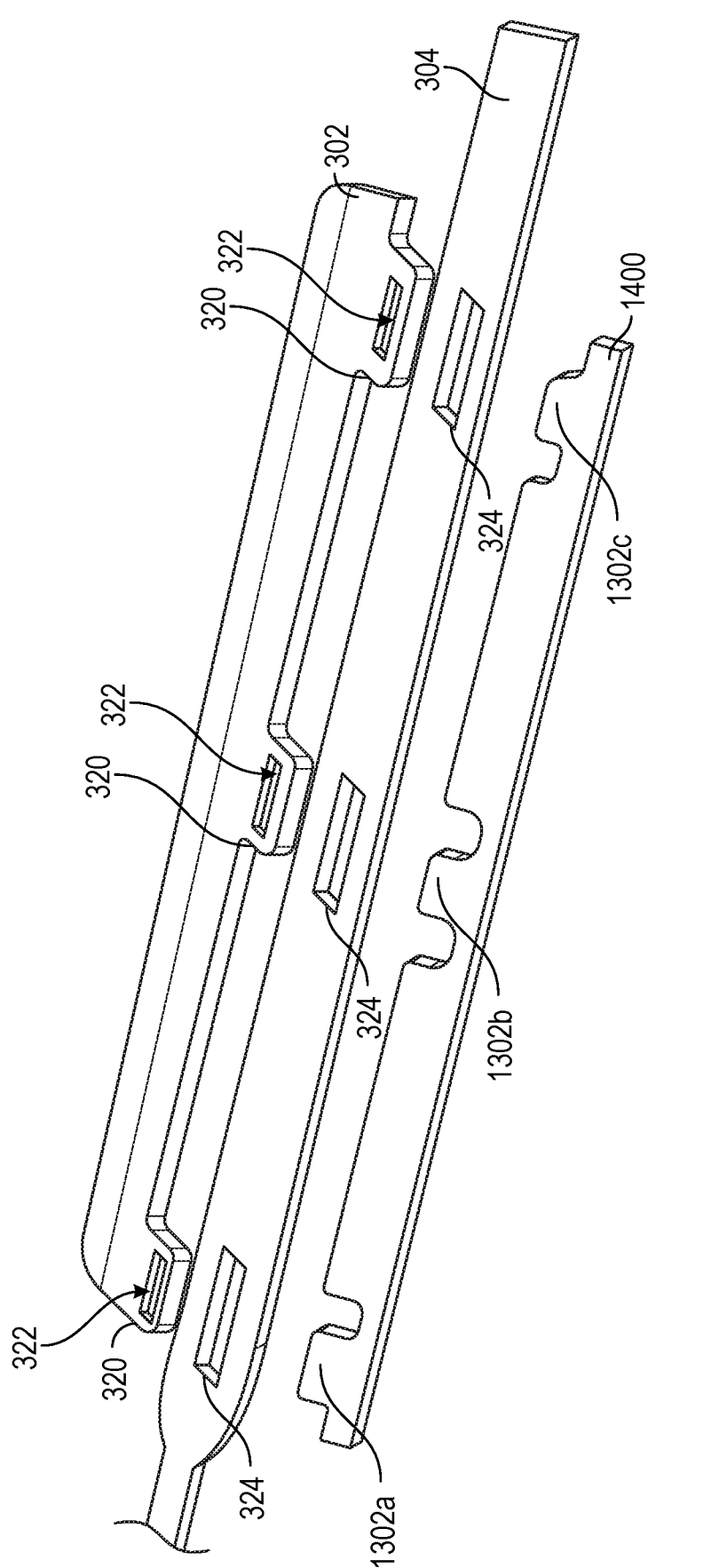
FIG. 19A is an exploded view of a blade assembly configured in accordance with several embodiments of the present technology.
Figure 19B:
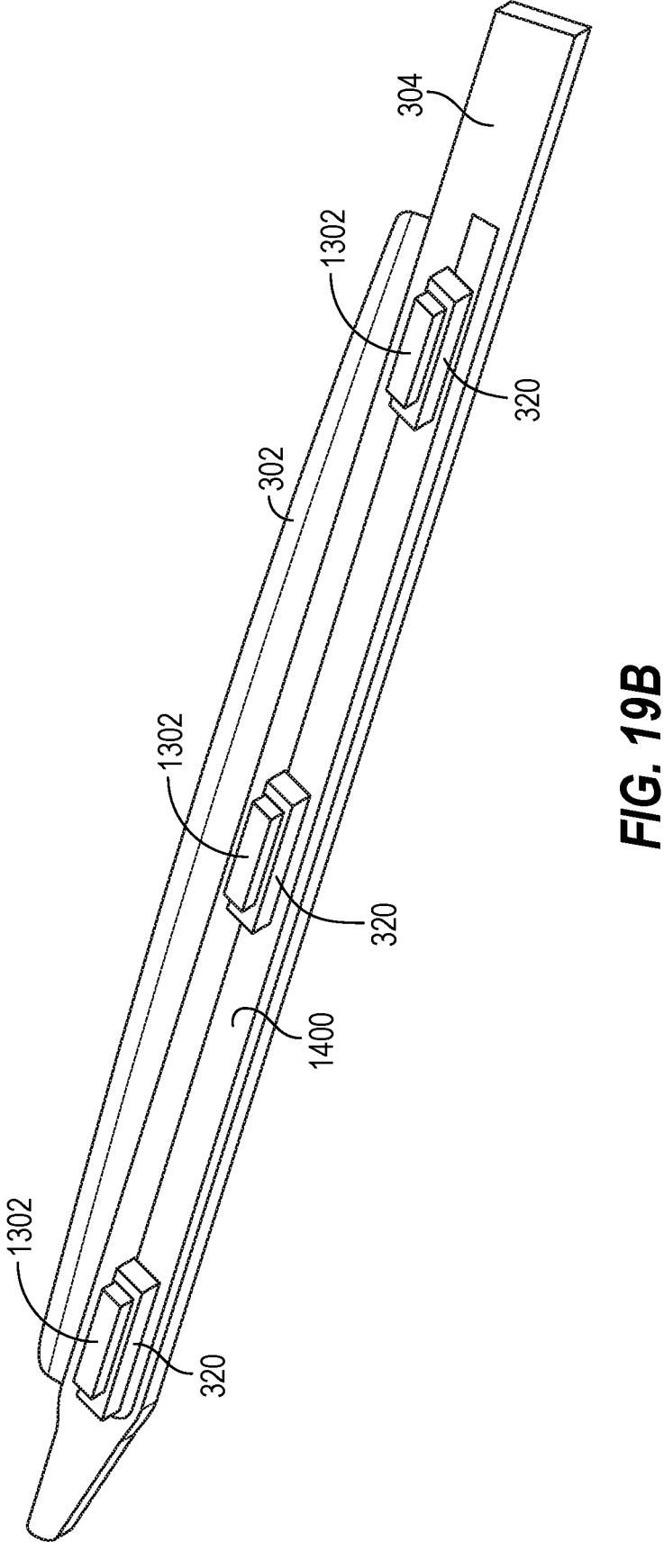
FIG. 19B is an assembled view of a blade assembly configured in accordance with several embodiments of the present technology.

FIGS. 19A and 19B are exploded and assembled views, respectively, of an example blade attachment assembly configured in accordance with several embodiments of the present technology. The assembly includes a portion of an arm 304, for example the distal portion (e.g., distal segments

306a, 306b) or the proximal portion (e.g., proximal segments 308a, 308b) (or other portion of the cutting portion 300 and/or capture portion 200), a blade 302, and a coupler 1400. Any portion of the cutting portions 300 and capture portions 200 described herein can include one or more openings, such as openings 324 shown extending through arm 304. The openings 324 can be configured to receive corresponding tabs 320 extending from the blade 302 in a direction away from the sharpened edge of the blade 302. The tabs 320 can have one or more openings 322 configured to receive corresponding protrusions 1302 (e.g., protrusions 1302a, 1302b, 1302c) positioned along a latch 1400. The tabs 320 on the blades 302 are positioned through the openings 324 on the arm 304 such that the openings 322 on the tabs 320 are exposed on the non-receiving side of the arm openings 324, as shown in FIG. 19B. The protrusions 1302 on the latch 1400 are then positioned through the tab openings 322, thereby locking the blade 302 onto the arm 304. The protrusions 1302 may also include features which allow the width of the protrusion 1302 to be increased and locked after insertion through slots 324, to further secure latch 1400 and blade 302 to arm 304.

Figures 20A, 20B:
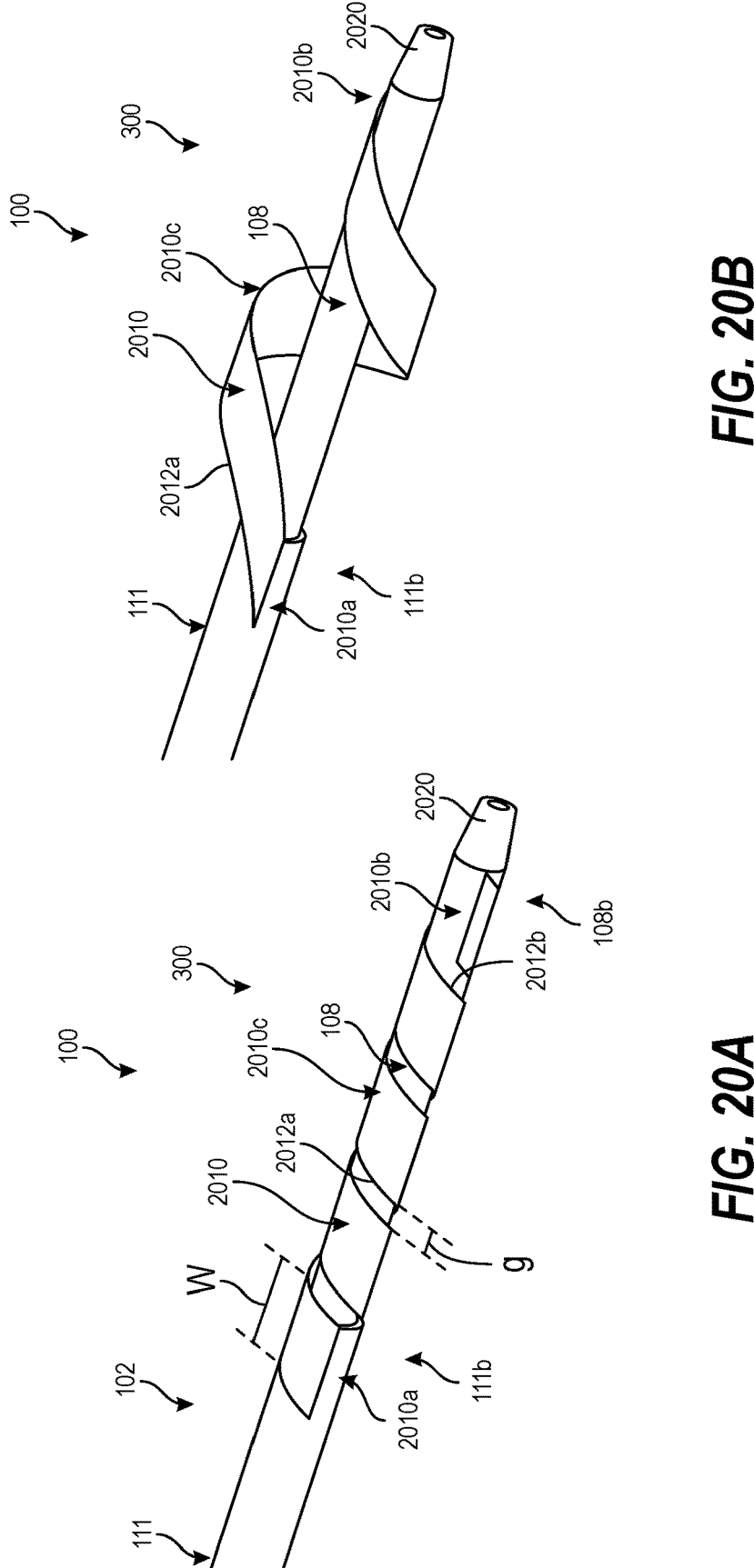
FIGS. 20A and 20B are perspective views of a treatment assembly configured in accordance with several embodiments of the present technology, shown in a collapsed state and an expanded state, respectively.

In some embodiments, as shown in FIGS. 20A and 20B, the treatment assembly 100 includes an elongated shaft 102 comprising first and second elongated members 111, 108 and a cutting portion 300 comprising a cutting element 2010 that extends helically and/or spirally around the longitudinal axis of the elongated shaft 102. The second elongated member 108 can be configured to be positioned within a lumen of the first elongated member 111 and extends distally beyond a distal terminus of the first elongated member 111. In some embodiments the axial positions of the first and second elongated members 111, 108 are fixed, and in some embodiments the first and second elongated members 111, 108 are longitudinally slidably disposed relative to one another. In any case, the first and second elongated members 111, 108 may be configured to rotate relative to one another. The treatment assembly 100 may optionally include a tapered distal tip 2020 at the distal end portion 108b of the second elongated member 108.

The cutting element 2010 can have a proximal end portion 2010a at a distal end portion 111b of the first elongated member 111, a distal end portion 2010b at a distal end portion 108b of the second elongated member 108, and an intermediate portion 2010c extending between the proximal and distal end portions 2010a, 2010b. The intermediate portion 2010c wraps around the longitudinal axis of the treatment assembly 100. The cutting element 2010 is transformable between a collapsed configuration (FIG. 20A) and an expanded configuration (FIG. 20B). In the collapsed configuration, the cutting element 2010 is wound around the second elongated member 108 and has an outer diameter slightly larger than that of the second elongated member 108. The cutting element 2010 may wrap around the longitudinal axis less than one turn (360 degrees) or more than one turn (including multiple turns). When the second elongated member 108 is rotated with respect to the first elongated member 111 (or vice versa) in a first direction, the cutting element 2010 unwinds and expands radially outwardly, as shown in FIG. 20B. Rotation of the second elongated member 108 with respect to the first elongated member 111 (or vice versa) in a second direction opposite the first direction forces the cutting element 2010 to wind down onto the second elongated member 108, thereby radially collapsing the cutting element 2010. The amount of rotation controls the amount of expansion, with the actual expansion percentage depending on, for example, the initial diameter of the elongated shaft 102, the length of the cutting element 2010, and the angle at which the cutting element 2010 couples to elongated shaft 102.

In some embodiments, the cutting element 2010 comprises a ribbon having a width w (labeled in FIG. 20A) and longitudinal sides 2012*a*, 2012*b* (referred to collectively as "longitudinal sides 2012"). The width can be constant along the length of the ribbon or may vary. One of the longitudinal sides 2012 can be proximally facing 2012*a* and one of the longitudinal sides can be distally facing 2012*b*. The ribbon can be made from, for example, one or more resilient and/or superelastic metals or polymers. One or both longitudinal sides 2012 of the ribbon may be configured to cut obstructive material in a vessel lumen. For example, in some embodiments one or both longitudinal sides 2012 of the ribbon are sharpened. Additionally or alternatively, one or both longitudinal sides 2012 of the ribbon may be serrated. One or both longitudinal sides 2010 may have both serrated and sharpened portions to enhance the cutting ability of the cutting element 2010 when moved (e.g., rotated and/or translated) through obstructive material. In some cases it may be beneficial to have the proximally facing longitudinal side 2012*a* sharpened and/or serrated and the distally facing longitudinal side 2012*b* atraumatic and/or rounded. This configuration enables the device to cut through obstructive material when pulled and/or rotated in a proximal direction while reducing the risk of trauma to the vessel wall during advancement of the treatment assembly 100 to a treatment site. According to several embodiments, only the portion of the proximally facing longitudinal side 2012*a* that is proximal of the maximum diameter of the cutting element 2010 (when the cutting element 2010 is in an expanded state) is configured to cut through obstructive material. This configuration can reduce trauma to the native vessel wall as the treatment assembly 100 is pulled proximally and/or rotated through a treatment site.

Once the cutting element 2010 is expanded, the treatment assembly 100 can be rotated, translated, or both in order to cut obstructive material. In some embodiments, expansion of the cutting element 2010 can cut obstructive material. The cutting element 2010 can be repeatedly expanded and collapsed to engage and cut obstructive material. Movement of the cutting element 2010 to cut obstructive material may be performed manually by the user, facilitated by actuators on handle 12, or performed automatically with motors on handle 12.

Figures 21A, 21B:
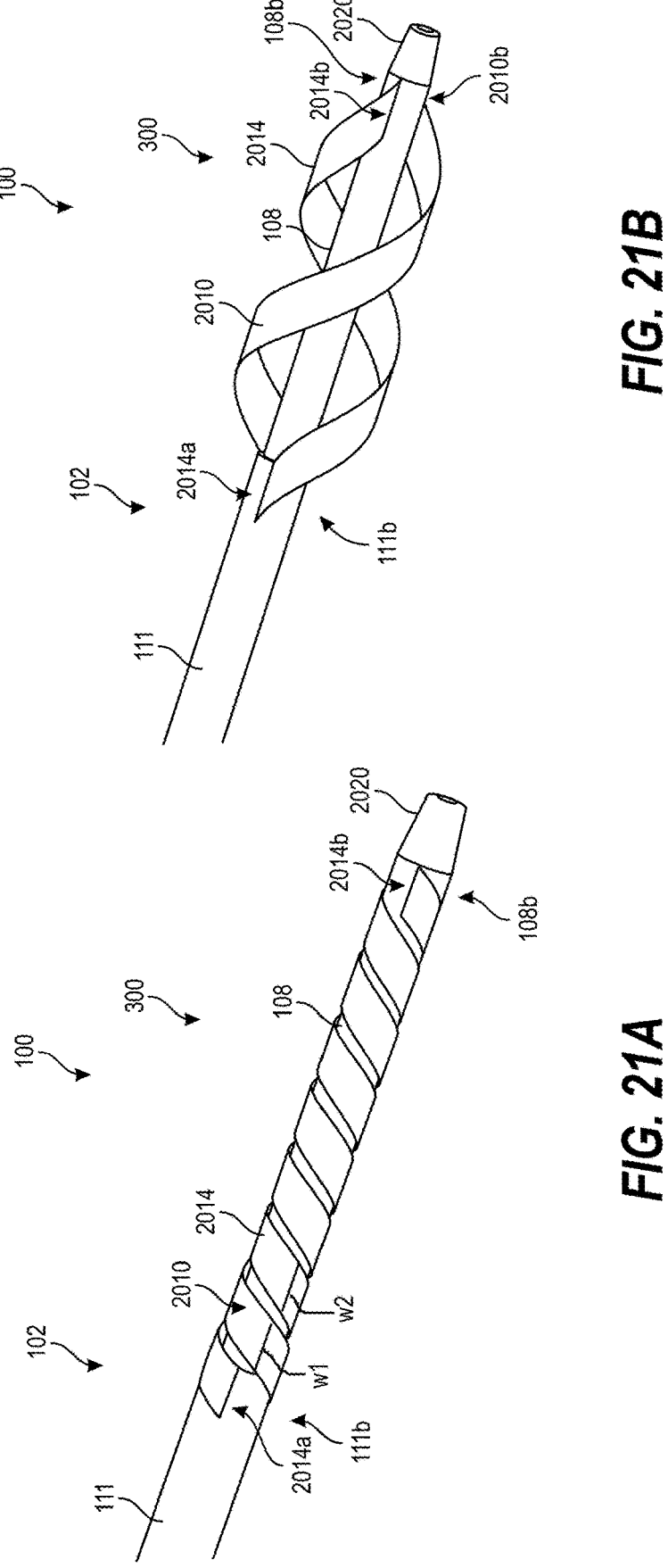
FIGS. 21A and 21B are perspective views of a treatment assembly configured in accordance with several embodiments of the present technology, shown in a collapsed state and an expanded state, respectively.

While only a single cutting element 2010 is shown in FIGS. 20A and 20B, the present technology includes treatment assemblies comprising more than one wrapped cutting element (e.g., two wrapped cutting elements, three wrapped cutting elements, four wrapped cutting elements, etc.). As but one example, FIGS. 21A and 21B show a treatment assembly 100 having first and second cutting elements 2010 and 2014. The treatment assembly 100 is shown in a collapsed state in FIG. 21A and an expanded state in FIG. 21B. Each of the cutting elements 2010, 2014 has a proximal end portion 2010*a*, 2014*a*, respectively (2010*a* not visible in FIGS. 21A and 21B), disposed at the distal end portion 111*b* of the first elongated member 111, and a distal end portion 2010*b*, 2014*b*, respectively, disposed at the distal end portion 108*b* of the second elongated member 108. The proximal end portions 2010*a*, 2014*a* can be coupled to the first elongated member 111 at different circumferential locations that are spaced apart about the circumference of the first elongated member 111. Whether two or more than two cutting elements are utilized, the spacing may be the same between adjacent cutting elements 2010 or may be different.

In some embodiments, the proximal end portions 2010*a*, 2014*a* are coupled to the first elongated member 111 at diametrically opposed locations. In other embodiments, the proximal end portions 2010*a*, 2014*a* have other circumferential spacings. Likewise, the distal end portions 2010*b*, 2014*b* can be coupled to the second elongated member 108 at different circumferential locations that are spaced apart about the circumference of the second elongated member 108. The spacing may be the same between adjacent cutting elements 2010 or may be different. In some embodiments, the distal end portions 2010*b*, 2014*b* are coupled to the second elongated member 108 at diametrically opposed locations. In other embodiments, the distal end portions 2010*b*, 2014*b* have other circumferential spacings. In those embodiments having two or more cutting elements 2010, the different cutting elements 2010 can have the same or different widths.

The diameter of the elongated shaft 102 (and/or one or more components thereof), the number of cutting elements 2010, the angle at which the cutting element 2010 couples to the elongated shaft 102 (and/or one or more components thereof), the number of windings, and the width of the cutting element 2010 may be varied to create a desired expanded cutting configuration. As used herein with respect to the wrapped cutting elements, "length" is measured along the longitudinal axis of the cutting element 2010 which extends through a cross-section of the cutting element 2010. In some embodiments, the elongated shaft 102 is 3 mm in diameter, the length of the cutting element 2010 is 22 mm, the width of the cutting element 2010 is 2 mm, and the cutting element 2010 is coupled to the elongated shaft 102 at an angle of 60 degrees. In the collapsed state, the cutting element 2010 can be tightly wound around the elongated shaft 102 two times. In the expanded state (e.g., after rotation of the second elongated member 108), the cutting element 2010 is unwound until it makes only one turn around the elongated shaft 102, which approximately doubles the maximum diameter of the cutting element 2010 (in this case, to about 6 mm). According to some embodiments, the cutting element 2010 is coupled to the elongated shaft 102 at an angle of 60 degrees, is 33 mm long and wound around the elongated shaft 102 approximately three times. In the expanded state, the cutting element 2010 is unwound until it makes one turn around the elongated shaft 102, which approximately triples the maximum diameter of the cutting element 2010 (in this case, about 9 mm). In some embodiments, the cutting element 2010 has a length of 40 mm, is coupled to the elongated shaft 102 at an angle of 45 degrees, and is wound around the elongated shaft 102 approximately three times. In certain embodiments, the cutting element 2010 has a length of 57 mm, is coupled to the elongated shaft 102 at an angle of 30 degrees, and is wound around the elongated shaft 102 approximately 3 times. In the latter two examples, the cutting element 2010 can be unwound to its fully expanded diameter in which it has one turn and a diameter that is about 3 times its starting diameter (e.g., around 9 mm). However, because the attachment angle is less acute (as compared to the earlier examples), but over a longer length due to the less acute attachment angle. For example, at the 60 degree attachment angle, the helix length is about 16 mm, for the 45 degree attachment angle, the helix length is about 28 mm, and for the 30 degree attachment angle the helix length is 49 mm, all over 3 windings.

The fully expanded diameter of the cutting element 2010 also depends on the design of the attachment of the proximal and distal end portions 2010*a*, 2010*b* of the cutting element

2010 to the first and second elongated members 111, 108, respectively, of the elongated shaft 102. For example, if an end of the cutting element 2010 were fixedly welded or soldered to the corresponding first or second elongated member 111, 108, the cutting element 2010 would remain tangent or near tangent to the elongated shaft 102 as it was unwound, creating one slope angle of helical taper on each end of the cutting element 2010. Whereas, if the cutting element 2010 were allowed to angle away from the elongated shaft 102 to a certain degree or was freely allowed to hinge at the elongated shaft 102, the helical taper would be another slope angle. Each type of helical taper would alter the fully unwound diameter to some extent.

In some embodiments, the width of the cutting element 2010 can be selected based on a desired gap length g (see FIG. 20A) between windings when the cutting element 2010 is fully wound (e.g., in a collapsed state). Additionally or alternatively, the width w (see FIG. 20A) of the cutting element 2010 can depend on how many cutting elements 2010 there are in the treatment assembly 100. If the treatment assembly 100 has more than one cutting element, the width of the individual cutting elements 2010 will be less than if only a single cutting element 2010 were used, over a given length of treatment assembly 100. The greater the width w of a given cutting element 2010, the more resistance it will have to bending distortion when under load, and the more effectively it can cut obstructive material. As demonstrated, there are trade-offs between the number of cutting elements 2010 and performance of each cutting element 2010. In some embodiments, the width w of cutting element 2010 may vary over the length of the cutting element. For example the width w may be smaller at the ends 2010a and 2010b but be wider at intermediate portion 2010c. Additionally or alternatively, the widths of multiple cutting elements may be varied, for example with reference to FIGS. 21A and 21B, the cutting element 2010 may have a width w1 and cutting element 2014 may have a second width w2.

As discussed, the second elongated member 108 may rotate with respect to the first elongated member 111 when expanding the treatment assembly 100, and in some embodiments the second elongated member 108 may also translate with respect to the first elongated member 111 to axially compress or elongate the cutting element 2010. The ability of the cutting element 2010 to be axially compressed or elongated depends in part on how the proximal and distal end portions 2010a, 2010b of the cutting element 2010 are coupled to the first and second elongated members 111, 108 of the elongated shaft 102, and whether the attachment enables the attachment angle to vary, as axial compression or elongation of the cutting element 2010 increases or decreases the angle of attachment. The ability to axially compress and elongate the cutting element 2010 while in the expanded state improves the cutting efficiency of the treatment assembly 100. For example, the treatment assembly 100 may separate and capture obstructive material from a combination of one or more expanded wrapped cutting elements rotating, translating, expanding, and/or compressing through obstructive material of a treatment site. Additionally, the cutting element 2010 may be partially unwound for a first cutting pass, and then further unwound to a more expanded and/or fully expanded state for a second cutting pass, and so forth for multiple cutting passes until the desired effect is achieved.

In some variations, the cutting element 2010 is integral to the first elongated member 111. For example, the first elongated member 111 can comprise a tubular member that has been cut in a helical and/or spiral pattern at its distal portion to create one or more helical strips. As such, the first elongated member 111 and the cutting element 2010 can comprise the same material. The distal end portion 2010b of the cutting element 2010/distal end portion 111b of the first elongated member 111 can be fixed to the distal end portion 108b of the second elongated member 108. When the second elongated member 108 is rotated with respect to the first elongated member 111, the cut strip (now the cutting element 2010) is unwound and expands outward. The foregoing embodiments advantageously do not require any attachment design and therefore reduce the number of manufacturing processes.

In another variation, the cutting element 2010 is formed from one material that has the required mechanical properties including the ability to be wound and unwound, sharpened, and hold sufficient rigidity to have an effective cutting action when manipulated as described above, and the first elongated member 111 is formed from a separate tube. The first elongated member 111 is then attached to a second tube that extends proximally from the treatment assembly 100 and that has suitable properties for a catheter shaft component, for example cost, flexibility, etc.

There are many possible methods to attach the proximal end portion 2010a of the cutting element 2010 to the first elongated member 111 and the distal end portion 2010b to the second elongated member 108, for example via soldering, welding, gluing, mechanical attachment, or some combination thereof. As noted above, the method of attachment can affect the specific expansion performance and strength of attachment of the cutting element 2010 when it is expanded and used to remove obstructive material.

Figures 22A, 22B, 22C:
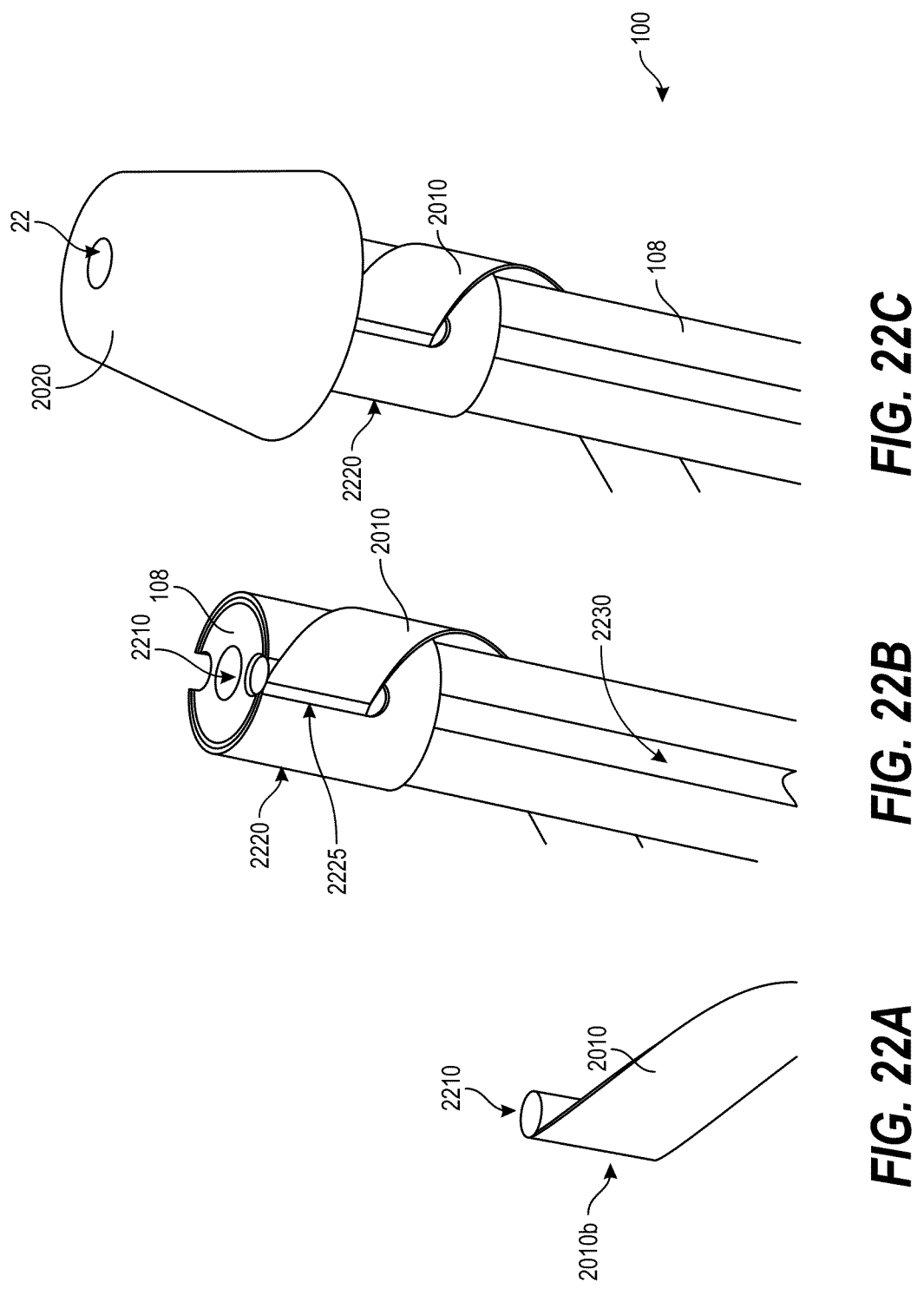
FIGS. 22A, 22B, and 22C are perspective views of a treatment assembly configured in accordance with several embodiments of the present technology, shown with various components removed for ease of explanation.

In some embodiments, for example as shown in FIGS. 22A, 22B, and 22C, the distal end portion 2010b of the cutting element 2010 is mechanically captured between the distal end portion of the second elongated member 108 and a securing element 2220. The distal end portion 2010b of the cutting element 2010 can be coupled to a cylindrical coupler 2210 (e.g., a dowel, a tube, or other cylindrical component) and extend from the coupler 2210 at an angle. The angle between the coupler 2210 and the cutting element 2010 forms the angle at which the cutting element 2010 extends from the second elongated member 108. In some embodiments, the coupler 2210 is integral with the cutting element 2010. For example, the coupler 2210 can be constructed by rolling the cutting element 2010 into a tight cylinder at the distal end portion 2010b. In some embodiments, the coupler 2210 is a separate component that is attached to the distal end portion 2010b of the cutting element 2010. In any case, the coupler 2210 can be configured to be received within a groove 2230 extending along a distal portion of the second elongated member 108. The securing element 2220 can be a band that is configured to be slidably disposed over the outer surface of the second elongated member 108. The securing element 2220 can have a slot 2225 extending along less than its entire length. The slot 2225 can be continuous with an opening at a distal end of the securing element 2220.

As shown in FIG. 22B, the cutting element 2010 can be mechanically captured at the distal end portion of the second elongated member 108 by inserting the coupler 2210 into the groove 2230 in the second elongated member 108, and sliding the securing element 2220 upward to capture the coupler 2210 within the slot 2225. The slot 2225 in the securing element 2220 can be wide enough to allow the cutting element 2010 to extend radially outwardly therethrough, but too narrow to allow passage of the coupler 2210. The coupler 2210 is configured to rotate within the groove 2230, thereby allowing the extension angle of the cutting element 2010 (relative to the second elongated member 108) to vary. The width of the slot 2225 may be varied to allow a varied range of motion of the coupler 2210 (and thus the cutting element 2010) in the groove 2230 when the treatment assembly 100 is expanded. In FIG. 22C the groove 2230 is shown extending proximally beyond the securing element 2220, but in other embodiments the groove 2230 may terminate at more distal locations (including aligned with or distal to a proximal terminus of the securing element 2220). In some embodiments, the coupler 2210 is fixed within the groove 2230 such that it cannot rotate relative to the second elongated member 108.

The second elongated member 108 can have a tapered distal tip 2020 at its distal end. The tapered distal tip 2020 is removed from view in FIG. 22B to show the coupler 2210 in the groove 2230, but shown in FIG. 22C to illustrate how the coupler 2210 and cutting element 2010 are mechanically captured. The distal tip 2020 can prevent distal axial movement of the securing element 2220 and the coupler 2210, thereby securing the coupler 2210 within the slot 2225 in the securing element 2220. In some embodiments, the distal tip 2020 has a maximum diameter that is greater than the diameter of the second elongated member 108. In some embodiments, the coupler 2210 is secured within the slot 2225 via other means, such as a non-tapered distal cap, tube, or other component to prevent securing element from sliding out of the slot 2225. In these and any embodiments disclosed herein, the second elongated member 108 can have a lumen 22 extending therethrough. The distal tip 2020 can also include a lumen that is an extension of lumen 22. The lumen 22 may be used to accommodate a guidewire or other guide element (for example the shaft of a separate capture element component) to allow advancement and positioning of the treatment assembly 100 at the treatment site.

The securing element 2220 and/or second elongated member 108 can include one or more securing means so that when the securing element 2220 is in position over the coupler 2210, the axial and rotational position of the securing element 2220 (and thus axial position of the coupler 2210) is fixed relative to the second elongated member 108. For example, the securing element 2220 may have one or more side holes (not shown) and the second elongated member 108 may have one or more protrusions that spring radially outwardly into the side holes when the side holes are aligned with the protrusions. In some embodiments, the securing element 2220 includes one or more tabs (not shown) which can be pushed radially inward to lock into one or more receptacles in the second elongated member 108. Additionally or alternatively, the securing element 2220 can be soldered, welded, or glued to the second elongated member 108 to hold the securing element 2220 in place.

The proximal end portion 2010_a_ of the cutting element 2010 may be mechanically captured at a distal portion of the first elongated member 111. For example, the first elongated member 111 may include a groove similar to the slot 2225 on the securing element 2220. In such embodiments, the second elongated member 108 can have a recess in its outer surface so that the second elongated member 108 can rotate freely with respect to the first elongated member 111 to expand and collapse the cutting element(s) 2010. As previously mentioned, in some embodiments the cutting element 2010 is integral with and an extension of the first elongated member 111.

The coupler 2210 can have other shapes and configurations. For example, in some embodiments the distal end portion 2010_b_ of the cutting element 2010 may be cut (e.g., laser cut) to have a T-shaped distal end that is configured to be received within the slit 2225 of the securing element 2220. The T-shaped distal end (or portion thereof) is then trapped in place between the securing element 2220 and the second elongated member 108. The treatment assembly 100 can include a distal tip to secure the T-shaped distal end in place.

In any of the embodiments including one or more cutting elements 2010, the treatment assembly 100 may optionally include an expandable member (e.g., a balloon) (not shown) disposed radially inwardly of the cutting element 2010. The expandable member can be configured to be expanded underneath the already-expanded (partially or completely) cutting element 2010 to add radial force to the cutting element 2010 and prevent or reduce distortion of the cutting element 2010 as the treatment assembly 100 is translated and/or rotated through the treatment site. The expandable member may be aligned with only the intermediate and/or distal portions of the cutting element 2010 (i.e., and not the proximal portion), so as not to interfere with the cutting action of the cutting element 2010 on the proximal aspect of the treatment assembly 100.

Figures 23A, 23B:
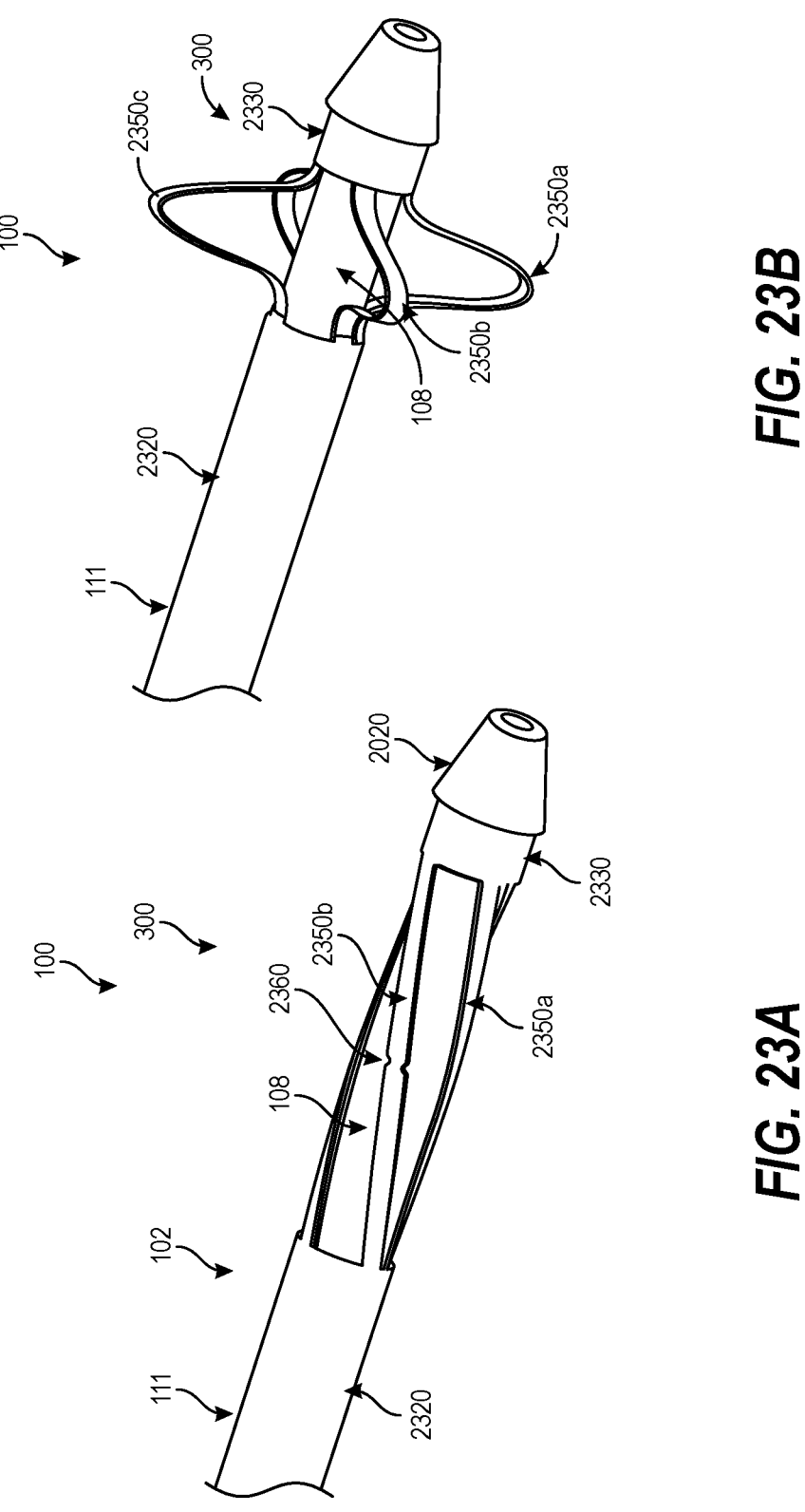
FIGS. 23A and 23B perspective views of a treatment assembly configured in accordance with several embodiments of the present technology, shown in a collapsed state and an expanded state, respectively.

In some embodiments, for example as shown in FIGS. 23A and 23B, the treatment device includes an elongated shaft 102 comprising first and second elongated members 111, 108 and a cutting portion 300. The distal portion of the first elongated member 111 comprises an elongated tube 2320, a distal band 2330, and two or more strips 2350 (e.g., strips 2350_a_, 2350_b_, 2350_c_) connecting the proximal tube 2320 to the distal band 2330. In a collapsed state, the strips 2350 may be parallel to the axis of the elongated shaft 102, or may be at a slight angle (e.g., between 0 and 20 degrees) from the axis of elongated shaft 102 (as shown in FIG. 23A). The second elongated member 108 can be configured to be slidably disposed within a lumen of the first elongated member 111. The second elongated member 108 can extend through the proximal tube 2320 and the portion underlying the strips 2350, and distally beyond the distal band 2330. The treatment assembly 100 can comprise a distal tip 2020 coupled to the distal end of the second elongated member 108 and which has a maximum diameter larger than the diameter of the distal band 2330. In some embodiments, the distal tip 2020 is locked to the distal band 2330 of the first elongated member 111 by means of locking elements on the second elongated member 108 and distal band 2330. For example, the distal band 2330 can have side holes and the second elongated member 108 may have protrusions that spring outwards into the side holes. In some embodiments, the distal band 2330 has tabs which can be pushed radially inward to lock into receptacles in the second elongated member 108. Additionally or alternatively, the second elongated member 108 and distal band 2330 can be attached, for example, via welding, glue, or soldering.

In any case, when the second elongated member 108 is pulled proximally, the distance between the distal band 2330 and the distal end of the proximal tube 2320 shortens and the strips 2350 on the first elongated member 111 bow radially outwardly to form expanded arms, as shown in FIG. 23B. In those embodiments where the strips 2350 are attached to the first elongated member 111 at an angle (as shown in FIGS. 23A and 23B), the arms are somewhat twisted in the plane perpendicular to the elongated shaft 102. The strips 2350 might have one or more edges that are sharpened and/or serrated. When expanded, the treatment assembly 100 may be rotated and/or translated to act as rotary blades to remove obstructive material from the treatment site. The amount of expansion depends on the amount of translation of the second elongated member 108 relative to the first elongated member 111. In use, the arms may be partially extended outwards for a first pass, and then further expanded for a second pass, etc., to remove obstructive material more effectively.

Figure 24:
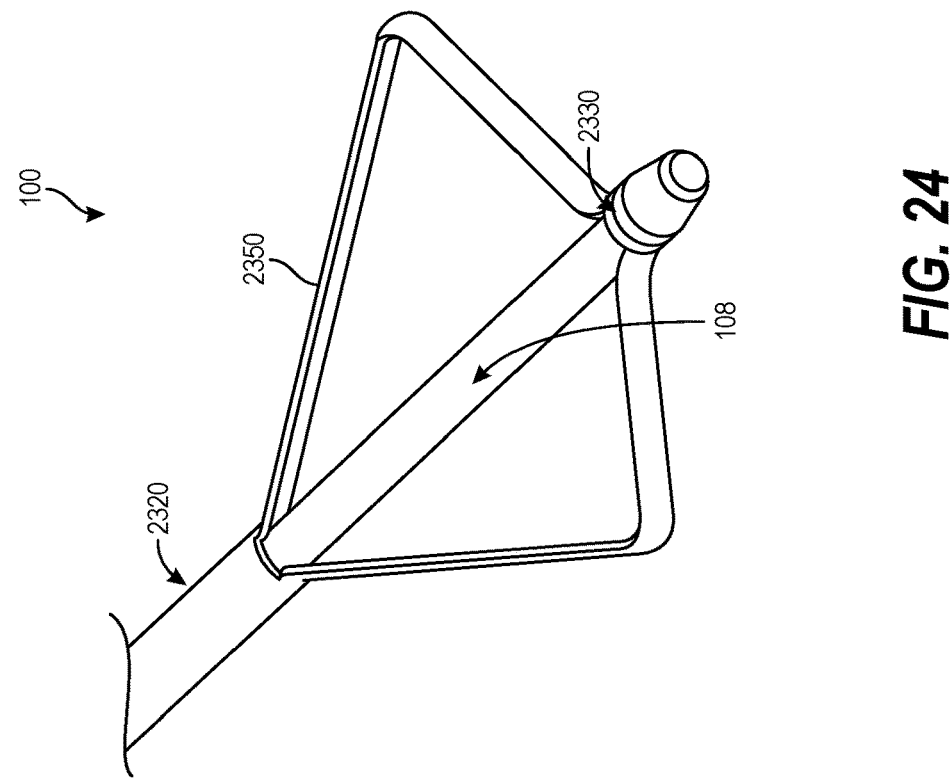
FIG. 24 is a perspective view of a treatment assembly configured in accordance with several embodiments of the present technology, shown in an expanded state.

The strips 2350 may be integral to the tube 2320 of first elongated member 111. As seen in FIG. 23A, the first elongated member 111 can be cut (e.g., laser cut) at the distal end to create one or more strips, parallel to or at a slight angle to the axis of the elongated shaft 102. Optionally the cut pattern includes recessed portions 2360 along the length of one, some, or all of the strips 2350 to urge the strip 2350 to preferentially bend at the recessed portions 2360. The recessed portions 2360 may be at the midpoint of the strip 2350, to create a symmetric expanded geometry, or may be biased towards the distal end of the strip 2350 to create an asymmetrical expanded geometry, as illustrated in FIG. 24. The latter configuration may allow for a better cutting angle of the strip cutting edge against the obstructive material.

Figure 25:
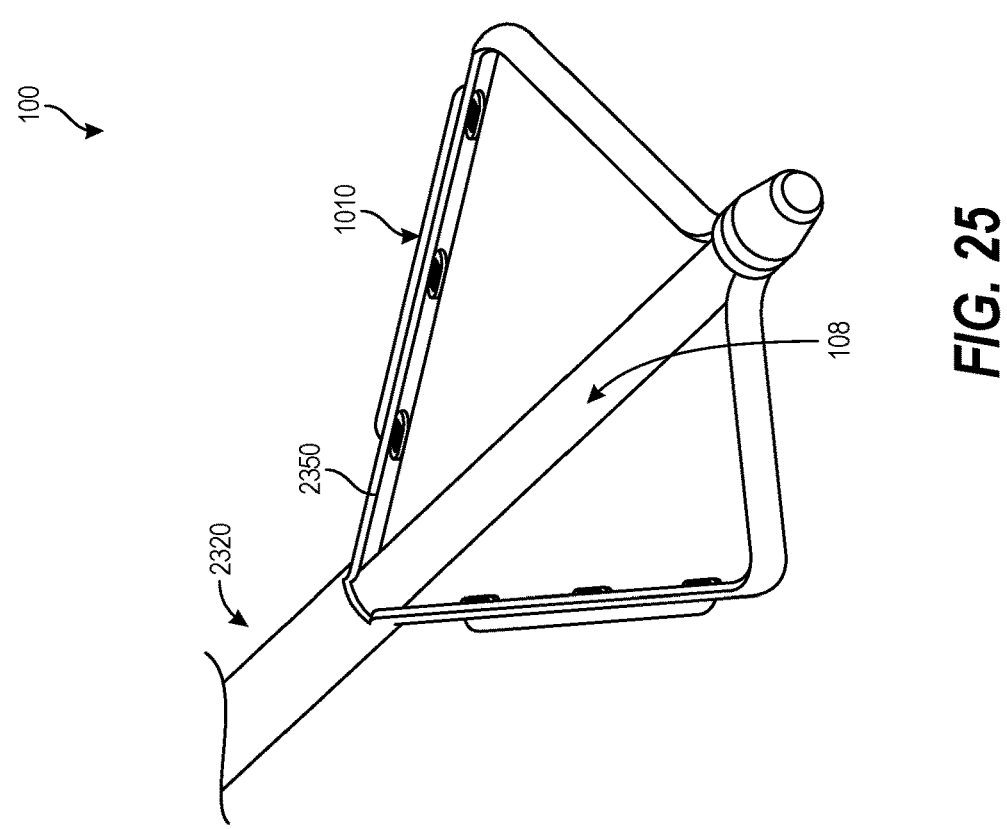
FIG. 25 is a perspective view of a treatment assembly with a cutting portion configured in accordance with several embodiments of the present technology, shown in an expanded state.

In some embodiments, the strips 2350 are not the cutting element. Instead, as seen in FIG. 25, the strips 2350 contain tabs or other features that allow a second cutting element, such as a blade 1010, to be attached to each strip 2350. In this variation, the first elongated member 111 may be made from one material that is configured to be expanded and collapsed, and the blade 1010 may be made from a second material that is suited to have a sharpened blade edge. The blade 1010 may be secured to strips 2350 by means of a separate latch component (not shown). Additionally or alternatively, the blade 1010 may be soldered or welded to the strip 2350.

Figure 26:
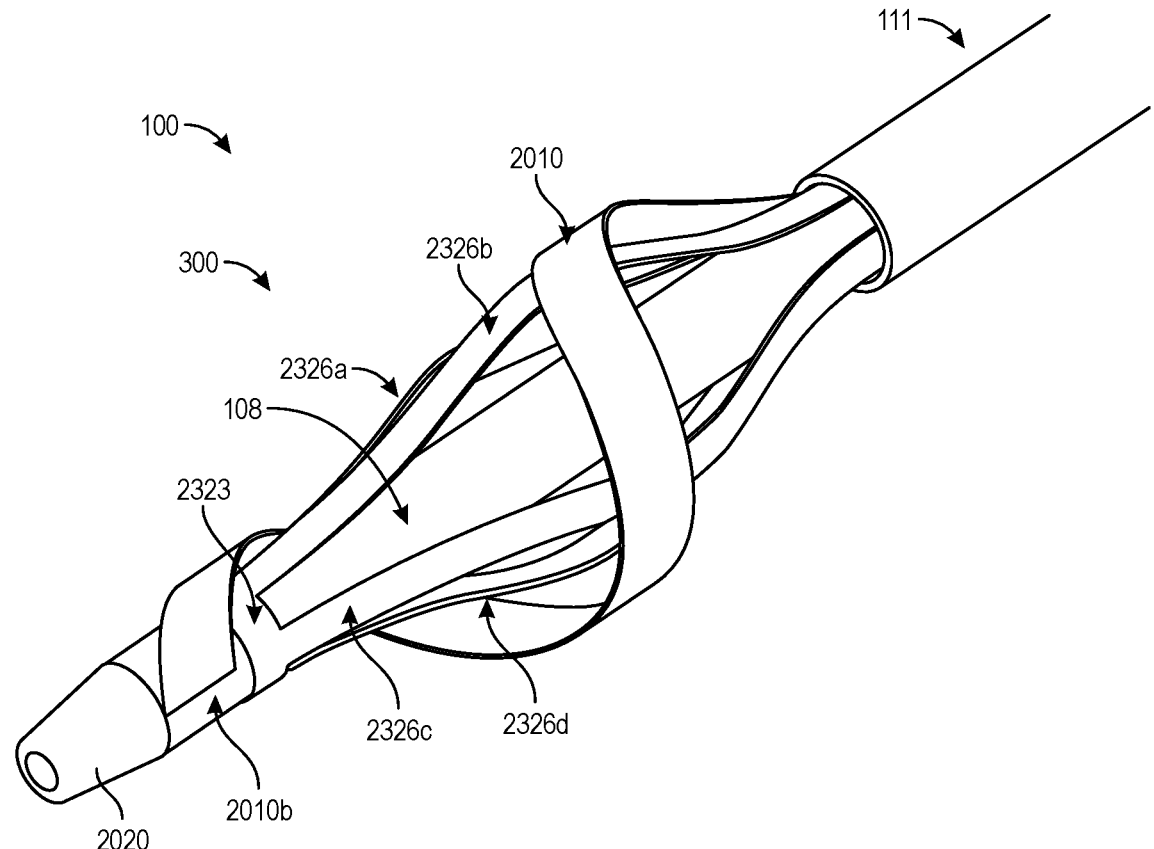
FIG. 26 is a perspective view of a treatment assembly configured in accordance with several embodiments of the present technology.

In some instances, it may be desirable to have an additional cutting element orientated in the opposite direction of the existing cutting element to provide a counterforce during cutting of obstructive material. For example, in some embodiments the device may include one or more inner cutting elements positioned inside one or more outer cutting elements. The inner cutting elements can be substantially linear (for example as shown in FIG. 23) or may be helical and/or spiral (for example as shown in FIGS. 20A and 20B). The outer cutting elements can be substantially linear (for example as shown in FIG. 23) or may be helical and/or spiral (for example as shown in FIGS. 20A and 20B). In some embodiments, the device 101 may comprise an inner elongated member 108, an outer elongated member 111 with one or more cutting element(s) 2010, and an elongated member located between the inner and outer elongated members 108, 111 that comprises one or more cutting elements. In such embodiments, the cutting elements can be integral to the outer and intermediate elongated members, or may be separate elements attached to the outer and intermediate elongated members. The handle 12 of the device 101 (FIG. 1) may have an actuator that controls the rotational movement of the outer and middle elongated members. For example, an actuator(s) on the handle 12 may be configured to turn the first elongated member 111 in one direction while either keeping the inner cutting element (carried by the intermediate elongated member) stationary or rotating the inner cutting element in the opposite direction. In some embodiments, for example as shown in FIG. 26, a cutting portion 300 of the treatment assembly 100 comprises an inner elongated member 108, an outer elongated member 111 with one or more attached or integral cutting elements 2010, and an intermediate member 2323 located between the inner elongated member 108 and the outer elongated member 111, with corresponding cutting elements 2326 (labeled individually in FIG. 26 as 2326a-2326d). In such embodiments, the handle 12 (FIG. 1) can include one or more actuators to rotate the outer elongated member 111 in one direction with respect to the inner elongated member 108 while shortening the intermediate elongated member 2323 to expand the cutting elements 2326 radially outwardly during deployment. The handle 12 can be configured to further actuate the outer and intermediate elongated members 111, 2326 to rotate and/or translate to cut the obstructive material. One, some, or all of the cutting elements 2010 can have a sharpened edge, and one, some, or all of the cutting elements 2326 can have a sharpened edge. In some embodiments, only the outer cutting elements 2010 or only the inner cutting elements 2326 may have a sharpened edge. In those embodiments including inner and outer cutting element(s) with sharpened edges, the sharpened edges can be configured to face each other. As such, the inner and outer cutting elements 2326, 2010 can be configured to trap obstructive material as they move towards one another to cut the obstructive material. The inner and outer cutting elements 2326, 2010 can thus provide a counterforce to the cutting force (or any force) exerted on the obstructive material by the other.

In a similar fashion, the embodiment shown in FIGS. 23A and 23B could have one or more expandable cutting elements located inside the outer cutting elements. The treatment assembly 100 can have an intermediate elongated member located between the inner elongated member 108 and the outer elongated member 111, with corresponding expandable cutting elements. The inner and outer cutting elements could be configured such that when expanded, the cutting edges of the inner cutting elements are canted in one direction and the cutting edges of the outer cutting elements are canted in the opposite direction. As above, the handle 12 can have an actuator that controls the rotational movement of the outer and intermediate elongated members. For example, the handle 12 may be configured to turn the outer elongated member 111 in one direction while either keeping the intermediate member stationary or rotating the intermediate member in the opposite direction.

Figure 27A:
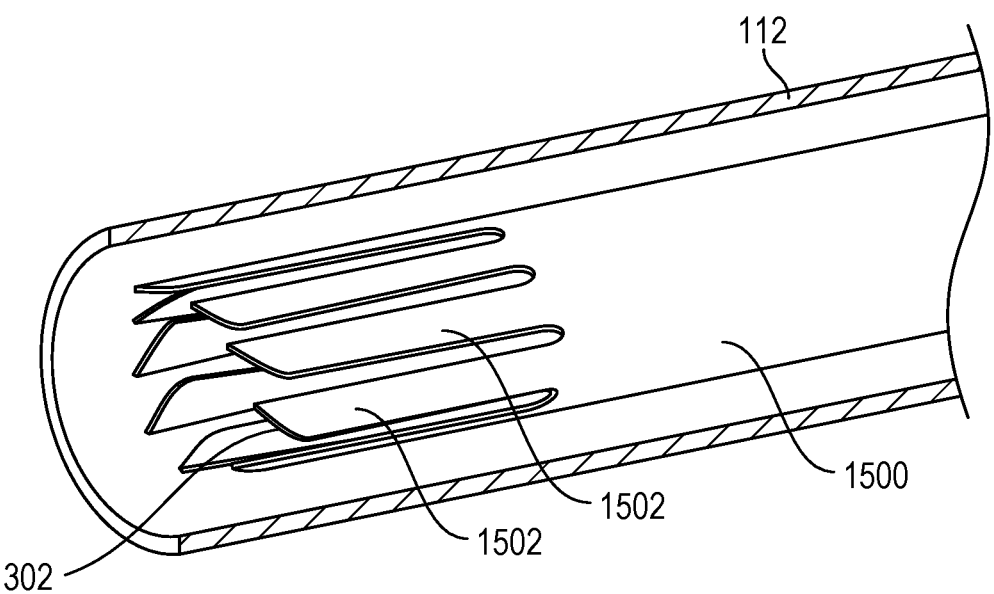
FIGS. 27A and 27B are isometric views of a treatment assembly with cutting portion configured in accordance with several embodiments of the present technology.
Figure 27B:
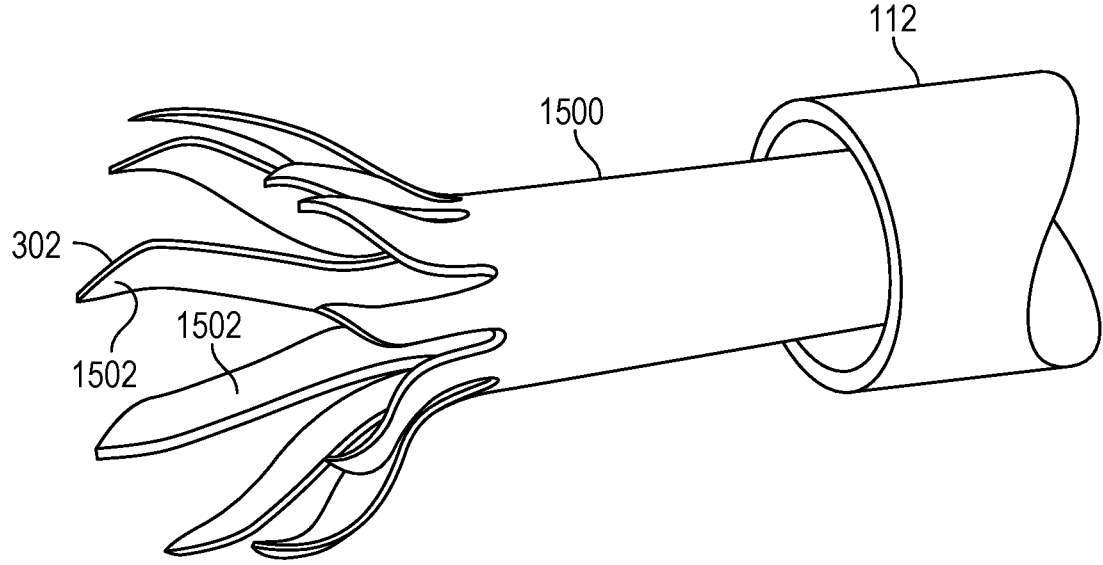
Figure 27C:
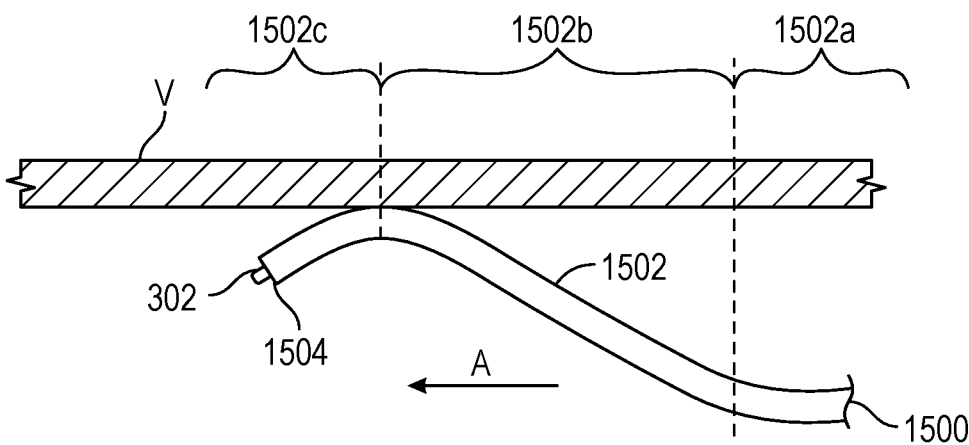
FIGS. 27C and 27D are side views of an arm of the cutting portion shown in FIGS. 27A and 27B, shown isolated from the treatment assembly and configured in accordance with several embodiments of the present technology.
Figure 27D:
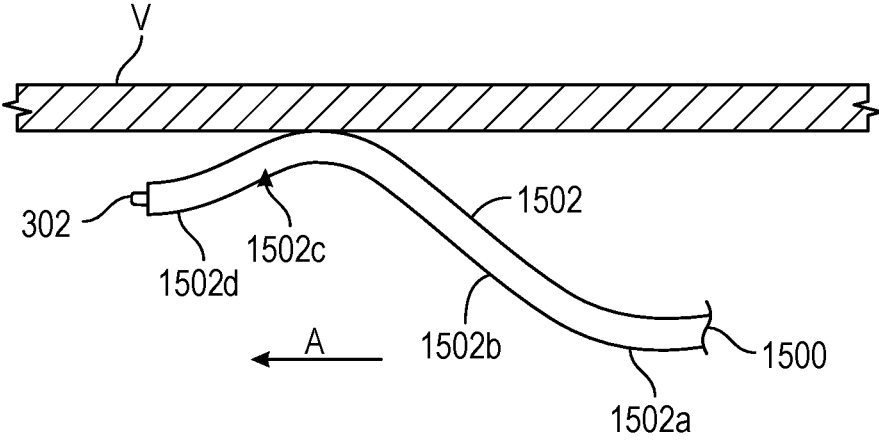

In some embodiments, the cutting portion 300 can be configured as provided in FIGS. 27A-27D. In such embodiments, the cutting portion 300 can be made from a superelastic tube 1500 such as nitinol or others, with a cut pattern that forms multiple (2 or more) arms 1502 protruding from the distal end of the nitinol tube. The arms 1502 can be heat-set to expand outward in a larger diameter than the base tube once a sleeve 112 is retracted. One, some, or all of the arms 1502 can be shape set to assume the shape shown in the side views of FIGS. 27C and 27D. As shown in FIG. 27C, the arm 1502 can have a first substantially linear portion 1502a extending from the tube, a second portion 1502b extending distally and radially outwardly from the first portion 1502a, and a third, distal-most portion 1502c extending distally and radially inwardly from the second portion 1502b. The curve between the second and third portions 1502b, 1502c forms an atraumatic surface that can slide along the vessel wall. In such embodiments, the cutting element 302 can project distally from the distal terminus 1504 of the arm 1502 and along a dimension that is substantially parallel to the vessel axis and along the direction of movement of the arm 1502 (indicated by arrow A). In some embodiments, for example as represented by FIG. 27D, one, some, or all of the arms 1502 include a fourth portion 1502d extending distally from the third portion 1502c along a dimension that is substantially parallel to the vessel axis and along the direction of movement of the arm 1502 (indicated by arrow A).

One, some, or all of the arms 1502 can have a beveled and sharpened point. Like the cutting portion 300 in FIGS. 8-9B, the cutting portions in the embodiments represented by FIGS. 27A-27D form a circumferential pattern, although since the blades do not overlap in the collapsed configuration, the cuts will not be as close together. However, because they are not required to overlap in the collapsed configuration, the collapsed profile takes up less space, which can be advantageous for an endovascular device.

Figure 28A:
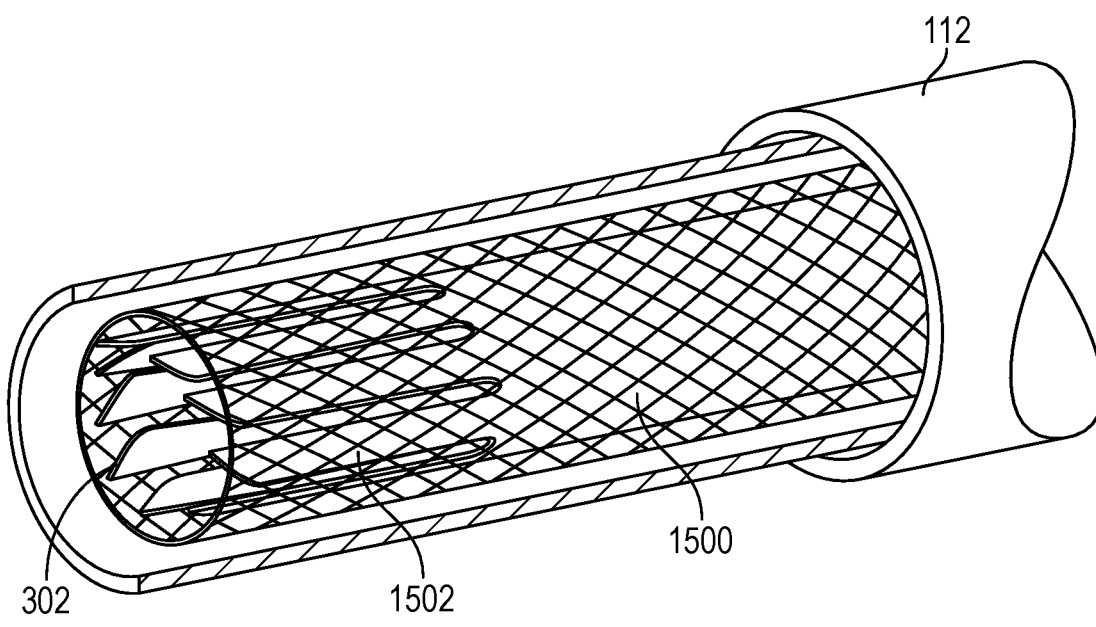
FIGS. 28A and 28B are isometric views of a treatment assembly with cutting portion configured in accordance with several embodiments of the present technology.
Figure 28B:
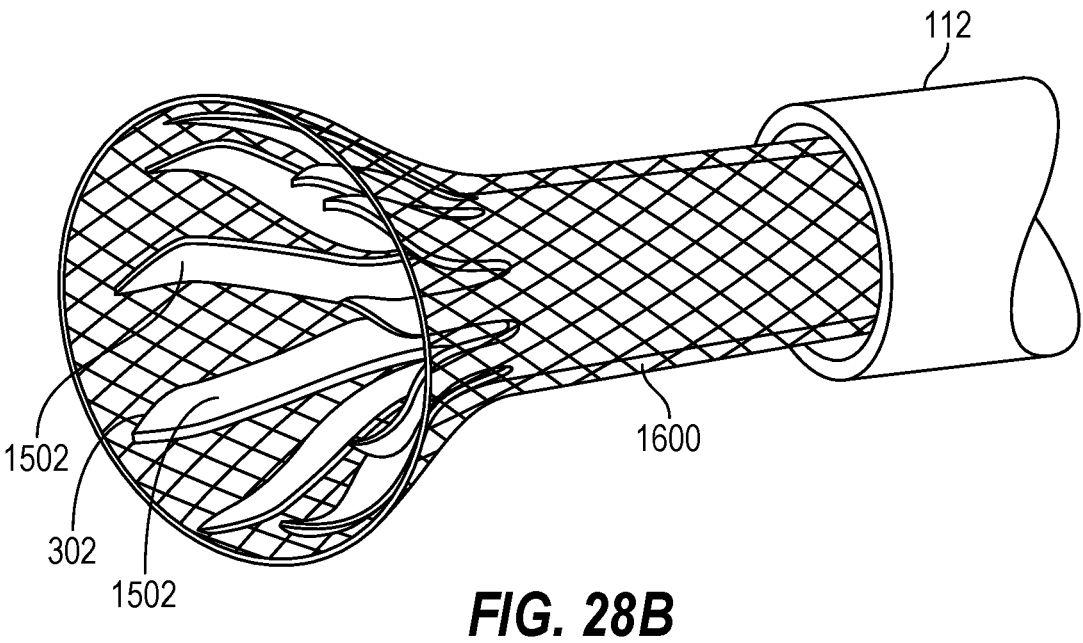

FIGS. 28A and 28B are isometric views of a cutting portion configured in accordance with several embodiments of the present technology. FIG. 28A shows the cutting portion in a collapsed state. FIG. 28B shows the cutting portion in an expanded state. The system 10 and/or assembly 100 of FIGS. 28A and 28B can be generally similar to the system 10 and/or assembly 100 of FIGS. 27A-27D, except in FIGS. 28A and 28B, the system 10 includes a cover 1600 positioned over all or a portion of the cutting portion 300. The cover 1600 can be a braid, a weave, a fabric, a polymer material, etc. The cover 1600 can protect the native vessel wall from the cutting portions while allowing the cutting portion to remove obstructive material in the lumen of the treatment site. The cover 1600 may also aid in capturing separated obstruction material instead of or in addition to the use of a capture device 200 and/or aspiration via suction source 18.

The cover 1600 may also be applied to other cutting portions described herein for the same or other purposes.

C. Example Methods of Use

Various approaches may be used to gain intravascular access to the obstructive material within the vessel lumen. In some embodiments, the method includes percutaneously accessing the blood vessel lumen (such as a vein) with a guidewire, advancing an introducer sheath (such as any of the introducers disclosed herein) over the guidewire and through the access site, and inserting a treatment device (such as any of the treatment devices disclosed herein) through a lumen of the introducer sheath into the blood vessel lumen. The distal portion of the treatment device containing the treatment assembly can be advanced to a target treatment site within the vessel lumen. The access site can be at, for example, a femoral vein, an internal jugular vein, or a popliteal vein to treat a venous site, or a femoral artery or radial artery to treat an arterial site. In some embodiments the method includes aspirating or infusing a thrombolytic agent into or from the blood vessel before, during, or after extraction of the obstructive material.

In some embodiments, a guidewire ("GW"; see FIGS. 12A-12C) may first be inserted into the blood vessel lumen and advanced through the obstructive material such that a distal terminus of the guidewire is distal of the obstructive material. Next, the introducer 103 (FIG. 1) may be delivered over the guidewire so that a distal portion of the introducer 103 (FIG. 1) is positioned within the vessel lumen proximal of the obstructive material. In those embodiments in which the introducer includes a funnel at the distal end of sheath 110, the funnel 700 can be expanded into apposition with the blood vessel wall. The method can continue by inserting the treatment device 101 over the guidewire, through the introducer 103, and into the vessel lumen. In some embodiments, the treatment device 101 can be advanced through the obstructive material such that some or all of the treatment assembly 100 of the treatment device 101 is distal of the obstructive material. In some embodiments, the treatment assembly 100 can be advanced to a location in the vessel such that some or all of the treatment assembly 100 is proximal of the obstructive material.

According to some embodiments, the treatment assembly 100 may be contained within the sleeve 112 during delivery. Once the distal portion of the treatment device 101 is positioned at a desired location relative to the obstructive material at the treatment site, the sleeve 112 of the device 101 can be pulled proximally relative to the treatment assembly 100 (or the treatment assembly pushed distally relative to the sleeve 112) to release one or both of the cutting and capture portions of the treatment assembly 100, thereby allowing the capture portion 200 and/or cutting portion 300 to self-expand. In some embodiments, the treatment assembly 100 may be expanded distal of the obstructive material such that no portion of the capture portion 200 and no portion of the cutting portion 300 engages the obstructive material during and/or immediately after expansion. In some embodiments, at least a portion of one or both of the capture portion 200 and the cutting portion 300 self-expand within the obstructive material. In some embodiments, the capture portion 200 is distal to the obstructive material and the cutting portion 300 is proximal to the obstructive material. As described elsewhere herein, in some embodiments one or both of the capture portion 200 and the cutting portion 300 are not self-expanding and require mechanical actuation.

While the capture and cutting portions 200, 300 are in an expanded configuration, the cutting portion 300 can be pushed towards the capture portion 200 and/or the capture portion 200 can be pulled distally towards the cutting portion 300 (either serially, simultaneously or back and forth). Alternately, the capture and cutting portions 200 and 300 can be pulled in a proximal direction to simultaneously or serially cut and capture the obstructive material. Before, during, or after such movement, the entire treatment assembly 100 can be pushed distally or pulled proximally towards the sheath 110. As the assembly 100 and/or device 101 is pulled proximally, the blades 302 of the cutting portion 300 cut through the obstructive material in a direction generally parallel to the longitudinal axis of the blood vessel, thereby separating the obstructive material from the vessel wall and/or other obstructive material. The capture portion 200 collects the separated obstructive material and is then pulled into the sheath 110 for removal from the patient. As previously mentioned, in some embodiments the system 10 does not include an introducer sheath. In this embodiment, the treatment device 10 may be introduced into the vascular system via a standard introducer sheath. In embodiments with a funnel 700 on the distal end of sheath 110, the funnel helps to capture all the obstructive material as the treatment device is pulled into the sheath and from them out of the of the blood vessel. In embodiments with aspiration capabilities, aspiration can be applied to one, some or all of the elongated shafts associated with the treatment system (e.g., the sheath 110 via connections in hub 105, or the sleeve 112, the outer member 111, via connections in the handle 12, etc.) to reduce the chance of embolic complications.

As previously mentioned, both the capture portion 200 and the cutting portion 300 may be self-expanding, so that when the sleeve 112 is retracted, the capture and cutting portions self-expand into the expanded state. For example, the sleeve 112 may be partially retracted to expand the capture portion, and then further retracted to expand the cutting portion. Additionally or alternatively, the capture portion and/or the cutting portion may be expanded by active actuation. For example, one or both of the capture portion 200 and the cutting portion 300 may be coupled to an actuation member that, when actuated by the operator (via a handle at a proximal portion of the treatment device 101), causes the capture portion 200 and/or the cutting portion 300 to partially or fully expand. For example, in some embodiments the treatment device includes an actuation member that is coupled to a distal end region of a corresponding one of the capture portion 200 or cutting portion 300 and when pulled, shortens the length of that component which has the effect of expanding that component. In those embodiments where the capture portion 200 and the cutting portion 300 are integrated within a single expandable component, a single actuation member may cause both to expand and/or collapse together. Likewise, in those embodiments where the capture portion 200 and the cutting portion 300 are separate components, a single actuation member may cause only one portion to expand and/or collapse. In some embodiments where the capture portion 200 and the cutting portion 300 are separate components, each of the capture portion 200 and the cutting portion 300 may be independently actuatable, whether by separate actuation members or by different mechanisms or timings via the same actuation member, According to various embodiments, one of the capture portion 200 or the cutting portion 300 is self-expanding and the other of the capture portion 200 or the cutting portion 300 requires active expansion. For example, the capture portion 200 can self-expand when the sleeve 112 is retracted, while the cutting portion 300 requires expansion with an actuation member. In this example, the cutting portion 300 may be expanded for only the first portion of the thrombus removal step to facilitate initial removal of the thrombus from the wall, but is then retracted during the remainder of the thrombus removal step as it is no longer needed.

According to several embodiments, the treatment assembly 100 of the treatment device 101 is positioned distal to the obstructive material, expanded, and then manipulated such as rotated, translated, or both, to separate obstructive material from the wall. For example, the treatment assembly can comprise one or more cutting elements (FIGS. 20A, 20B, 21A, etc.), and the inner elongated member is rotated to expand the cutting element to some or all of its expansion amount, and then manipulated to separate obstructive material from the treatment site. The treatment device can be readvanced for a further expansion and manipulation, in some cases to a larger expansion amount, for additional separation of obstructive material.

At any point before, during, or after the foregoing methods, aspiration may be applied at the treatment site to further reduce the risk of embolization.

At any point before, during, or after the foregoing methods, the treatment area may be flushed with or without aspiration to assist in separating and capturing occlusive material. The flush may be applied through the treatment device via a fluid line connected to a flush source. Alternately, flush may be applied from the side arm of the introducer sheath.

In some embodiments, both aspiration and flush may be applied to the treatment site. For example, an aspiration source may be connected to the treatment device and a flush source may be connected to the introducer 103. Conversely, an aspiration source may be connected to the introducer 103 and a flush source may be connected to the treatment device 101. Alternately, both are connected to the treatment device 101, or both are connected to the introducer 103.

During separation and/or removal of obstructive material from a treatment site by the treatment assembly, the distal capture sheath may capture and contain any material that has not been aspirated or otherwise removed by treatment device.

During or after separation and/or removal of obstructive material from a treatment site by the treatment assembly, the treatment device can be removed from the introducer 103 (FIG. 1). Aspiration applied through the introducer 103 can reduce embolic particles during device removal. Inclusion of a funnel 700 on the introducer sheath 110 may also reduce the possibility of embolic particles remaining in the vasculature as the treatment device is removed.

At any point before, during, or after engagement of the cutting elements with the obstructive material, the treatment device and/or treatment assembly can be configured to deliver energy at the treatment site. For example, the treatment device and/or treatment assembly may be configured to vibrate and/or emit ultrasonic energy. All of the methods detailed above apply to the embodiments discussed below as well.

Figures 29A, 29B:
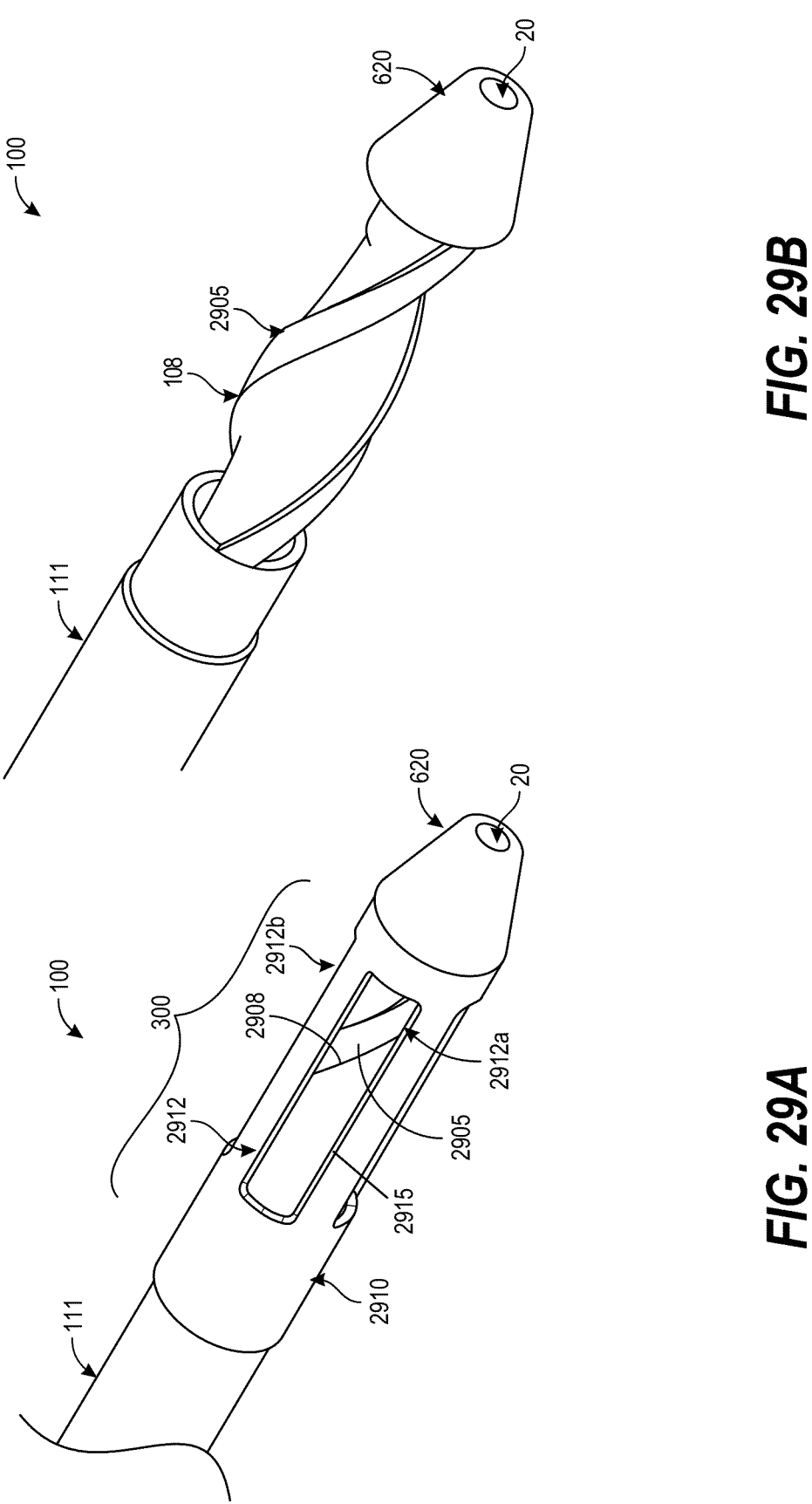
FIGS. 29A and 29B show a treatment assembly configured in accordance with several embodiments of the present technology.

In some embodiments, for example as shown in FIGS. 29A and 29B, the treatment assembly 100 comprises a cutting portion 300 including a housing 2910 and a rotating member 2905 having one or more helical cutting edges 2908 disposed within the housing 2910. The housing 2910 can be a distal portion of or carried by the distal portion of the second elongated member 108 and the rotating member 2905 can be a distal portion of or carried by the distal portion of the first elongated member 111. The housing 2910 can comprise a tubular sidewall having one or more windows 2912 (e.g., windows 2912a, 2912b) to expose the inner rotating member 2905. FIG. 29A shows the assembly 100 with the rotating member 2910 and the housing 2905, while FIG. 29B shows the housing 2910 removed to better illustrate the rotating member 2905. The edges 2915 of the windows 2912 provide a fixed edge against which the helical cutting edge 2908 shears when rotated, thus facilitating a cutting action along a shearing line on any material in contact with the shearing line. The edges 2915 of the windows 2912 may be sharpened to increase the cutting action. The edges 2915 may also be slightly oriented inward, to exert a shear force on the cutting edges 2908 of rotating member 2905, to further increase the shear force. Alternately, the helical cutting edges 2908 may be slightly oriented outwards, for the same purpose. The housing 2910 may be made from a laser cut hypotube. The sharpened edge and/or the inward orientation of the edges 2915 may be secondary operations on the hypotube. As shown in FIGS. 29A and 29B, the treatment assembly 100 may also include a lumen 20 and a tapered tip 620 to allow for atraumatic positioning of the treatment device 101 over a guide rail to a treatment site.

The helical cutting edge 2908 may be formed by a helical groove in the rotating member 2905 in which the edge of the groove is sharpened, similar to a fluted cutter, such as a drill bit. As shown in FIG. 29B, the rotating member 2905 can have one or more cutting flutes.

Figures 30A, 30B:
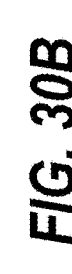
FIGS. 30A and 30B show a treatment assembly configured in accordance with several embodiments of the present technology.

In some embodiments, as illustrated in FIGS. 30A and 30B, the treatment assembly 100 comprises a first tubular housing 3010 and a second tubular housing 3005 disposed within the first housing 3010. The first housing 3010 can be a distal portion of or carried by the distal portion of the second elongated member 108 and the second housing 3005 can be a distal portion of or carried by the distal portion of the first elongated member 111. FIG. 30A shows the treatment assembly 100 with the second housing 3005 and the first housing 3010, while FIG. 30B shows the treatment assembly 100 with the first housing 3010 removed to better illustrate the second housing 3005. The first housing 3010 can comprise a tubular sidewall having one or more windows 3012 that expose the second housing 3005, and the second housing 3005 can comprise a tubular sidewall having one or more windows 3006.

At least some of the sides of the window(s) 3012 (for example, including the longitudinal sides) can comprise a longitudinally extending edge 3015, which may be blunt or sharpened. At least some of the sides of the window(s) 3006 (for example, including the longitudinal sides) can comprise a cutting edge 3008. The cutting edge(s) 3008 can be straight or helical. In some embodiments, the longitudinally extending sides of the windows(s) 3006 are not parallel with the longitudinal axis of the second housing 3005 (e.g., the sides are slanted). The second housing 3005 can be configured to rotate relative to the first housing 3010 (e.g., via rotation of the second elongated member 108 relative to first elongated member 111, etc.) such that the cutting edges 3008 of the windows 3006 of the second housing 3005 and the fixed edge 3015 of the first housing 3010 form a shearing edge. The edges 3008 and 3015 can either or both be sharpened, in a manner that optimizes the cutting force on material in contact with the shearing edge. For example, the cutting edges 3008 of the rotating member 3005 can be sharpened to have the sharp edge on the outside surface, and the outer member cut out edges 3015 are sharpened to have the sharp edge on the inside surface. A distal tapered tip 620 and inner lumen 20 facilitates atraumatic advancement of the device over a guide rail up to and through a treatment area.

The size of windows 3012 (both width length, and thickness) can determine the size of the cutting surface. The number of windows determines the number of cutting surfaces and shearing edges. A larger cut-out or more than one cutting surface would increase the size of the cutting surface available to remove obstructive material. As previously mentioned, in some embodiments the treatment system 10 includes an aspiration source configured to be fluidly coupled to the treatment device 101. In several of such embodiments, the aspiration source can be configured to be fluidly connected to the annular space between first housing 3010 and the second housing 3005. In use, should the housing windows become blocked by material, the material would create a vacuum seal and the aspiration source would exert an inward force on the material through the window 3012. In such embodiments, it may be preferable to limit the window to quantity one, and to limit the size, to facilitate creation of a vacuum seal. In several embodiments, the outer edge of the window has a raised bead or flange to optimize the vacuum seal.

Figure 31:
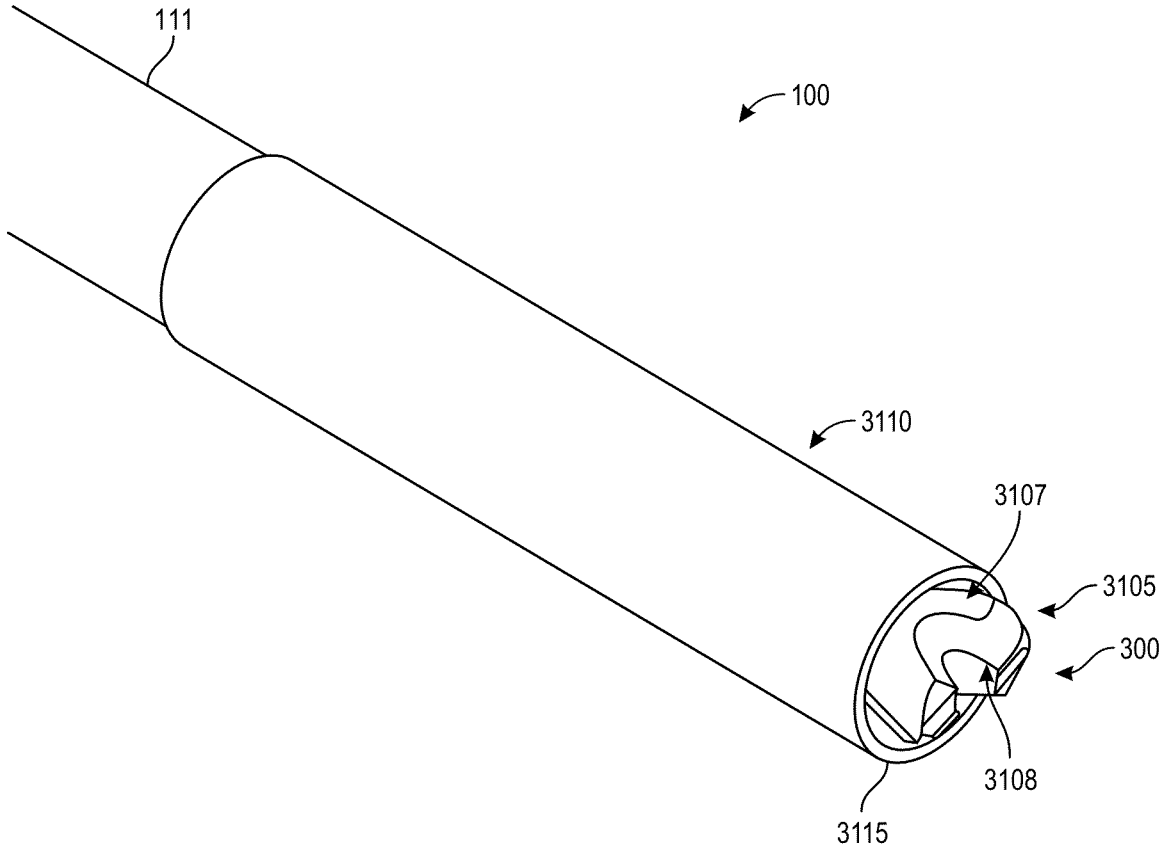
FIG. 31 shows a treatment assembly configured in accordance with several embodiments of the present technology.

In some embodiments, for example as shown in FIG. 31, the treatment assembly 100 comprises a cutting portion 300 including a housing 3110 and a rotating member 3105 having once or more cutting edges 3108 disposed within the housing 3110. The housing 3110 can be a distal portion of or carried by the distal portion of the second elongated member 108 and the rotating member 3105 can be a distal portion of or carried by the distal portion of the first elongated member 111. The housing 3010 includes a distal opening 3107 through which the rotating member 3105 protrudes by a fixed or variable distance. The rotating element 3105 can have cutting edges 3108 on the distal end. In the version shown in FIG. 31, the cutting edges 3108 are formed by cutting helical grooves into the distal face of the rotating member 3105, and sharpening one or more edges of each groove. The grooves can be cut from a relatively flat distal surface to provide a planer cutting surface, as illustrated, or can be cut from a tapered front surface, to provide a tapered or pointed cutting surface, similar to the front of a drill bit. The edge 3115 of the housing 3110 surrounding the distal opening 3107 may also be sharpened, or may be blunt. In some embodiments, the cutting edges 3108 are in contact with edge 3115 of the distal opening 3107 to create a circular shearing edge when rotating member 3105 is rotating.

In some embodiments, the rotating member 3105 defines a lumen therethrough to allow the device to be advanced over a guide rail. The guide rail may be retracted into the device during a cutting step, to maximize the cutting surface against the occlusive material. In some embodiments the rotating member 3105 does not include an inner lumen.

Figures 32A, 32B:
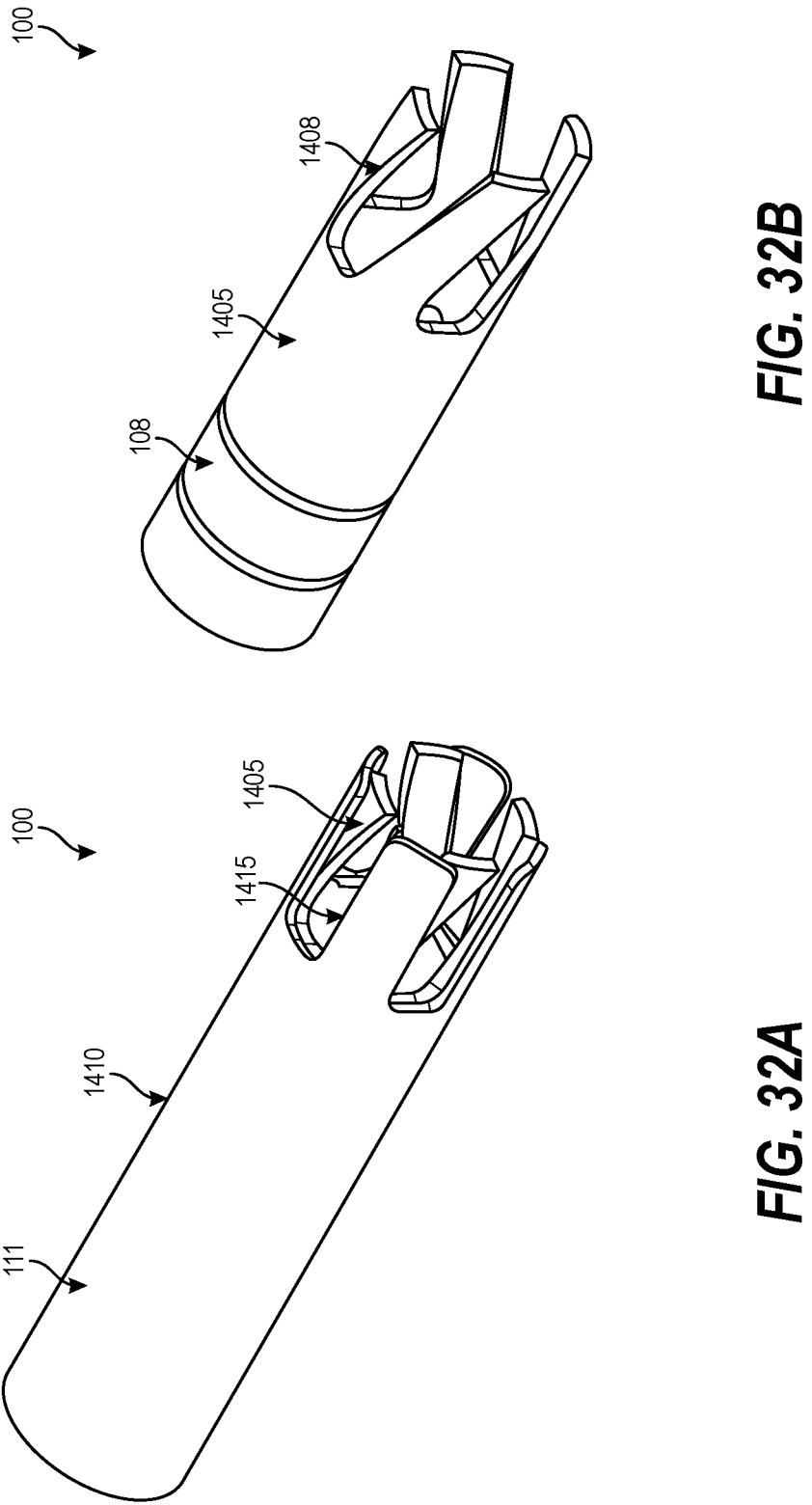
FIGS. 32A and 32B show a treatment assembly configured in accordance with several embodiments of the present technology.

In some embodiments, for example as shown in FIGS. 32A and 32B, the treatment assembly 100 comprises an inner rotating tube 1405 and an outer fixed tube 1410, both with crenulated-patterned leading edges. The inner tube crenulated pattern has diagonal or helical edges 1408. The edges 1415 of the outer tube crenulation are either straight or diagonal in the cross direction, and serve as a fixed edge against which the helical cutting edge of the inner tube shears against when rotated, thus facilitating a cutting action on any material in contact with the shearing line. The edges 1415 of the outer tube cut crenulations may be sharpened to increase the cutting force. The edges 1415 may also be slightly oriented inward, so as to exert a shear force on the rotating member 1405, to further increase the cutting force. Alternately or additionally, the edges 1408 of inner tube crenulations may be slightly orientated outwards for the same effect. FIG. 32A shows the assembly, FIG. 32B shows the outer tube 1410 removed to better illustrate the inner tube 1405.

Figure 33:
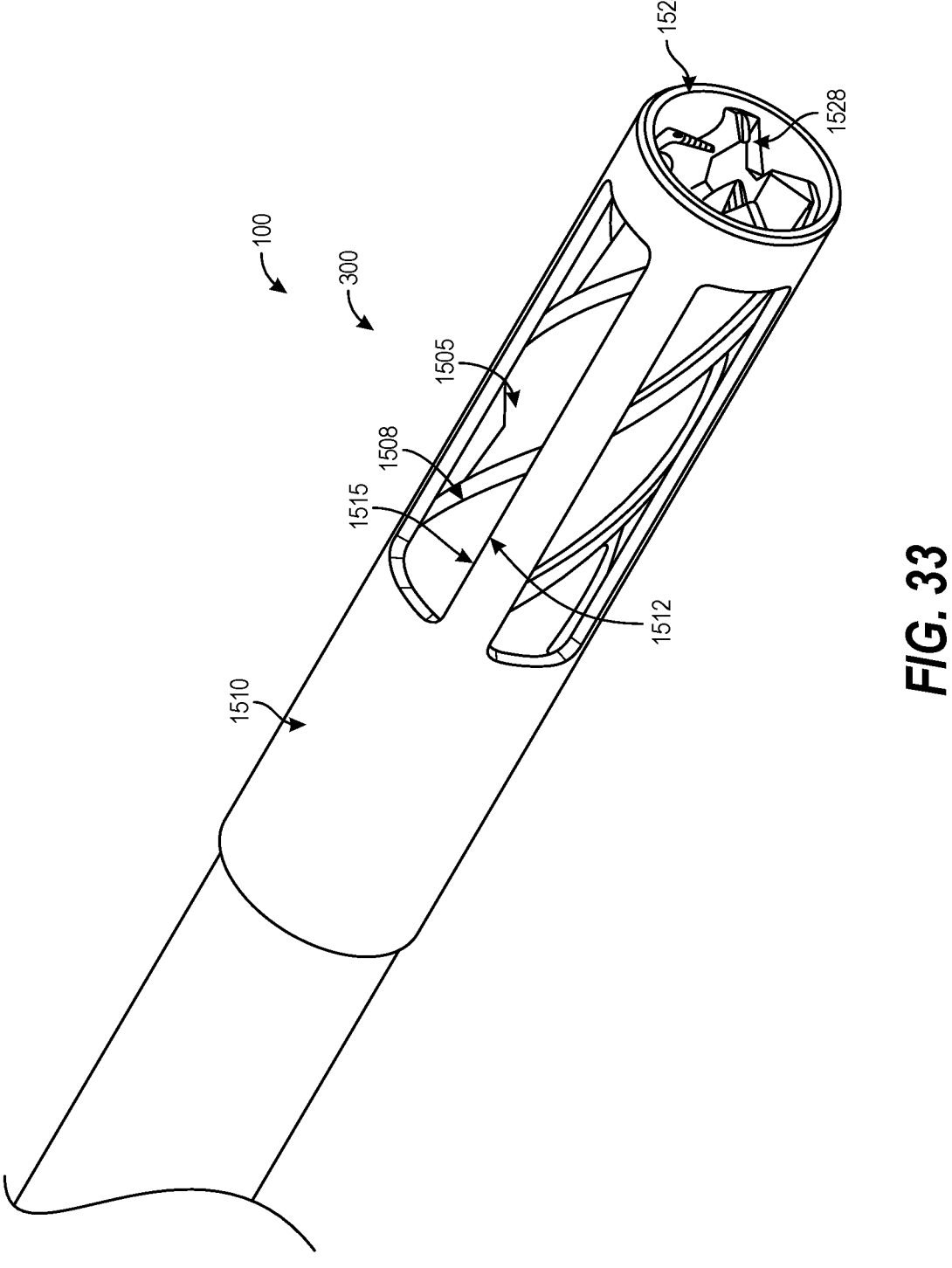
FIG. 33 shows a treatment assembly configured in accordance with several embodiments of the present technology.

According to several embodiments, the treatment assembly 100 can comprise a combined end and side cutter. For example, as shown in FIG. 33, the treatment assembly 100 comprises an inner rotating member 1505 and an outer tube 1510. The inner rotating member 1505 has sharpened helical edges 1508 on the side surfaces and sharpened edges 1528 on the front surface. The outer tube 1510 has both side cut-outs 1512 with edges 1515 and open end with outer edge 1525 in the front, to expose the side surface and the front end of the treatment assembly 100 to the cutting edges 1508 and 1528 of rotating cutting member 1505.

In another example, a treatment assembly 100 has an inner rotating tube and an outer fixed tube, wherein the inner tube has both cut outs with helical cutting edges on the side, and crenulated cutting edges on the end. The outer fixed tube has cut-outs on the side with fixed edges, and crenulated pattern on the end, which in combination with the inner tube side and end cutting edges forms a shearing cutting line on both the side and end of the treatment assembly when the inner tube is rotated.

Figure 34:
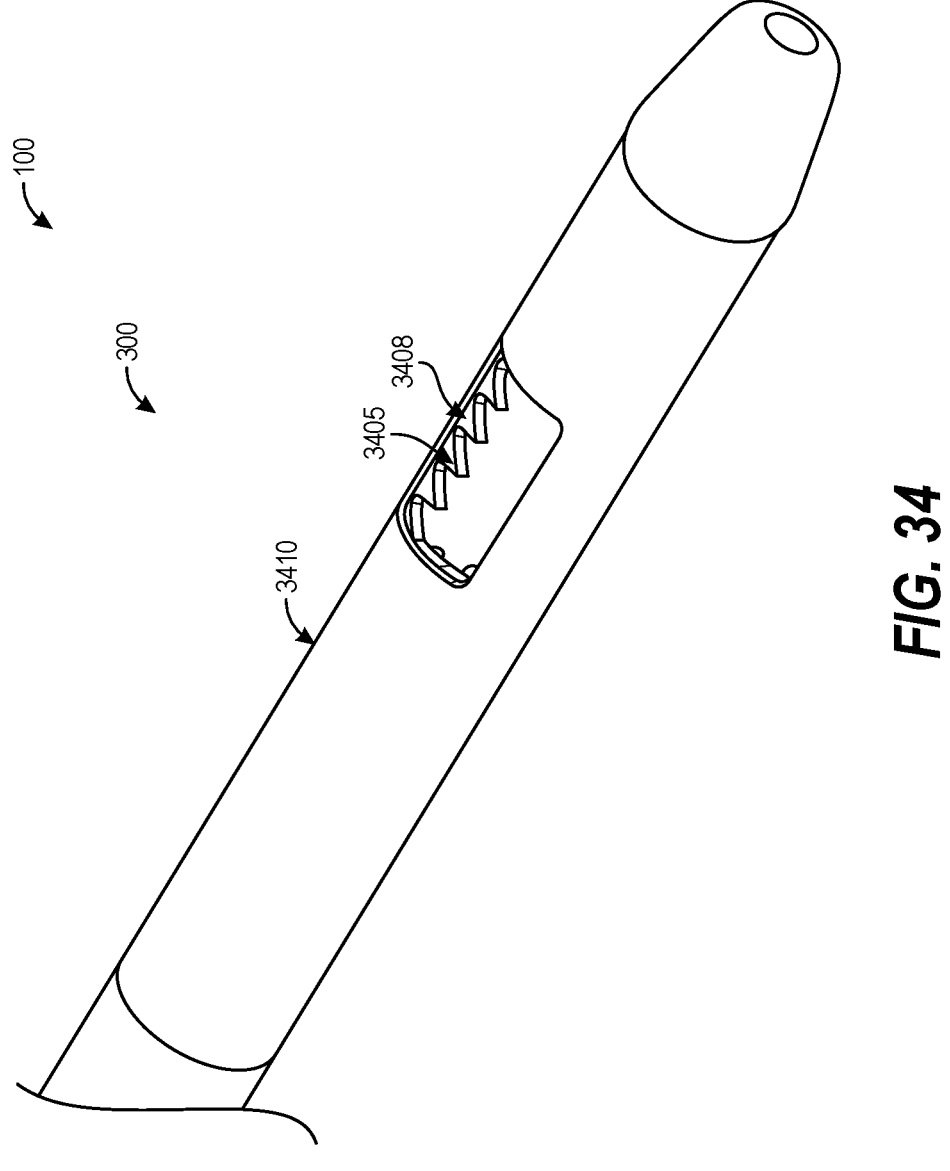
FIG. 34 shows a treatment assembly configured in accordance with several embodiments of the present technology.
Figure 35:
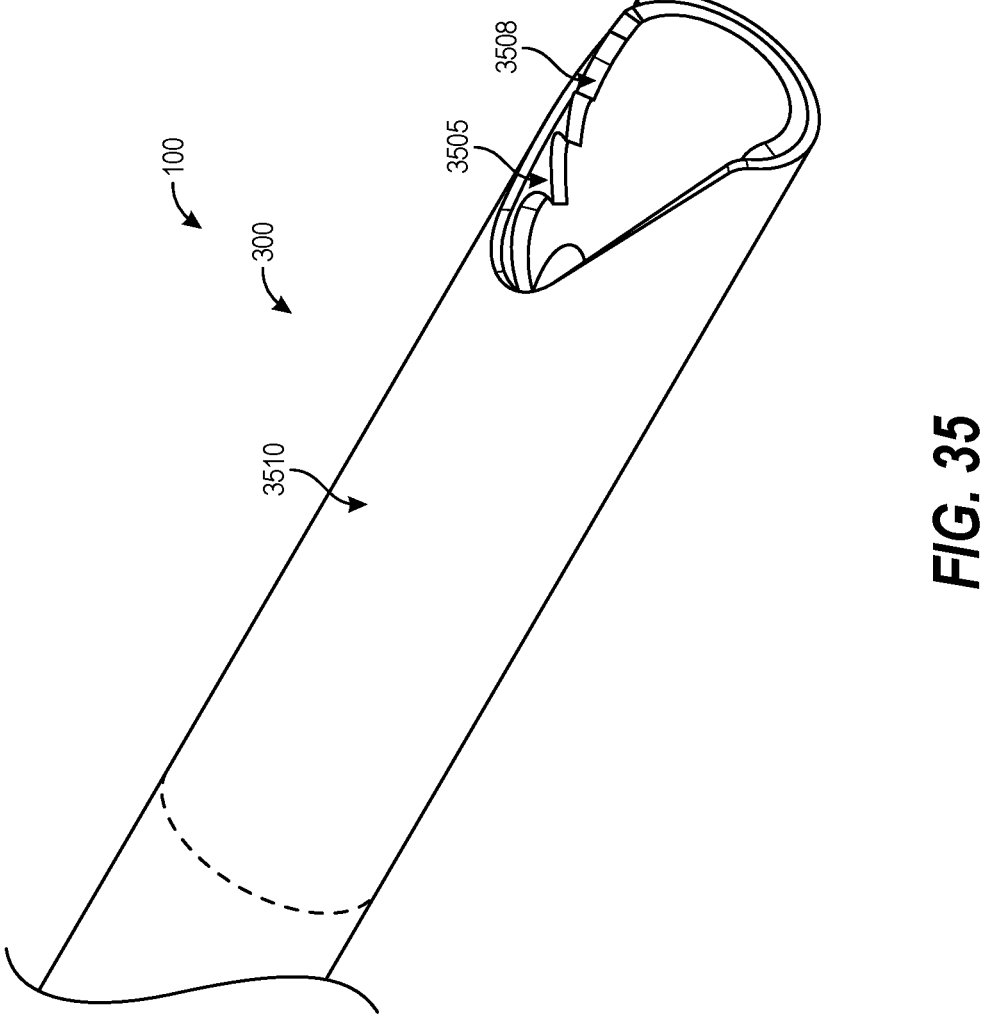
FIG. 35 shows a treatment assembly configured in accordance with several embodiments of the present technology.

In any of these embodiments, the cutting edge may be a sharpened edge. Alternately, the cutting edge may be a serrated edge. As shown in FIG. 34 showing an inner rotating member 3405 and an outer tube 3410, for example, the inner rotating member 3405 of a side-cutting assembly may have a serrated pattern on the cut-out, creating a serrated cutting edge 3408. The edge may be both serrated and sharpened. In another example, as shown in FIG. 35 showing an inner rotating member 3505 and an outer tube 3510, the inner rotating member 3505 of an end cutter has a serrated pattern on the crenulation, creating a serrated cutting edge 3508.

In any of the side-cutting, end-cutting, or combination cutting configurations described above, the inner rotating member may be driven by a motor. In these embodiments, the handle 12 (FIG. 1) can include an actuator (e.g., first actuator 14, second actuator 16, or another) that can turn on and off the motor. The handle itself may contain the motor.

Alternately, the handle includes a connection to an external motor. In these and other embodiments, the inner rotating member may alternately or additionally be rotated manually by the user, via an actuator on the handle 12.

Figures 36A, 36B:
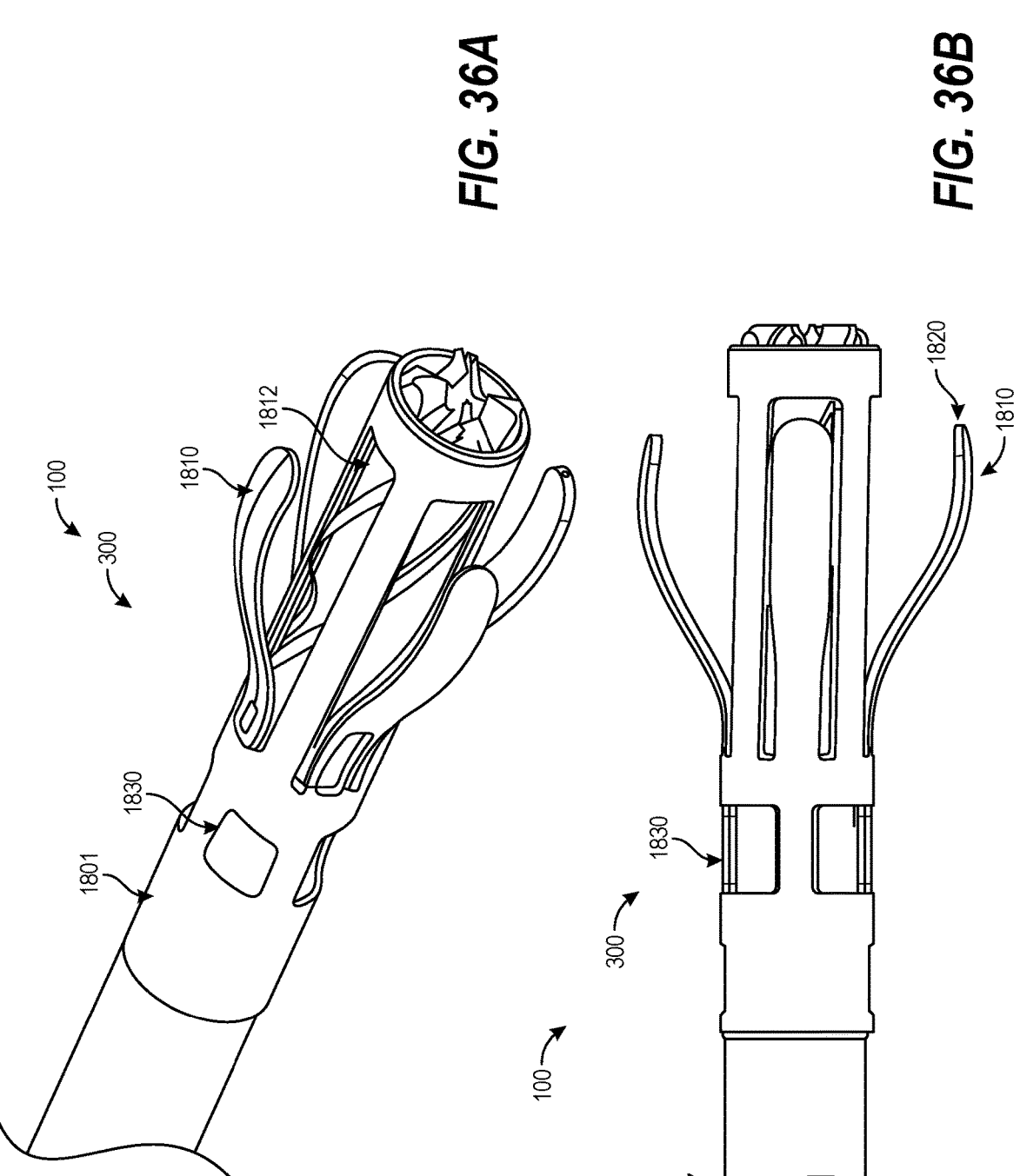
FIGS. 36A and 36B show a treatment assembly configured in accordance with several embodiments of the present technology.

In any of the treatment assemblies described above, the treatment assembly 100 may include a guiding element that occlusive material towards the cutting surfaces and/or cutting edges as the treatment device 101 is advanced in a vessel towards or through occlusive material. For example, as shown in FIGS. 36A and 36B, the treatment assembly 100 may include two or more arms 1810 which expand outwards and act to direct or "gather" tissue toward the side windows 1812 to facilitate cutting of the tissue as the device 101 is advanced. FIG. 36A is an isometric view. FIG. 36B is a side view to better illustrate the shape of arms 1810. The arms 1810 may be formed from a cut-pattern in an outer tube 1801 and heat-set to an open position. The shape of the arms 1810 may be configured to minimize the chance of the arms catching on the wall of the vessel. For example, as shown, the ends 1820 of the arms 1810 are curved inwards. During delivery of the device to a target site, the arms 1810 may be retracted by means of a constraining sheath (not shown). When the treatment assembly 100 is near or at the target site, the constraining sheath is pulled back to allow the arms 1810 to expand outwards and function to direct tissue. The arms 1810 may also be formed from separate elements that are attached to the outer tube 1801.

Also as shown in FIGS. 36A and 36B, treatment assembly 100 may include side openings 1830 proximal to the cutting surfaces. In an embodiment wherein treatment device 101 is connected to an aspiration source (e.g., suction or aspiration source 18), openings 1830 may help to gather obstructive material which has been separated from the vessel target site and remove the material from the patient.

Figures 37A, 37B:
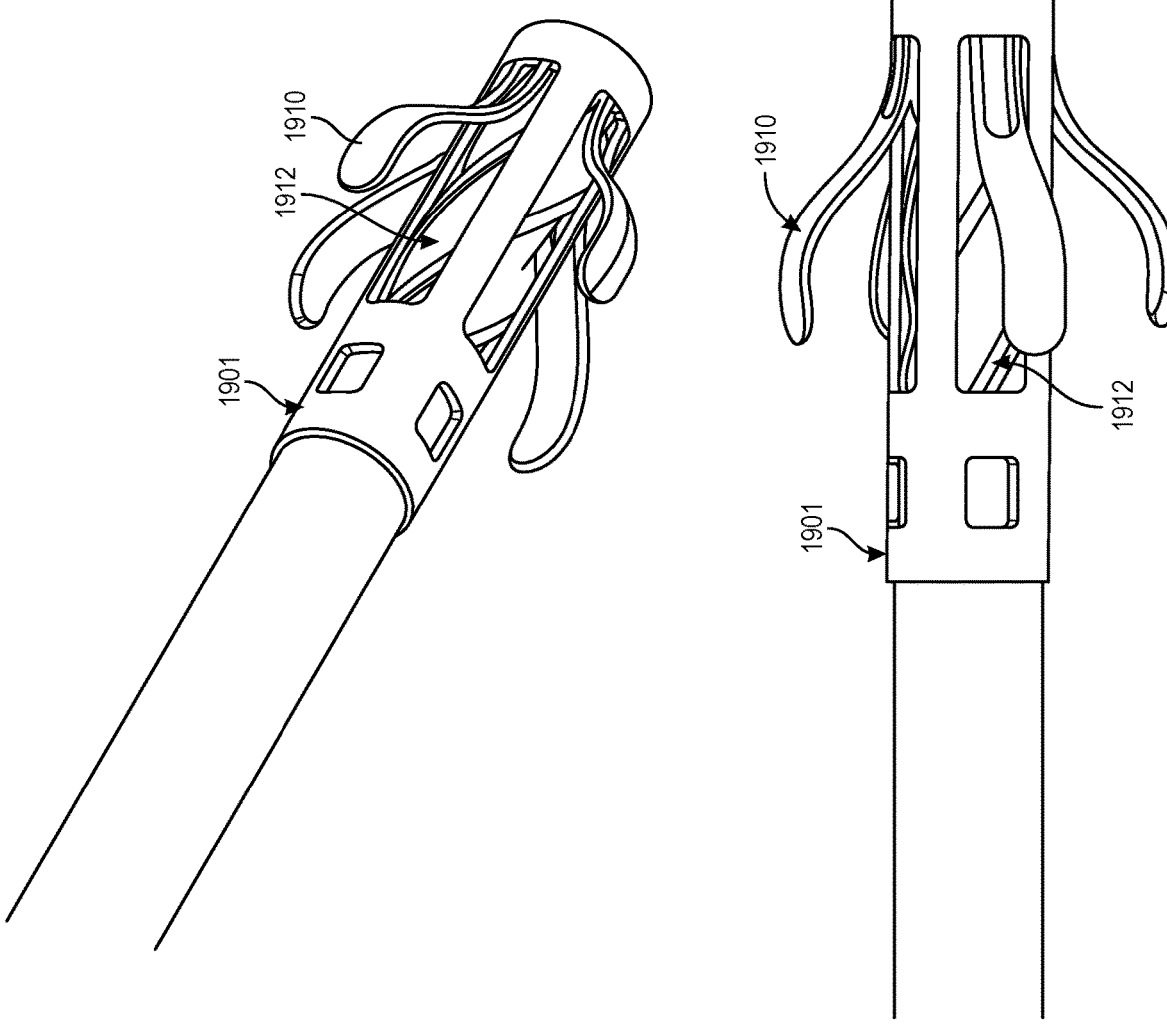
FIGS. 37A and 37B are an isometric view and side view of another treatment assembly with features to direct tissue.

As shown in FIGS. 37A and 37B, the arms 1910 of the outer tube 1901 may be oriented in the opposite direction. In this embodiment, the treatment assembly 100 is positioned passed an occlusive area, with the arms 1910 constrained inside an outer constraining sleeve (not shown). Once positioned, the sheath is retracted to allow the arms to expand outwards. As the device is pulled back, the arms direct occlusive material towards the cutting windows 1912.

Figures 38A, 38B:
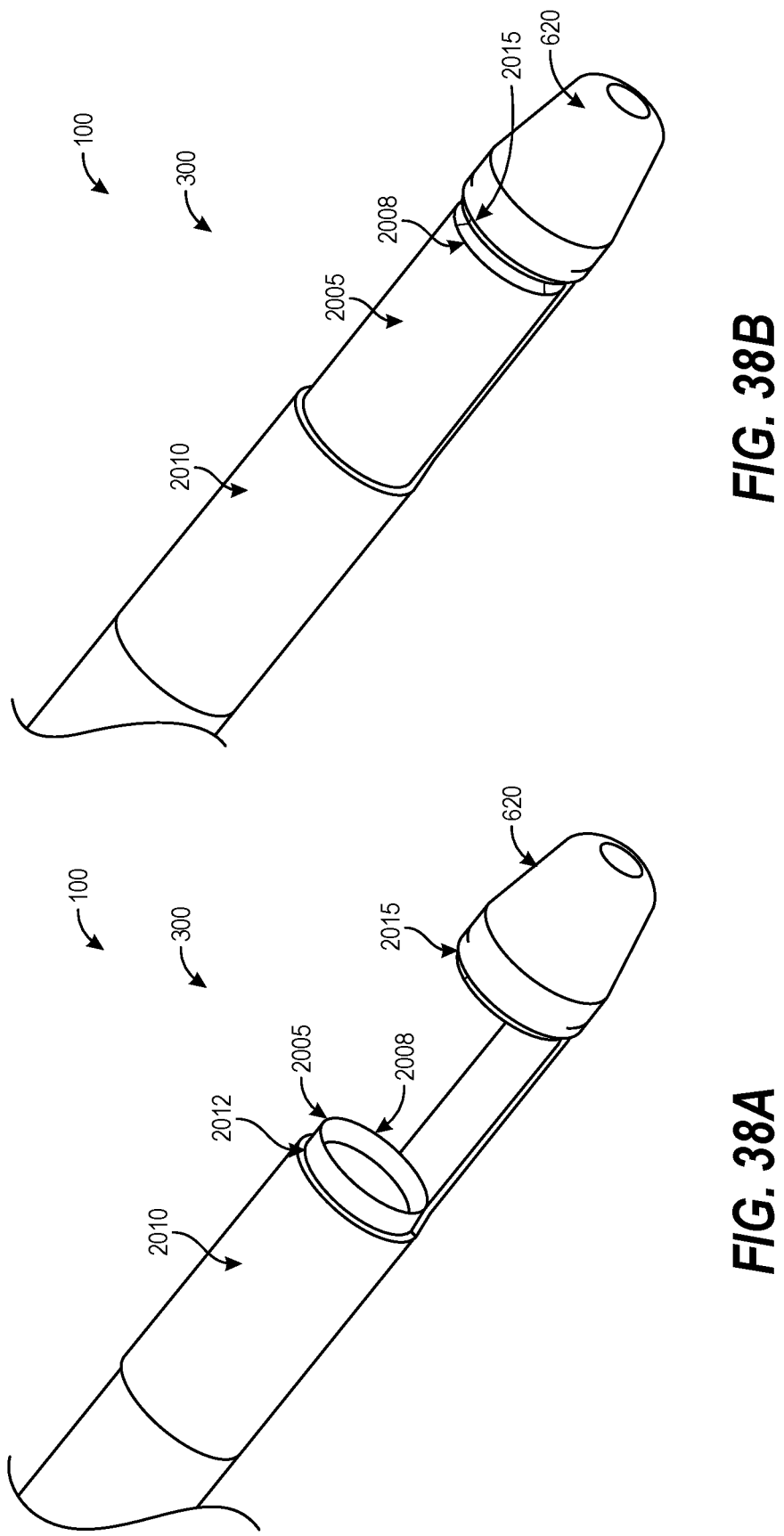
FIGS. 38A and 38B show a treatment assembly configured in accordance with several embodiments of the present technology.

In some embodiments, the treatment assembly 100 comprises a coring cutter. For example, as shown in FIGS. 38A and 38B, the cutting portion 300 can comprise an outer tube 2010 with a side cut-out window 2012, and an inner tube 2005 with a sharpened end 2008. The distal edge 2015 of outer side cut-out window 2012 may also be sharpened. As shown in FIG. 38A, when the treatment assembly is positioned against occlusive material, the inner tube 2005 is recessed proximal to the window 2012 of outer tube 2010 to allow the occlusive material to intrude through window 2012 into a recessed space. During a cutting step, as shown in FIG. 38B, the inner tube is forcefully pushed forward to push inner tube edge 2008 towards outer tube edge 2015 and thereby cut the occlusive material in the recessed space in a punch-like fashion. In the first instance, the inner tube has a sharpened edge on the distal end of the inner tube opening. One or more of the sharpened edges 2008 and 2015 may also be serrated.

Cutting of obstructive material may be performed by the user with a manual actuator on handle 12 that slides inner member 2005 forward and then springs back. Alternately, the inner tube 2005 may be connected to a spring in handle 12 configured to push inner tube forwards. The spring can be released by the user, to impart more force on tissue during the cutting step. In an embodiment, a single actuator motion propels the inner member forward and then resets the inner member in the recessed position.

Figures 39A, 39B:
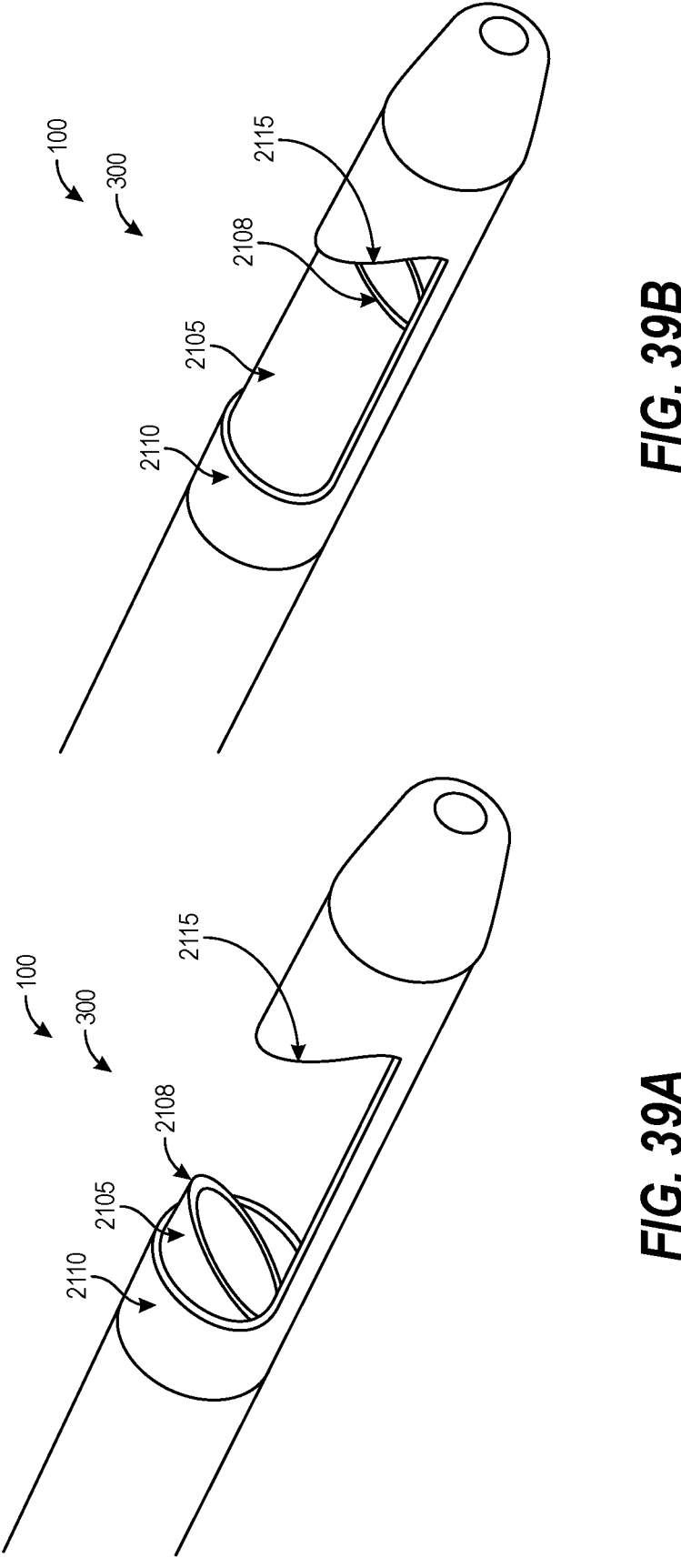
FIGS. 39A and 39B show a treatment assembly configured in accordance with several embodiments of the present technology.

In some variations, for example as shown in FIGS. 39A and 39B showing an inner tube 2105 and an outer tube 2110, the leading edge 2108 of the inner tube 2105 is slanted. Similarly, the outer tube edge 2115 may also be slanted in the opposite direction. In this manner, during a cutting step as the inner tube is pushed forward, the cutting step has both a slicing and a punching action. FIG. 39A shows the inner member 2105 almost completely recessed. In use, the inner member may be completely recessed during a positioning step, to maximize the recessed space. FIG. 39B shows the inner member almost at the end of the travel, in a cutting configuration.

Any of the treatment systems herein may include a positioning element configured to position the treatment assembly and/or cutting portion within the blood vessel (or other body lumen) in close proximity to the obstructive material to improve the efficiency of the cutting. This is especially valuable in embodiments where the cutting surface is on one side of the elongated member 102 and/or if a certain amount of counterforce would increase the efficacy of the cutting action. For example, the positioning element may direct the cutting portion of the treatment assembly (either on the side or the end of the treatment assembly, or both) against one side of a vessel lumen. The positioning element can additionally or alternatively be utilized to offset the cutting portion from the vessel wall to protect the vessel wall. In any case, the positioning element can be incorporated into the treatment device 101 (for example, on the elongated member 102, first elongated member 111, second elongated member 108, or sleeve 112) or can be disposed on a separate device that can be delivered over, through, and/or alongside the treatment device 101. As used herein, "positioning device" refers to a separate device on which the positioning element is disposed. The positioning elements of the present technology can benefit any of the treatment devices or assemblies disclosed herein, but can be especially advantageous for treatment assemblies in which the cutting elements do not expand outwardly in the lumen of the treatment vessel (such as side cutters, end cutters, and coring cutters).

Figure 40:
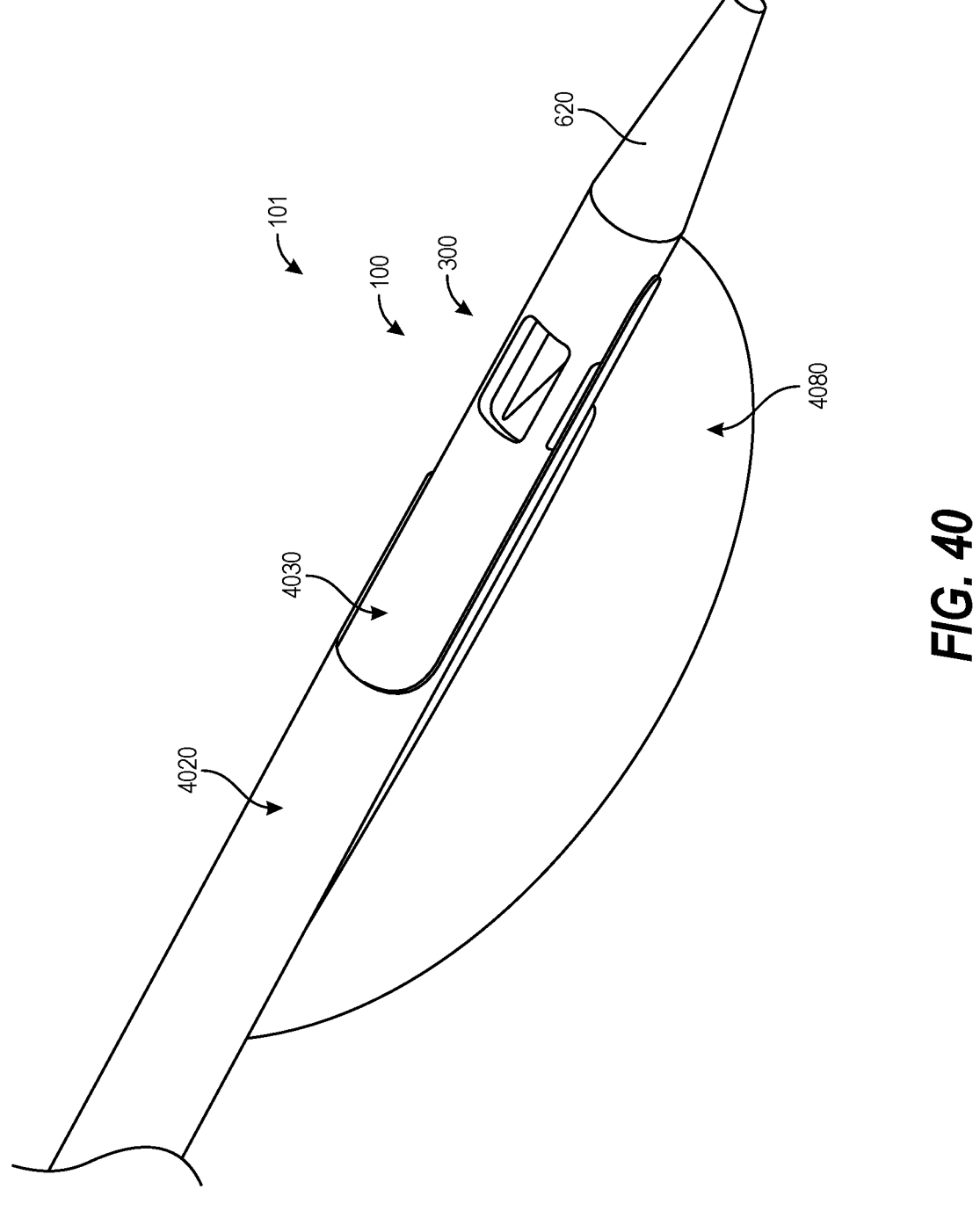
FIG. 40 is a perspective view of a treatment assembly with a positioning element configured in accordance with several embodiments of the present technology.

In some embodiments, the positioning element can comprise an expandable structure. For example, as shown in FIG. 40, the positioning element can comprise an inflatable balloon 4080 carried by a distal portion of an elongate shaft 4020. The elongate shaft 4020 can comprise a tubular sidewall defining a lumen therethrough and including a window 4030 at the distal portion of the elongate shaft 4020. The balloon 4080 can be positioned about the circumference of the elongate shaft 4020 opposite the window 4030. In some embodiments, all or a portion of the balloon 4080 is longitudinally aligned with all or a portion of the cutting portion 300 of the treatment assembly 100 (as shown in FIG. 40). In other embodiments, for example as shown in FIGS. 41A-41F (discussed below), the balloon 4080 is longitudinally adjacent or spaced apart from the cutting portion 300. The balloon 4080 can be proximal of the cutting portion 300 along a longitudinal axis of the system (as shown in FIGS. 41A-41F), aligned with the cutting portion 300 (as shown in FIG. 40), or may be distal to the cutting portion 300 (not shown). Referring still to FIG. 40, the elongate shaft 4020 optionally includes a distal tip 620 at its distal end. In other embodiments, the distal tip 620 is coupled to the distal end of the elongate member 102 (or component thereof, such as first and/or second elongated members 108, 111), or neither the elongate shaft 4020 or the elongate member 102 include a distal tip 620.

The elongate shaft 4020 can be configured for use with the treatment device 101. For example, in some embodiments the lumen of the elongate shaft 4020 is configured to receive the elongate member 102 (which may be a single elongate member or comprise multiple elongate members, such as first and second elongate members 108 and 111) of the treatment device 101 therein. The treatment device 101 can be positioned relative to the elongate shaft 4020 such that the cutting portion 300 of the treatment device 101 is longitudinally aligned with (and exposed through) the window 4030 of the elongate shaft 4020. The treatment device 101 can be fixed longitudinally within the elongate shaft 4020, or may be slidably disposed within the elongate shaft 4020. Likewise, the treatment device 101 can be rotationally fixed relative to the elongate shaft 4020, or may be configured to rotate within the elongate shaft 4020. In some embodiments, one or more components of the treatment device 101 can rotate relative to the elongate shaft 4020 and/or balloon 4080 but cannot translate relative to the elongate shaft 4020 and/or balloon 4080.

According to some methods of use, the distal portion of the treatment device 101 and the distal portion of the elongate shaft 4020 are delivered together to the treatment site. During delivery, the balloon 4080 is in a deflated and/or low-profile state. Once at the treatment site, the balloon 4080 can be expanded to position the cutting portion 300 in a desired location relative to the occlusive material and/or vessel wall. The treatment assembly 100 and/or cutting portion 300 can then be actuated to remove obstructive material. The balloon 4080 can be deflated, repositioned, and re-inflated as necessary for further obstructive material removal.

In some embodiments, the positioning element can be configured as a sub-selective guide to deliver the treatment assembly 100 to a treatment site. For example, the positioning device can first access and be positioned at a treatment site with a dilator (not shown). The dilator can then be removed and replaced with the treatment device 101. In some embodiments, the positioning device and the treatment device can initially be positioned together (as previously mentioned). In either scenario, the treatment device 101 can be removed from the positioning device and replaced with an alternate treatment device. For example, a treatment device with a treatment assembly including a side-cutter may be used to separate obstructive material from a treatment site, and then a treatment device with a treatment assembly including an end-cutter may be swapped in and used to separate additional obstructive material from the treatment site. In this manner, any combination of treatment devices, treatment assemblies, and/or cutting portions may be used in a single procedure.

The positioning element of FIG. 40 can be used with any of the treatment devices, treatment assemblies, cutting portions, and/or capture portions disclosed herein. As but more examples, FIGS. 41A-41F show different combinations of the positioning device shown in FIG. 40 with the cutting portion 300 shown and described with respect to FIGS. 20A and 20B. In any of these variations, at least a portion of the treatment device 101 can be longitudinally and/or rotationally fixed relative to the elongated shaft 4020. For example, the first elongated member 111 may be longitudinally and/or rotationally fixed relative to the elongated shaft 4020 while the second elongated member 108 is free to rotate and/or translate relative to the elongated shaft 4020 (thereby enabling expansion/collapse of the cutting element 2010). As another example, the second elongated member 108 may be longitudinally and/or rotationally fixed relative to the elongated shaft 4020 while the first elongated member 111 is free to rotate and/or translate relative to the elongated shaft 4020 (thereby enabling expansion/collapse of the cutting element 2010).

Figures 41A, 41B, 41C, 41D, 41E, 41F:
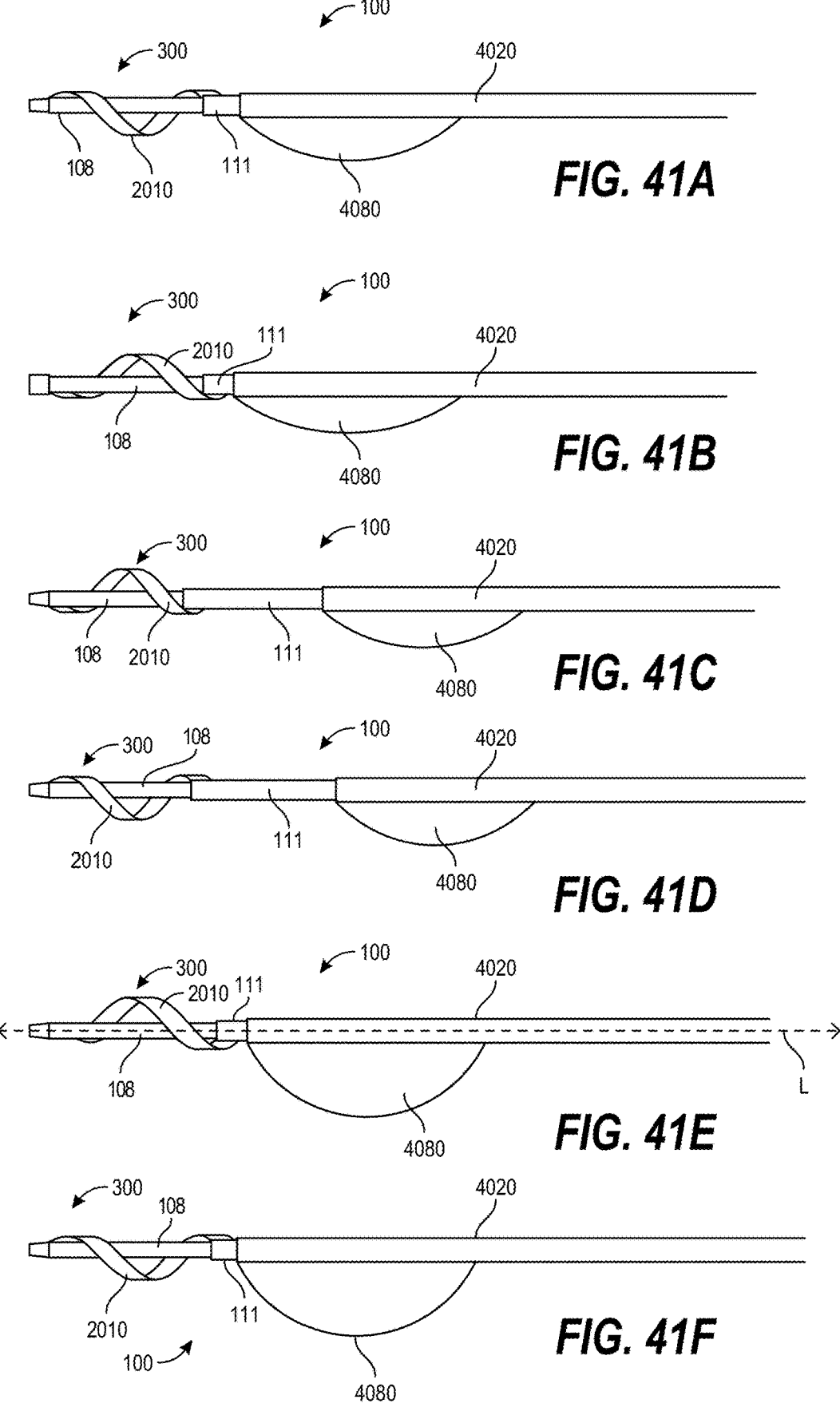
FIGS. 41A-41F show different positioning device and treatment device arrangements configured in accordance with several embodiments of the present technology.

As shown in FIG. 41A, the treatment device 101 and the positioning device can be arranged such that the cutting portion 300 is longitudinally adjacent the balloon 4080 and the cutting element 2010 is configured to expand predominantly in the direction of the expanded balloon 4080. FIG. 41B shows an example in which the cutting portion 300 is longitudinally adjacent the balloon 4080, but the cutting element is configured to expand predominantly in a direction that is different than that (including the opposite direction) of the expanded balloon 4080. In FIG. 41C, the cutting portion 300 is longitudinally spaced apart from the balloon 4080 (for example, by advancement of the treatment device 101 relative to the positioning device, or vice versa) and the cutting element 2010 is configured to expand predominantly in a direction that is different than that (including the opposite direction) of the expanded balloon 4080. In FIG. 41D, the cutting portion 300 is longitudinally spaced apart from the balloon 4080 (for example, by advancement of the treatment device 101 relative to the positioning device, or vice versa) and the cutting element 2010 is configured to expand predominantly in the direction of the expanded balloon 4080.

The balloon 4080 (or other positioning element) can be expanded to a radial distance from a central longitudinal axis L (only labeled in FIG. 41E) of the treatment system that is less than, the same as, or more than a maximum radial expansion distance of the cutting element 2010. Expansion of the balloon 4080 can be adjusted depending on the degree of expansion required of the cutting element 2010. FIGS. 41A-41D provide examples of smaller balloons and/or balloons expanded to a lesser degree, and FIGS. 41E and 41F provide examples of larger balloons and/or balloons expanded to a greater degree.

Figure 42:
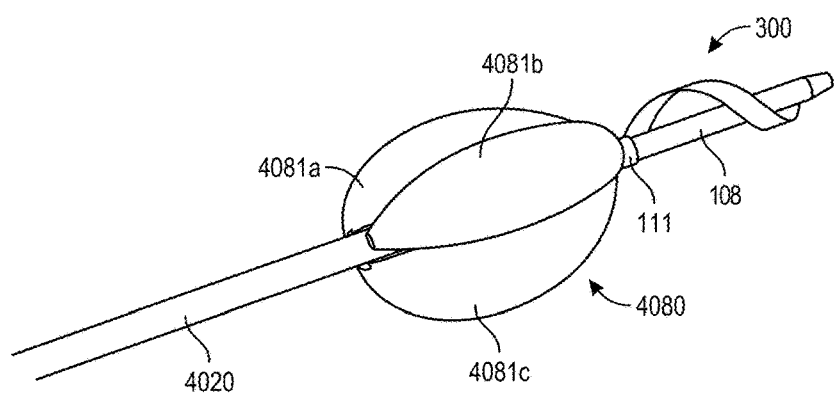
FIGS. 42 and 43 show a positioning device and treatment device arrangement configured in accordance with several embodiments of the present technology.
Figure 43:
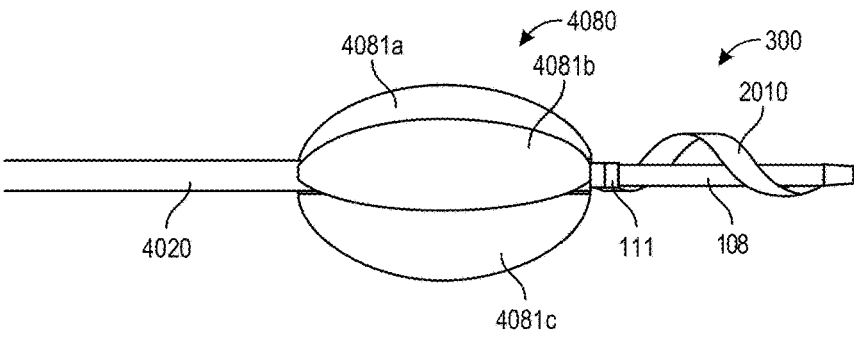
Figure 44:
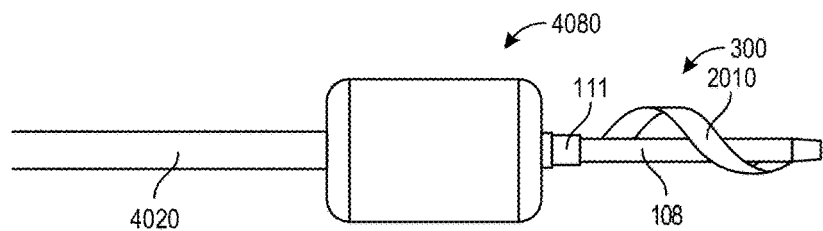
FIGS. 44 and 45 show a positioning device and treatment device arrangement configured in accordance with several embodiments of the present technology.
Figure 45:
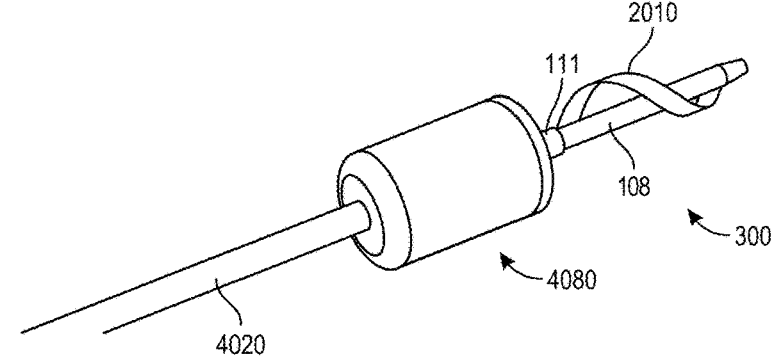

While the balloon 4080 shown in FIGS. 40 and 41A-41F is disposed eccentrically and/or on one side of the elongated shaft 4020, in some embodiments the balloon 4080 (or any of the positioning elements of the present technology) may be configured to expand concentrically and/or extend around the entire circumference of the elongated shaft 4020 (for example, as shown in FIGS. 44 and 45). A concentric positioning balloon may be partially or fully inflated to prevent the cutting elements 300 from injuring the native wall during advancement and/or further inflated to protect the native vessel wall and guide the cutting element to stay in the vessel central lumen while cutting obstructive material. The positioning provided by such embodiments may be especially beneficial when used with a helical cutting element as centering the longitudinal axis of the elongate shaft 4020 within the vessel doubles the effective treatment diameter of the cutting portion 300. For example, a helical cutting element 2010 with an 8 mm expanded diameter could be used to treat a 16 mm vessel if centered within the lumen and allowed to rotate 360 degrees. It will be appreciated that other cutting element diameters and vessel sizes are possible. As shown in FIGS. 42 and 43, in some embodiments the balloon 4080 comprises multiple lobes 4081 (e.g., lobes 4081a, 4081b, 4081c) that are independently inflatable/expandable. The different lobes 4081 may be selectively inflated for eccentric device positioning or all inflated for centering (as shown). In some embodiments the balloon

4080 includes multiple lobes 4081 but the lobes do not surround the entire circumference of the elongate shaft 4020 (e.g., at least two of the lobes are spaced apart around the circumference of the elongate shaft 4020).

Figures 46A, 46B:
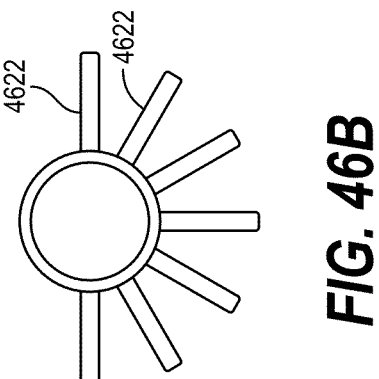
FIGS. 46A and 46B are perspective and end views, respectively, of a treatment assembly with a positioning element configured in accordance with several embodiments of the present technology.

The positioning element can comprise other expandable structures. For example, as shown in FIG. 46A, the positioning element can comprise a plurality of expandable struts 4622 carried at a distal portion of an elongated shaft 4620. In some embodiments, the struts 4622 are cut from a sidewall of the elongated shaft 4620. The struts 4622 can have a preferential bend and/or living hinge along their respective lengths such that, when the elongated member 4620 is shortened, for example by pulling back on an elongated member (not shown) coupled to the distal ends of the struts 4622 while holding the proximal end of the elongated shaft 4620 stationary, or advancing the proximal end of the elongated shaft 4620 while holding the distal ends of the struts 4622 stationary, the struts 4622 flex and expand outward. The struts 4622 may have sections with cut-outs to form a hinge location 4650. The hinge location may be at the mid-point of strut 4622 or at another location along the length of the strut 4622. For example, as shown in FIG. 46A, the hinge location may be towards the distal end of the strut 4622, to form an asymmetrical bend when the positioning element 4680 is expanded. In some embodiments, the struts 4622 are part of a separate expandable structure coupled to the distal portion of the elongated shaft 4620 (rather than cut from the elongated shaft 4620).

In any case, the struts 4622 may be positioned along only a portion of the circumference of the treatment assembly 100 (as shown in FIG. 46B), such that the struts 4622 push the treatment assembly 100 to one side of the vessel lumen when engaging the vessel wall at a different side. This asymmetry allows the user to direct the cutting portion 300 (in this case, an end-cutter, although other cutting portions 300 can be used with positioning element 4680) of the treatment assembly 100 towards a desired location in the vessel to remove occlusive material. The struts 4622 may be substantially parallel to the axis of the elongated shaft 4620 in a low-profile state and bow outward in a planar arc when the elongated shaft 4620 is shortened (as previously described), or the struts 4622 may be diagonally oriented in the low-profile state such that they form an expanding helix when the elongated shaft 4620 is shortened.

The positioning element of FIGS. 46A and 46B can be used with any of the treatment devices 101, treatment assemblies 100, cutting portions 300, and/or capture portions 200 disclosed herein. As but more examples, FIGS. 47A-47D show different combinations of the positioning device shown in FIG. 46A with the cutting portion 300 shown and described with respect to FIGS. 20A and 20B. In any of these variations, at least a portion of the treatment device 101 can be longitudinally and/or rotationally fixed relative to the elongated shaft 4620. For example, the first elongated member 111 may be longitudinally and/or rotationally fixed relative to the elongated shaft 4620 while the second elongated member 108 is free to rotate and/or translate relative to the elongated shaft 4620 (thereby enabling expansion/collapse of the cutting element 2010). As another example, the second elongated member 108 may be longitudinally and/or rotationally fixed relative to the elongated shaft 4620 while the first elongated member 111 is free to rotate and/or translate relative to the elongated shaft 4620 (thereby enabling expansion/collapse of the cutting element 2010).

Figures 47A, 47B, 47C, 47D:
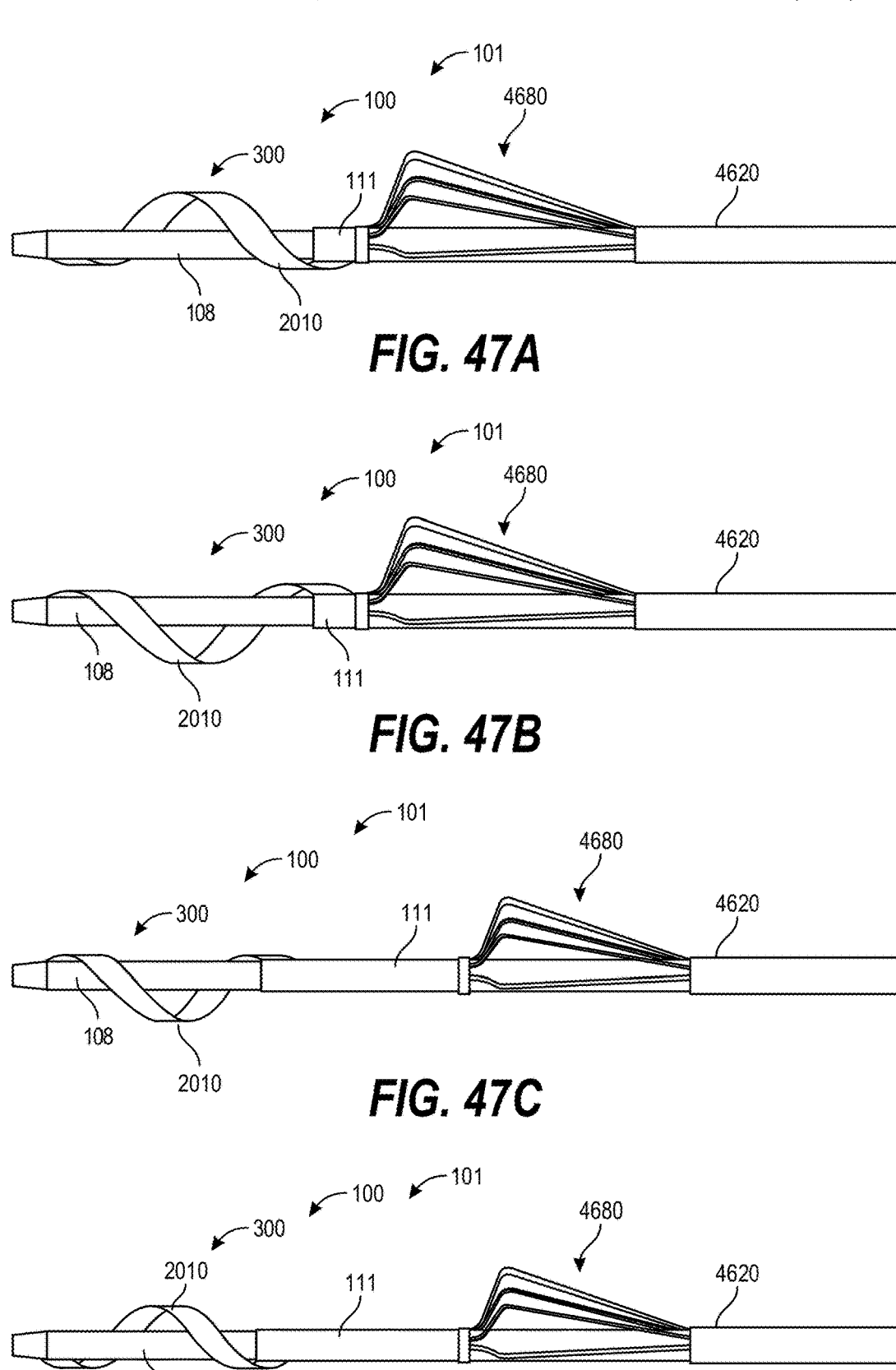
FIGS. 47A-47D show different positioning device and treatment assembly arrangements configured in accordance with several embodiments of the present technology.

As shown in FIG. 47A, the treatment device 101 and the positioning device can be arranged such that the cutting portion 300 is expanded at a location longitudinally adjacent the expanded positioning element 4680. In FIG. 47A, the cutting portion 300 is rotationally oriented such that the cutting element 2010 radially expands predominantly in the same direction of the expansion of the struts 4680. FIG. 47B shows an example in which the cutting portion 300 is expanded at a location longitudinally adjacent the expanded positioning element 4680. In FIG. 47B, the cutting portion 300 is rotationally oriented such that the cutting element 2010 radially expands predominantly in a direction that is different than (including the opposite of) that of the expanded struts 4680. In FIG. 47C, the cutting portion 300 is expanded at a location longitudinally spaced apart from the positioning element 4680 (for example, by advancement of the treatment device 101 relative to the positioning device, or vice versa) and the cutting portion 300 is oriented such that it expands predominantly in a direction that is different than that (including the opposite direction) of the expanded struts 4680. In FIG. 47D, the cutting portion 300 is expanded at a location longitudinally spaced apart from the positioning element 4680 (for example, by advancement of the treatment device 101 relative to the positioning device, or vice versa) and the cutting element 2010 is configured to expand predominantly in the direction of expansion of the expanded struts 4680. Expansion of any of the positioning elements herein can occur before, during, or after expansion and/or activation of the cutting portions.

Figure 48:
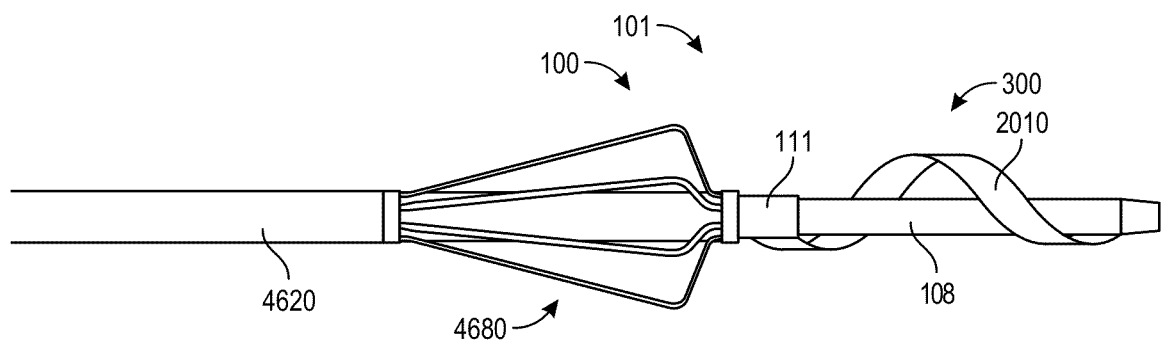
FIGS. 48 and 49 show a positioning device and treatment assembly arrangement configured in accordance with several embodiments of the present technology.
Figure 49:
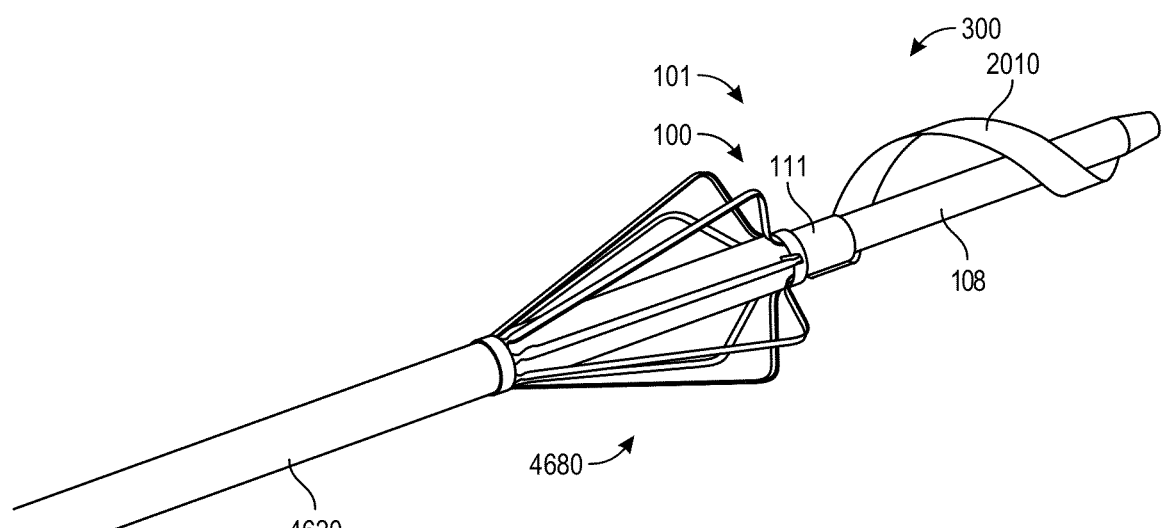

Similar to balloon 4080, while the positioning element 4680 shown in FIGS. 46A-47D is disposed eccentrically and/or on one side of the elongated shaft 4620, in some embodiments the positioning element 4680 (or any of the positioning elements of the present technology) may be configured to expand concentrically and/or extend around the entire circumference of the elongated shaft 4620 (for example, as shown in FIGS. 48 and 49).

While the positioning elements shown in FIGS. 40-49 are part of separate positioning devices, the same positioning elements can be directly incorporated into the treatment devices. To use FIG. 41A as an example, in some embodiments the positioning element is disposed directly on the second elongated member 108, and the treatment device 101 can include an inflation lumen extending from a proximal portion of the treatment device 101 to an interior region of the balloon 4080.

Any of the positioning elements disclosed herein (including the balloon 4080 and expandable struts 4622) may be configured to partially or completely occlude the vessel lumen (or other body lumen) when expanded. Positioning elements comprising a plurality of expandable struts, for example, may include an impermeable cover on all or a portion of the struts. This functionality has a secondary effect of reducing or removing the risk of embolic particles from traveling towards the heart (if the treatment vessel is a vein) or towards a limb or end organ (if the treatment vessel is an artery).

As previously mentioned, various approaches may be used to gain intravascular access to the obstructive material within a vessel lumen. In some embodiments, the method includes percutaneously accessing the blood vessel lumen (such as a vein) with a guidewire, advancing the introducer sheath (such as any of the introducers disclosed herein) over the guidewire and through the access site, and inserting a treatment device (such as any of the treatment devices disclosed herein, including treatment device 101) through a lumen of the introducer sheath into the blood vessel lumen. The distal portion of the treatment device 101 containing the treatment assembly 100 can be advanced to a target treatment site within the vessel lumen. The access site can be at, for example, a femoral vein, an internal jugular vein, or a popliteal vein. In some embodiments the method includes aspirating occlusive material or infusing a thrombolytic agent into or from the blood vessel before, during, or after extraction of the obstructive material with the treatment device.

In some embodiments, a guidewire may first be inserted into the blood vessel lumen and advanced through the obstructive material such that a distal terminus of the guidewire is distal of the obstructive material. Next, an introducer (such as, for example, introducer 103) may be delivered over the guidewire so that a distal portion of the introducer is positioned within the vessel lumen proximal of the obstructive material. In those embodiments in which the introducer includes a funnel at the distal portion of the introducer, the funnel is expanded into apposition with the blood vessel wall. The method can continue by inserting the treatment device 101 over the guidewire, through the introducer, and into the vessel lumen. In some embodiments, the treatment device 101 can be advanced through the obstructive material such that some or all of the treatment assembly 100 of the treatment device 101 is distal of the obstructive material. In some embodiments, the treatment assembly 100 can be advanced to a location in the vessel such that some or all of the treatment assembly 100 is proximal of the obstructive material. In some embodiments, the treatment assembly 100 can be advanced to a location in the vessel such that some or all of the treatment assembly 100 is within the obstructive material. In some embodiments, a distal capture assembly can be positioned distal to the obstructive material prior to positioning of the treatment assembly 100. In other embodiments, a distal capture assembly can be positioned at the same time as positioning of the treatment assembly.

In some methods of use, the cutting portion 300 and/or treatment assembly 100 is positioned distal to the obstructive material, expanded, and then manipulated (e.g., rotated, translated, or both), to separate obstructive material from the vessel wall. In those embodiments in which the cutting portion is a ribbon cutter, the inner member can be rotated to expand the ribbon to some or all of its expansion amount, and then manipulated to separate obstructive material from the treatment site. The treatment device can be readvanced for a further expansion and manipulation, in some cases to a larger expansion amount, for additional separation of obstructive material.

In some methods of use, the cutting portion 300 and/or treatment assembly 100 can be positioned within the obstructive material. For example, a positioning element of the present technology can push the cutting portion 300 of the treatment assembly 100 against the obstructive material, for example either by expansion of struts, inflation of a balloon, or other methods. The cutting portion 300 can be actuated, for example, by powering a motor or manual rotation of the cutting portion and/or cutting element. The treatment assembly 100 can be moved back and forth, or rotationally around, to separate additional obstructive material from the target area. The positioning element may be collapsed so that the treatment assembly 100 may be reoriented or translated in treatment site, and then re-expanded for further separation of obstructive material by treatment assembly 100. For treatment assemblies with an end cutting element (for example as depicted in FIGS. 31, 32A-32B, 33, 36A-36B and others) the treatment assembly may be pushed forward into obstructive material to separate the material from the treatment site.

Figures 50A, 50B, 51A, 51B:
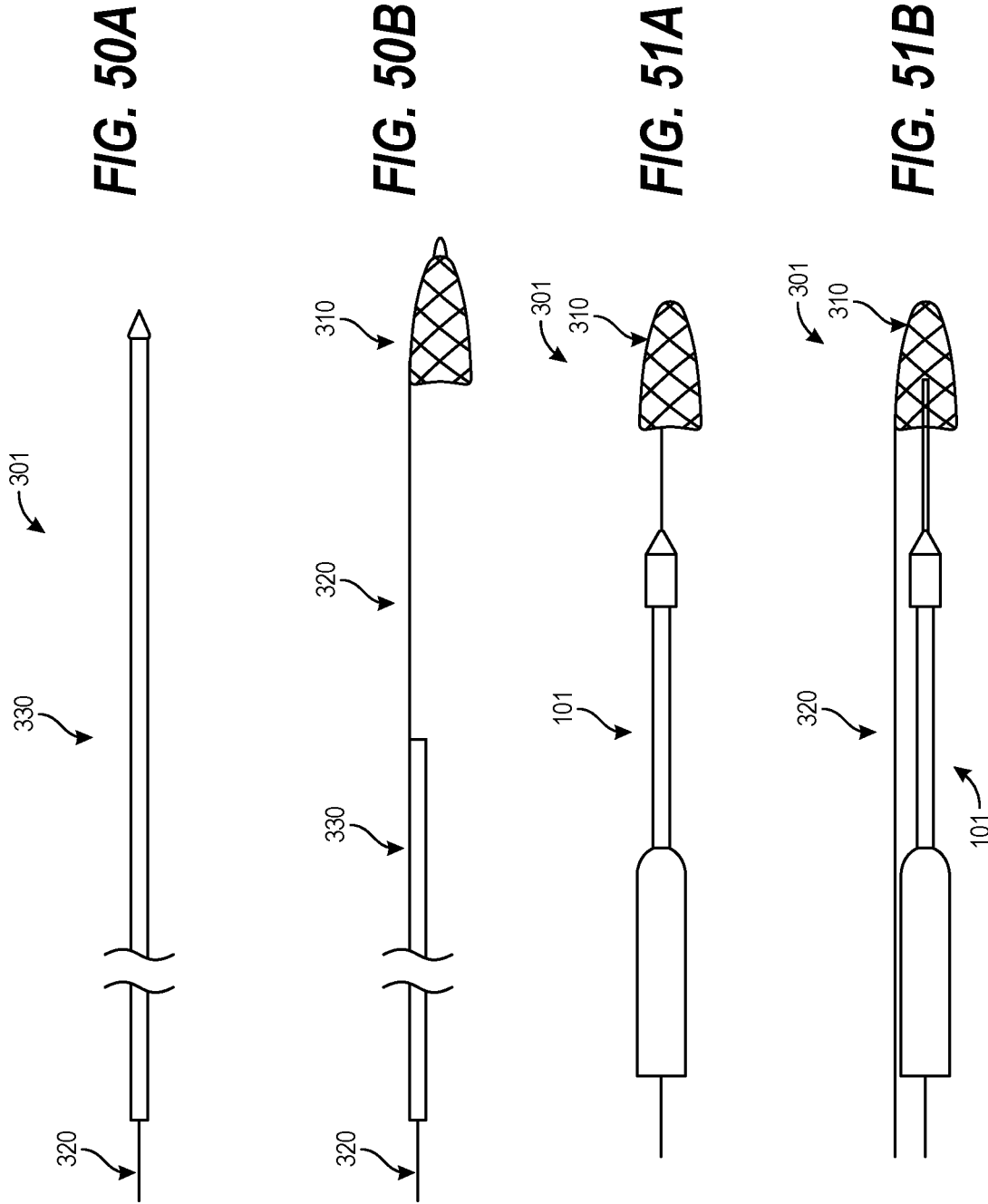
FIGS. 50A and 50B depict a distal capture device configured in accordance with several embodiments of the present technology.
FIGS. 51A and 51B schematically depict a treatment system including a capture device configured in accordance with several embodiments of the present technology.

In some embodiments, for example as shown in FIGS. 50A and 50B, the treatment system 10 may include a separate distal capture device 301. The distal capture device 301 may comprise an expandable basket 310 coupled to an elongated member 320. A restraining sheath 330 can be positioned over the basket 310 and elongated member 320 during positioning of distal capture device 301, as shown in FIG. 50A. Once at the desired site, the restraining sleeve is pulled back to allow the basket 310 to expand, as shown in FIG. 50B.

FIGS. 51A and 51B show example configurations of using a distal capture device 301 with the treatment device 101. In use, as shown in FIG. 51A, the distal capture device is first positioned at a distance distal to a treatment site. Once positioned, the restraining sheath 330 is pulled back to expand basket 310. The treatment device may be loaded onto elongated member 320 and advanced and positioned at a treatment site proximal to distal capture basket 310. In this manner, elongated member 320 acts as a guide rail. In this configuration, elongated member is sized to fit into internal lumen 20 of treatment device 101. In an alternate configuration, the distal capture device is positioned at the position distal to a treatment site, and then the treatment site is positioned with a separate guide rail such as a guidewire to the treatment site. The elongated member 320 of distal capture device 301 and the shaft 102 of the treatment device 101 are side-by-side in the introducer sheath. Alternately, the distal capture assembly and treatment device 101 are slidably or fixedly connected and positioned together at a treatment site.

Alternatively, as shown in FIG. 51B, the distal capture device 301 is positioned side by side in the vessel with the treatment device 101, and expanded distal to the treatment area.

Further embodiments of distal capture device 301 are provided in PCT Application No. PCT/US2022/071076, filed Mar. 10, 2022, which is incorporated by reference herein in its entirety.

Figure 52:
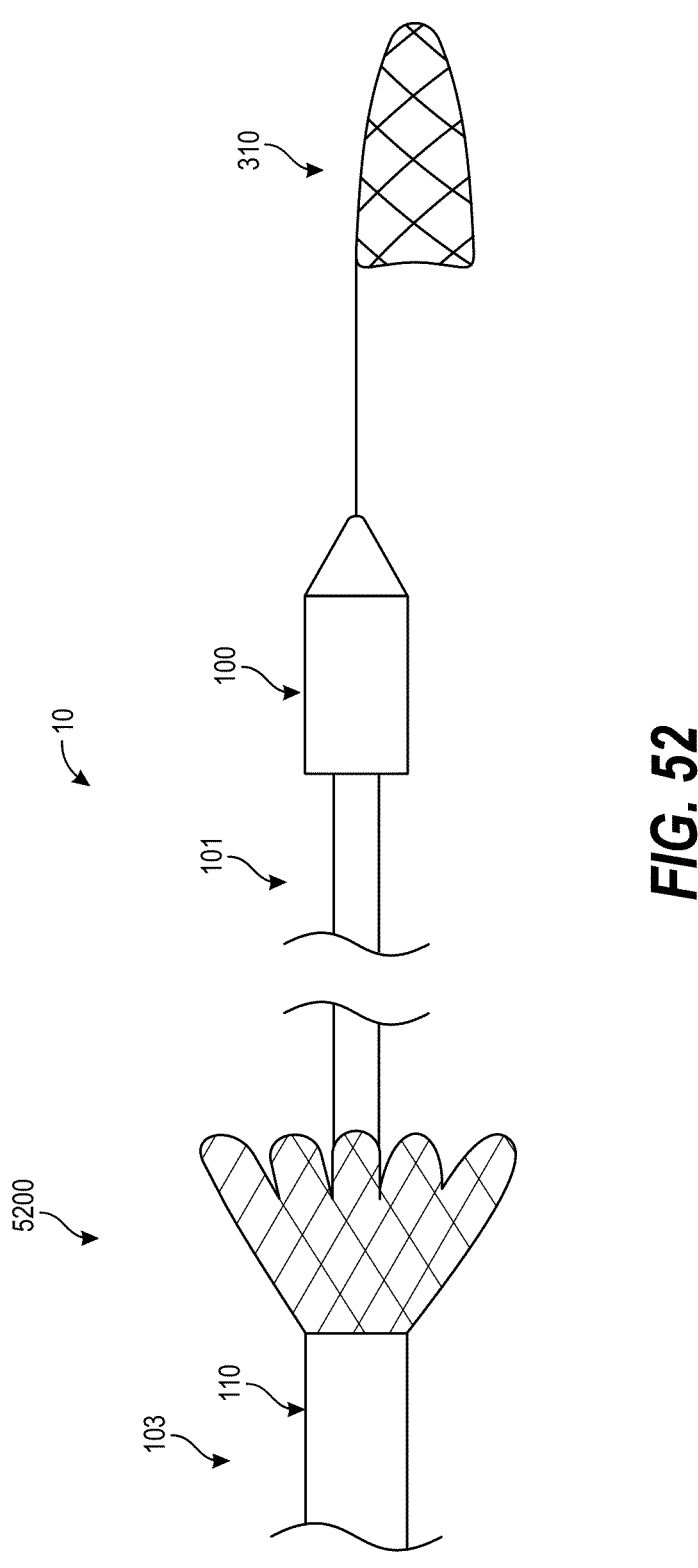
FIG. 52 schematically depicts a treatment system including a treatment device, a capture device, and an introducer sheath configured in accordance with several embodiments of the present technology.

In some embodiments, for example as shown in FIG. 52, the treatment system may include an introducer sheath 103. The introducer sheath may include features for aspiration of bulky material, for example a fluid line with large bore tubing and valves connected to an aspiration source such as a large syringe or aspiration pump. The introducer sheath may also include an expandable distal section 5200 to act as a funnel during removal of a treatment device 101 from the introducer sheath 103 in a matter to capture as much occlusive material removed and captured by the treatment assembly 100 of treatment device 101 as possible.

Any of the embodiments of treatment assembly 100 may be further enhanced with the addition of aspiration to remove material which has been separated from the treatment areas by means of the various cutting actions described. In an embodiment, the treatment device 101 includes a fluid line which fluidly connects the treatment assembly 100 to a Y-adaptor on the handle 12. In use, an aspiration pump is connected to the port on handle 12, thus connecting aspiration to the treatment assembly 100. The aspiration pump may be controlled manually by the user, for example with a manual or foot actuated valve that is opened or closed depending on if aspiration is desired at the treatment site. In another embodiment, the aspiration pump may be turned on automatically when a motor is turned on, for example, to rotate an internal cutter. In another embodiment, the aspiration source may be turned on only when it senses an increase in aspiration resistance due to a blockage to the treatment assembly, indicating the treatment assembly is against a surface such as occlusive material. The aspiration source may be a pump, a syringe, a connection to a suction source such as wall suction, or other aspiration source.

As previously mentioned, in some embodiments the treatment system 10 includes a flushing source, such as a syringe, a fluid pump, or a pressurized fluid bag, fluidly connected to a lumen of treatment device 101. The flush solution could be saline solution. In use, the flush could be used to continuously or intermittently direct occlusive material which has been separated from the treatment site towards a distal collection basket such as capture portion 200 of treatment device 101 or separate distal capture device 310.

In a variation, the treatment system 10 includes both an aspiration source (e.g., suction or aspiration source 18) and a flushing source (not shown). In this embodiment, the flush source and aspiration source could be turned on and off in tandem, so as to minimize the blood loss when aspirating occlusive material which has been separated from the treatment site by aspirating fluid which has flowed to treatment site from flush source, rather than aspirating blood.

At any point before, during, or after the foregoing methods, aspiration may be applied at the treatment site to remove the material which has been separated from the treatment site. Aspiration may be applied through treatment device via a fluid line connected to an aspiration source. Alternately, aspiration may be applied from the side arm of the introducer sheath.

At any point before, during, or after the foregoing methods, the treatment area may be flushed with or without aspiration to assist in separating and capturing occlusive material. The flush may be applied through the treatment device via a fluid line connected to a flush source. Alternately, flush may be applied from the side arm of the introducer sheath.

In an embodiment, both aspiration and flush may be applied to treatment site. For example, aspiration source may be connected to the treatment device and flush source may be connected to the introducer sheath. Conversely, aspiration source may be connected to the sheath and flush source may be connected to the treatment device. Alternately, both are connected to the treatment device, or both are connected to the sheath.

During separation and/or removal of obstructive material from a treatment site by the treatment assembly, the distal capture sheath may capture and contain any material that has not been aspirated or otherwise removed by treatment device.

During or after separation and/or removal of obstructive material from a treatment site by the treatment assembly, the treatment device is removed from the introducer sheath 103. Aspiration applied to the introducer sheath 103 reduces embolic particles during device removal. A funnel on the introducer sheath may also reduce the possibility of embolic particles remaining in the vasculature as the treatment device is removed.

CONCLUSION

Although many of the embodiments are described above with respect to systems, devices, and methods for retrieving clot material from a blood vessel lumen, the technology is applicable to other applications and/or other approaches, such as removal and/or modification of other structures within any body lumen. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1-52.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially," "about," and similar terms are used as terms of approximation and not as terms of degree, and are intended to account for the inherent variations in measured or calculated values that would be recognized by those of ordinary skill in the art.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A system for modifying and/or removing obstructive material from a lumen of a blood vessel, the system comprising:

a first elongated member having a proximal portion and a distal portion configured to be intravascularly positioned at a treatment site in a blood vessel adjacent obstructive material, wherein the first elongated member defines a lumen extending therethrough;

a second elongated member having a proximal portion and a distal portion configured to be intravascularly positioned at the treatment site, wherein the second elongated member is configured to be rotatably disposed within the lumen of the first elongated member;

a cutting element configured to cut obstructive material at the treatment site, the cutting element having a proximal end region at the distal portion of the first elongated member and a distal end region at the distal portion of the second elongated member, wherein rotation of the second elongated member relative to the first elongated member, or vice versa, causes the cutting element to expand away from a longitudinal axis of the second elongated member; and an expandable positioning element configured to be intravascularly delivered to the treatment site, wherein the positioning element is configured to be expanded into apposition with the vessel wall to position the cutting element closer to the obstructive material than before expansion of the positioning element, wherein the positioning element comprises a balloon.

2. The system of claim 1, wherein the positioning element is disposed on an elongate shaft defining a lumen therethrough, and wherein the first elongated member, second elongated member, and cutting element are configured to be positioning within the lumen of the elongate shaft.

3. The system of claim 2, wherein the elongate shaft comprises a tubular sidewall having a proximal portion and a distal portion, and wherein the sidewall comprises a window at the distal portion.

4. The system of claim 3, wherein the cutting element is configured to be positioned within the elongate shaft such that at least a portion of the positioning element is exposed through the window.

5. The system of claim 2, wherein the positioning element is positioned along only a portion of a circumference of the elongated shaft.

6. The system of claim 1, wherein the positioning element is translatable and/or rotatable relative to the first elongated member.

7. The system of claim 1, wherein the positioning element is translatable and/or rotatable relative to the second elongated member.

8. The system of claim 1, wherein the positioning element is configured to expand away from a central longitudinal axis of the elongated shaft to a maximum first radial distance and the cutting element is configured to expand away from the longitudinal axis of the second elongated member to a maximum second radial distance less than the first radial distance.

9. The system of claim 1, wherein the cutting element wraps at least partially around the longitudinal axis of the second elongated member as it extends between the first elongated member and the second elongated member.

10. The system of claim 1, wherein the cutting element is a ribbon.

11. The system of claim 1, wherein the cutting element has longitudinally extending edges, and wherein one or both longitudinally extending edges are sharpened.

12. The system of claim 1, wherein the cutting element has a proximally facing longitudinal edge and a distally facing longitudinal edge, and wherein only one of the proximally facing or distally facing longitudinal edge is sharpened.

13. The system of claim 1, wherein the cutting element is a first cutting element and the device comprises a second cutting element.

14. The system of claim 13, wherein the second cutting element is positioned radially inwardly of the first cutting element.

15. The system of claim 13, wherein the second cutting element is positioned radially outwardly of the first cutting element.

16. The system of claim 13, wherein the second cutting element is substantially linear.

17. The system of claim 13, wherein the second cutting element wraps at least partially around the longitudinal axis of the second elongated member.

18. The system of claim 13, further comprising a third elongated member positioned between the first and second elongated members, and wherein the second cutting element is at a distal portion of the third elongated member.

19. A system for modifying and/or removing obstructive material from a lumen of a blood vessel, the system comprising:

a treatment device comprising:

an elongated member, and a helical cutting element coupled to and extending at least partially around a distal portion of the elongated member, the cutting element configured to cut obstructive material at a treatment site, wherein manipulation of the elongated member causes the cutting element to expand away from a longitudinal axis of the elongated member, and a positioning device comprising:

an elongated shaft having a proximal portion and a distal portion configured to be intravascularly positioned at the treatment site, wherein the elongated shaft defines a lumen therethrough, and wherein the treatment device is configured to be positioned within the lumen, and an expandable positioning element disposed at the distal portion of the elongated shaft, the positioning element configured to be intravascularly delivered to the treatment site, wherein the positioning element is configured to be expanded into apposition with the vessel wall to position the cutting element closer to the obstructive material than before expansion of the positioning element, wherein the positioning element comprises a balloon.

* * * * *